United States Patent
Schaefer et al.

(10) Patent No.: US 10,829,742 B2
(45) Date of Patent: *Nov. 10, 2020

(54) PRODUCTION OF XYLITOL FROM GLUCOSE BY A RECOMBINANT STRAIN

(71) Applicant: ROQUETTE FRERES, Lestrem (FR)

(72) Inventors: Astrid Schaefer, Loerrach (DE); Melanie Diefenbacher, Allschwil (CH); Yiming Chang, Dietikon (CH); Sumire Honda Malca, Loerrach (DE); Markus Schwab, Loerrach (DE); Sophie Defretin, Bethune (FR); Tania Gerard, Nieppe (FR); Arnaud Heysen, Saint Floris (FR); Friederike Thor, Zurich (CH)

(73) Assignee: ROQUETTE FRERES, Lestrem (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/570,056

(22) Filed: Sep. 13, 2019

(65) Prior Publication Data

US 2020/0032224 A1     Jan. 30, 2020

Related U.S. Application Data

(63) Continuation of application No. 15/319,385, filed as application No. PCT/EP2015/063549 on Jun. 17, 2015, now Pat. No. 10,494,614.

(30) Foreign Application Priority Data

Jun. 18, 2014    (EP) .................................... 14305934

(51) Int. Cl.
     *C12P 7/18*          (2006.01)
     *C12N 9/04*          (2006.01)
     *C12N 15/81*         (2006.01)

(52) U.S. Cl.
     CPC ......... *C12N 9/0006* (2013.01); *C12N 15/815* (2013.01); *C12P 7/18* (2013.01); *C12Y 101/0101* (2013.01); *C12Y 101/01009* (2013.01); *C12Y 101/01011* (2013.01)

(58) Field of Classification Search
     None
     See application file for complete search history.

(56) References Cited

U.S. PATENT DOCUMENTS

| | | |
|---|---|---|
| 5,096,820 A | 3/1992 | Leleu et al. |
| 10,494,614 B2 * | 12/2019 | Schaefer ............... C12N 15/815 |
| 2011/0027847 A1 | 2/2011 | Matsushika et al. |

FOREIGN PATENT DOCUMENTS

| | | |
|---|---|---|
| EP | 0 421 882 A2 | 4/1991 |
| EP | 1 026 255 A1 | 8/2000 |
| WO | 94/10325 A1 | 5/1994 |

OTHER PUBLICATIONS

Watanabe, S. et al., "Complete Reversal of Coenyzme Specificity of Xylitol Dehydrogenase and Increase of Thermostability by the Introduction of Structural Zinc", Journal of Biological Chemistry, vol. 280, No. 11, Mar. 18, 2005, pp. 10340-10349.
Ehrensberger, A. H. et al. "Structure-Guided Engineering of Xylitol Dehydrogenase Cosubstrate Specificity", Structure, vol. 14, No. 3, Mar. 1, 2006, pp. 567-575.
Lafayette, P. R et al. "Arabitol Dehydrogenase as a Selectable Marker for Rice", Plant Cell Reports, vol. 24, No. 10, Dec. 1, 2005, pp. 596-602.
Puigbo, P. et al. "Optimizer: A Web Server for Optimizing the Codon Usage of DNA Sequences", Nucleic Acids Research, vol. 35, Jul. 1, 2007, pp. W126-W131.
Shi, N.-Q. et al. "Characterization and Complementation of Pichia Stipitis Mutant Unable to Grow on D-Xylose or L-Arabinose", Applied Biochemistry and Biotechnology, vol. 84-86, Apr. 1, 2000, pp. 201-216.
Zhu, H.-Y. et al. "Production of D-Arabitol by a Newly Isolated Kodamaea Ohmeri", Bioprocess Biosystems Engineering, vol. 33, No. 5, 2010, pp. 565-571.
Database EMBL [Online] Accession No. AY863020, "Synthetic construct arabitol dehydrogenase gene, complete cds." Jan. 17, 2005, p. 1, XP-002729335.
Database EMBL [Online] Accession No. AB091690, "Gluconobacter oxydans xdh gene for xylitol dehydrogenase, complete cds." Sep. 19, 2002, p. 1, XP-002729336.
Database UniProt [Online] Accession No. P58708, "Full=D-arabinitol 4-dehydrogenase" Jan. 31, 2002, p. 1, XP-002743035.
Aug. 14, 2015 Written Opinion issued in International Application No. PCT/EP2015/063549.
Accession No. AAN32619, "arabitol dehydrogenase [*Escherichia coli*]", GenBank. Oct. 2, 2002.
Accession No. WP-011002060, "D-arabinitol 4-dehydrogenase [ralstonia solanacearum]", Genbank. May 24, 2013.

\* cited by examiner

*Primary Examiner* — David Steadman
(74) *Attorney, Agent, or Firm* — Oliff PLC

(57) ABSTRACT

The present invention relates to a recombinant microbial host for the production of xylitol, the recombinant microbial host containing a nucleic acid sequence encoding a $NAD^+$-specific D-arabitol 4-oxidoreductase (EC 1.1.1.11) using D-arabitol as substrate and producing D-xylulose as product, and a nucleic acid sequence encoding a NADPH-specific xylitol dehydrogenase using D-xylulose as substrate and producing xylitol as product.

12 Claims, 44 Drawing Sheets

Figure 1:
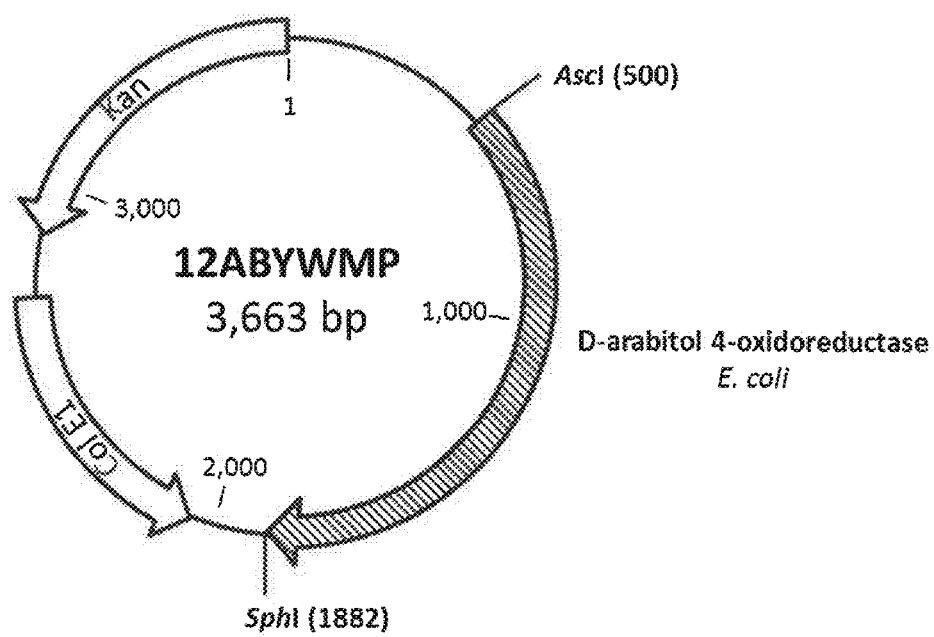

Specification includes a Sequence Listing.

PRODUCTION OF XYLITOL FROM GLUCOSE BY A RECOMBINANT STRAIN

CROSS-REFERENCE TO RELATED APPLICATIONS

This is a Continuation of application Ser. No. 15/319,385 filed Dec. 16, 2016, which in turn is a U.S. national stage application of International Patent Application No. PCT/EP2015/063549, filed Jun. 17, 2015, which claims priority to EP 14305934.3, filed Jun. 18, 2014. The disclosure of the prior applications is hereby incorporated by reference herein in its entirety.

FIELD OF THE INVENTION

The present invention relates to a method of using genetically modified microorganisms for the manufacture of xylitol, and a method of preparing a genetically modified microorganism that is capable of converting in one step readily available carbon sources, such as D-glucose, into xylitol.

BACKGROUND OF THE INVENTION

Xylitol is a polyalcohol or sugar alcohol (alditol) of formula $(CHOH)_3(CH_2OH)_2$, that has applications in hygiene and nutraceutical formulations and products.

Xylitol is used as a diabetic sweetener which is roughly as sweet as sucrose with 33% fewer calories. Unlike other natural or synthetic sweeteners, xylitol is actively beneficial for dental health by reducing caries to a third in regular use and helpful to remineralization.

Xylitol is naturally found in low concentrations in the fibers of many fruits and vegetables, and can be extracted from various berries, oats, and mushrooms, as well as fibrous material such as corn husks and sugar cane bagasse, and birch.

However, industrial production starts from xylan (a hemicellulose) extracted from hardwoods or corncobs, which is hydrolyzed into xylose and catalytically hydrogenated into xylitol.

Purification of xylose and also xylitol presents therefore a significant problem. A number of processes of this type are known. U.S. Pat. Nos. 4,075,406 and 4,008,285 can be mentioned as examples.

The reduction of D-xylose into xylitol can also be achieved in a microbiological process using either yeast strains isolated from nature (wild type strains) or genetically engineered strains.

However, obtaining the substrate, D-xylose, in a form suitable for yeast fermentation is a problem because inexpensive xylose sources such as sulphite liquor from pulp and paper processes contain impurities which inhibit yeast growth.

An attractive alternative method for the manufacture of xylitol is obtaining it by fermentation of a cheap and readily available substrate, such as D-glucose.

In the state of the art, there are some recombinant microorganisms described able to produce xylitol in certain amounts during a one-step fermentation of any common carbon sources other than D-xylose and D-xylulose.

These recombinant microorganisms, especially osmophilic yeasts, are for example *Zygosaccharomyees rouxii*, *Candida polymorpha*, and *Torulopsis candida*, initially known as producers of significant amounts of a xylitol closely related pentitol, which is D-arabitol, from D-glucose (Lewis D. H. & Smith D. C., 1967, *New Phytol.* 66:143-184).

Thus, the international patent application WO 94/10325 provides methods for constructing such recombinant hosts being capable of producing xylitol when grown on carbon sources other than D-xylulose or D-xylose, and other than polymers or oligomers or mixtures thereof.

In the current patent application, this goal is achieved through modification of the metabolism of the desired microorganism, preferably a naturally occurring yeast microorganism, by introducing and expressing desired heterologous genes.

This goal is also achieved by further modification of the metabolism of such desired microorganism, so as to overexpress and/or inactivate the activity or expression of certain genes homologous to such microorganism in its native state.

The method provided in this patent application for the production of xylitol utilized an altered D-arabitol biosynthesis pathway, and such pathway being notably altered by extending the preexisting D-arabitol pathway by the introduction and overexpression of the genes coding for D-xylulose-forming D-arabitol dehydrogenase (EC 1.1.1.11) and xylitol dehydrogenase (EC 1.1.1.9) into an D-arabitol-producing microorganism.

However, the yield of xylitol in the trials described in WO 94/10325 was only approximately 7.7 g/l after 48 hours of cultivation in a medium with yeast extract.

To try to optimize this first result, it was further proposed in WO 94/10325 to inactivate, using mutagenesis or gene disruption, the genes coding for transketolase (EC 2.2.1.1) and/or the gene coding for D-xylulokinase (EC 2.7.1.17), and also to overexpress the genes coding for the enzymes of the oxidative branch of the pentose-phosphate pathway, and specifically D-glucose-6-phosphate dehydrogenase (EC 1.1.1.49) and/or 6-phospho-D-gluconate dehydrogenase (EC 1.1.1.44) and/or D-ribulose-5-phosphate epimerase gene (EC 5.1.3.1) in such microorganisms.

But, whatever the genetic combination employed, the xylitol titer was never more than 9 g/l.

There is therefore still an unsatisfied need for a better genetic manipulation of xylitol producing strains in order to optimize its production, and thus make it commercially profitable.

SUMMARY OF THE INVENTION

The present invention relates to a recombinant host cell capable of producing xylitol, wherein said host cell comprises:

an heterologous nucleic acid sequence encoding a $NAD^+$-specific D-arabitol 4-oxidoreductase (EC 1.1.1.11) using D-arabitol as substrate and producing D-xylulose as product; and, an heterologous nucleic acid sequence encoding a NADPH-specific xylitol dehydrogenase using D-xylulose as substrate and producing xylitol as product.

Preferably, the host cell does not consume D-arabitol as a sole carbon source. More preferably, the host cell is selected from bacteria, fungi and yeast. In a preferred embodiment, the host cell is an osmophilic or osmotolerant yeast, in particular *Pichia ohmeri*.

Preferably, the $NAD^+$-specific D-arabitol 4-oxidoreductase (EC 1.1.1.11) is from *E. coli* or *Ralstonia solanacearum*. More preferably, the $NAD^+$-specific D-arabitol 4-oxidoreductase (EC 1.1.1.11) comprises or consists in the sequence of SEQ ID No 2 or 43 or a sequence with 1-3 additions, substitutions or deletions of amino acids. In a preferred embodiment, the sequence encoding the NAD$^+$-specific D-arabitol 4-oxidoreductase (EC 1.1.1.11) comprises or consists in the sequence of SEQ ID No 3 or 42.

Preferably, the NADPH-specific xylitol dehydrogenase is a xylitol dehydrogenase from *Pichia stipitis* or *Gluconobacter oxydans* mutated for changing the cofactor specificity from NADH to NADPH. More preferably, the NADPH-specific xylitol dehydrogenase comprises or consists in the sequence of SEQ ID No 5 or 8 or a sequence with 1-3 additions, substitutions or deletions of amino acids. In a preferred embodiment, the sequence encoding the NADPH-specific xylitol dehydrogenase comprises or consists in the sequence of SEQ ID No 6 or 9.

Preferably, the host cell is capable of producing a xylitol titer of at least 15 g/l in the supernatant after a 48 h culture.

Preferably, the host cell is a strain selected from strains I-4982, I-4960 and I-4981 deposited at the CNCM.

Preferably, the host cell comprises several copies of a sequence encoding a NAD$^+$-specific D-arabitol 4-oxidoreductase and/or several copies of a sequence encoding the NADPH-specific xylitol dehydrogenase.

The present invention also relates to a method for producing xylitol comprising culturing a recombinant host cell as described above, and recovering xylitol.

It additionally relates to a nucleic acid comprising or consisting in a nucleic acid sequence selected from the group consisting of SEQ ID No 1, 3, 7 and 9, an expression cassette or vector comprising said nucleic acid.

Finally, the present invention relates to the use of a recombinant host cells according to the present invention for producing xylitol.

DETAILED DESCRIPTION OF THE INVENTION

Definitions

As used herein, by a "carbon source other than D-xylose and D-xylulose" is meant a carbon substrate for xylitol production other than D-xylose and D-xylulose or polymers or oligomers or mixtures thereof (such as xylan and hemicellulose). The carbon source preferably includes D-glucose, and various D-glucose-containing syrups and mixtures of D-glucose with other sugars.

As used herein, by "gene" is meant a nucleic acid sequence that may code for a protein, in particular a DNA sequence.

As used herein, by "vector" is meant a plasmid or any other DNA sequence which is able to carry genetic information, specifically DNA, into a host cell. The vector can further contain a marker or reporter suitable for use in the identification of cells transformed with the vector, and origins of replication that allow for the maintenance and replication of the vector in one or more prokaryotic or eukaryotic hosts. A "plasmid" is a vector, generally circular DNA that is maintained and replicates autonomously in at least one host cell.

As used herein, by "expression vector" is meant a vector similar to a vector but which supports expression of a gene or encoding nucleic acid that has been cloned into it, after transformation into a host. The cloned gene or encoding nucleic acid is usually placed under the control of (i.e., operably linked to) certain control sequences such as promoter sequences, that can be provided by the vector or by the recombinant construction of the cloned gene. Expression control sequences will vary depending on whether the vector is designed to express the operably linked gene in a prokaryotic or eukaryotic host and can additionally contain transcriptional elements such as enhancer elements (upstream activation sequences) and termination sequences, and/or translational initiation and termination sites.

As used herein, by "host" is meant a cell, prokaryotic or eukaryotic, that is utilized as the recipient and carrier of recombinant material.

As used herein, by "Oxidative Branch of the Pentose-Phosphate Pathway" is meant to include the part of the pentose-phosphate shunt that catalyzes oxidative reactions, such as reactions catalyzed by D-glucose-6-phosphate dehydrogenase (EC 1.1.1.49) gluconolactonase (EC 3.1.1.17), and 6-phospho-D-gluconate dehydrogenase (EC 1.1.1.44), and that utilizes hexose substrates to form pentose phosphates. The "non-oxidative" part of the pentose-phosphate pathway (which also catalyzes the net formation of ribose from D-glucose) is characterized by non-oxidative isomerizations such as the reactions catalyzed by transketolase (EC 2.2.1.1), ribose-5-phosphate isomerase (EC 5.3.1.6), D-ribulose-5-phosphate-3-epimerase (EC 5.1.3.1) and transaldolase (EC 2.2.1.2). See Biological Chemistry, H. R. Mahler & E. H. Cordes, Harper & Row, publishers, New York, 1966, pp. 448-454.

As used herein, by "encoding nucleic acid" is meant a nucleic acid molecule (preferably DNA). Encoding nucleic acid is capable of encoding a protein and can be prepared from a variety of sources. These sources include genomic DNA, cDNA, synthetic DNA, and combinations thereof.

"Heterologous", as used herein, is understood to mean that a gene or encoding sequence has been introduced into the cell by genetic engineering. It can be present in episomal or chromosomal form. The gene or encoding sequence can originate from a source different from the host cell in which it is introduced. However, it can also come from the same species as the host cell in which it is introduced but it is considered heterologous due to its environment which is not natural. For example, the gene or encoding sequence is referred to as heterologous because it is under the control of a promoter which is not its natural promoter, it is introduced at a location which differs from its natural location. The host cell may contain an endogenous copy of the gene prior to introduction of the heterologous gene or it may not contain an endogenous copy.

OBJECT OF THE INVENTION

According to the invention, the native metabolic pathways of a specific microbial host are manipulated so as to decrease or eliminate the utilization of carbon into purposes other than xylitol production.

Such a genetically modified host strain is thus able to produces xylitol in one fermentation step with a high yield. For instance, the xylitol titer after 48 h of culture in the supernatant is more than 15 g/l, preferably more than 25 g/l, still more preferably more than 50, 60, 70, 80, 90 or 100 g/l.

In the practical realization of the invention, the genetically modified host of the invention is also characterized by its ability to synthesize xylitol from structurally unrelated carbon sources such as D-glucose, and not just from D-xylose and/or D-xylulose.

Preferably, the genetically modified host of the invention is also capable of secreting the synthesized xylitol into the medium.

Specifically, in the exemplified and preferred embodiments, the genetically modified host of the invention is characterized by a pathway in which arabitol is an intermediate in xylitol formation.

Accordingly, the recombinant host strain of the invention is characterized by the following genetic alterations:

(1) a heterologous nucleic acid encoding a protein possessing $NAD^+$-specific D-arabitol 4-oxidoreductase (D-xylulose-forming) activity has been introduced into the host cell thus providing for the conversion of D-arabitol to D-xylulose; and (2) a heterologous nucleic acid encoding a protein possessing NADPH-specific xylitol dehydrogenase activity has been introduced into the host cell—thus providing for the conversion of D-xylulose to xylitol.

The Choice of the Microorganism

The microorganisms or host strains suitable for the present invention are capable of producing D-arabitol from glucose. More particularly, they are capable of producing significant amounts of D-arabitol from glucose under high osmotic pressure medium.

By "high osmotic pressure medium" is intended here to refer to medium containing 10-60% D-glucose, preferably about 25% D-glucose.

By "significant amounts of D-arabitol" is intended at least 100 g/L of D-arabitol. In particular, a microorganism or host strain is considered as producing significant amounts of D-arabitol when the microorganism or host strain produces 100 g/L D-arabitol in a medium containing 25% D-glucose in batch conditions.

Examples of host strains capable of producing significant amounts of D-arabitol from glucose include the osmophilic or osmotolerant yeasts, in particular those belonging to the species *Pichia*, *Kodamaea*, *Candida*, *Zygoaccharomyces*, *Debaromyces*, *Metschnikowia* and *Hansenula*; or the D-arabitol producing fungi, in particular those belonging to the species *Dendryphiella* and *Schizophyllum*, in particular *Dendryphiella salina* and *Schizophyllum commune*.

Examples of the microorganisms of the genus *Pichia* include *Pichia ohmeri*, *Pichia stipitis*, *Pichia farinosa*, *Pichia haplophila*. Examples of the microorganisms of the genus *Candida* include *Candida polymorpha* and *Candida tropicalis*. Examples of the microorganisms of the genus *Zygoaccharomyces* include *Zygoaccharomyces rouxii*. Other examples include *Torulopsis candida* and *Torulaspora hansenii*. Examples of the microorganisms of the genus *Metschnikowia* include *Metschnikowia pulcherrima*, *Metschnikowia reukaufii*, *Metschnikowia bicuspidate*, *Metschnikowia lunate* and *Metschnikowia zobellii*. As specific strains, *Metschnikowia pulcherrima* ATCC 18406, *Metschnikowia reukaufii* ATCC 18407, *Metschnikowia bicuspidate* ATCC 24179, *Metschnikowia lunala* ATCC 22033, *Metschnikowia zobellii* ATCC 22302 and *Metschnikowia pulcherrima* FERM BP-7161 can be mentioned. These strains can be obtained from American Type Culture Collection, Address: 12301 Parklawn Drive, Rockville, Md. 20852, United States of America. *Metschnikowia pulcherrima* FERN BP-7161 was originally deposited at the National Institute of Bioscience and Human-Technology, Agency of Industrial Science and Technology, Ministry of International Trade and Industry (postal code: 305-8566, 1-3 Higashi 1-Chome, Tsukuba-shi, Ibaraki-ken, Japan) on Jan. 16, 1998, under the deposition number of FERM P-16592 and transferred from the original deposit to international deposit based on Budapest Treaty on May 15, 2000, and has been deposited as deposition number of FERM BP-7161. In a specific aspect, the microorganism has the accession number FERM BP-7161. For more information, refer to EP1065276.

The microorganism can be genetically engineered in order to improve its capacity of producing D-arabitol and/or reducing its capacity to use D-arabitol for a goal distinct from xylitol production.

For the invention, the host strain is advantageously chosen by its specific metabolic attributes:
- it may be a producer of significant amounts of D-arabitol from glucose as detailed above, in particular under high osmotic pressure medium, for example medium containing 10-60% D-glucose, and preferably 25% D-glucose ("Normal" medium usually contains only 2-3% glucose.)
- it may not consume D-arabitol as a sole carbon source;
- its redox balance permits the generation of the cofactors needed for the corresponding ketopentose/pentose alcohol conversion.

In one embodiment of the invention, the osmophilic yeast *Pichia ohmeri* (and their mutagenized derivatives) has been employed as a model and as a preferred host. *Pichia ohmeri* has initially been isolated from cucumber brine and commonly used in food industry for fermentation in pickles, rinds, and fruits.

It is known by the one skilled in the art that yeasts species such as *Pichia*, *Zygosaccharomyces*, *Debaromyces* and *Hansenula* are able to grow in low water activity environments, on the opposite of *Saccharomyces cerevisiae*. These osmotolerant or osmophilic yeasts accumulate compatible solute like glycerol, D-arabitol, erythritol and mannitol which protect and stabilize enzymes, thereby enabling the cellular functions in osmotic conditions of growth. The polyols produced also play a role in redox balancing.

In a preferred aspect, the microorganism is *Pichia ohmeri*. Indeed, the main characteristic of the host strain *Pichia ohmeri* is to produce only D-arabitol as compatible solute, in contrast to *Zygosaccharomyces rouxii* producing glycerol and D-arabitol. In addition, the metabolic pathway from glucose to D-arabitol is well known in *Pichia ohmeri*.

As described in *Zygoaccharomyces rouxii* (J. M. INGRAM and W. A. WOOD, 1965, Journal of Bacteriology, Vol. 89, N°5, 1186-1194), the carbon flux in *Pichia ohmeri* goes through the oxidative part of the Pentose-Phosphate Pathway (PPP) to convert D-Glucose into D-ribulose-5-P with the concomitant production of two molecules of NADPH. D-ribulose-5-P is dephosphorylated to D-ribulose and then reduced to D-arabitol. In *Pichia ohmeri* host strain, the Pentose Phosphate Pathway (PPP) is very active and has been determined to be higher than 50%.

In a preferred embodiment, the host cell is a mutant *Pichia ohmeri* deposited on Mar. 7, 2012, with the Collection Nationale de Cultures de Microorganismes [National Collection of Microorganism Cultures] of the Institut Pasteur (CNCM). 25 rue du Docteur Roux, 75724 PARIS Cedex 15, under number 1-4605.

Redox Reactions and Enzymes

The cofactors NADH and NADPH are essential to a multitude of biological functions, acting in so-called redox reactions as carriers of electrons from one reaction to another. Cells need to maintain the metabolic equilibrium of the two redox couples $NADH/NAD^+$ and $NADPH/NADP^+$ knowing that the $NADPH/NADP^+$ couple is maintained in a more reduced state than the $NADH/NAD^+$ couple to provide a thermodynamic driving force. NADH, which is mostly found in the oxidized form $NAD^+$, is the main co-factor in catabolic reactions where it is involved in the oxidative release of energy from nutrients. In contrast to NADH, NADPH is re-oxidized exclusively in anabolic reactions or during times of oxidative stress.

Any metabolic engineering strategy that involves redox reactions has to function under these cellular constraints. It has been done in the genetically modified strain that is the object of the invention.

As found by the inventor, notably described in the PhD Thesis entitled "Contribution à l'étude du metabolisme des pentitols chez Pichia ohmeri" (Sophie Huchette, University of Sciences and Technics of Lille, 1992), it has been demonstrated that the reactions involved into the oxidoreduction of ketopentoses are catalyzed by two different enzymes.

Thus, the host strain has an enzyme defined as a NADPH-specific D-ketopentose-oxidoreductase, forming D-arabitol from D-ribulose and forming xylitol from D-xylulose. The host strain also possesses a NADH-specific D-ketopentose-oxidoreductase, forming ribitol and xylitol respectively from D-ribulose and D-xylulose. This enzyme is closed to the well-known $NAD^+$-specific xylitol dehydrogenase E.C 1.1.1.9 from *Pichia stipitis* (XYL2). As only intracellular D-ribulose is available in contrast to D-xylulose, the host strain balances the NADPH/$NADP^+$ redox couple directly with the re-oxidization of NADPH through cytosolic formation of D-arabitol from D-ribulose. Then, D-arabitol is secreted into the broth via a passive diffusion.

The inventors found that the lack in intracellular D-xylulose would be the main reason for the non-production of xylitol by the host strain even if *Pichia ohmeri* possesses all the enzymatic tools to produce this polyol via NADH- or NADPH-specific-D-ketopentose-oxidoreductase.

Indeed, it was chosen to clone into the wild type host strain *Pichia ohmeri* a gene encoding a protein possessing $NAD^+$-specific D-arabitol 4-oxidoreductase (D-xylulose-forming) activity (E.C.1.1.1.11) allowing the cytosolic D-arabitol to be converted to D-xylulose and NADH.

So, intracellular D-xylulose becomes available into the genetically modified strain and could be reduced by the intrinsic NADH- and NADPH-specific-D-ketopentose-oxidoreductase. However, the strain is devoid of the endogenous enzymes able to efficiently transform D-xylulose into xylitol. Therefore, it is necessary to genetically engineer the strain in order to introduce a heterologous xylitol dehydrogenase.

In the patent WO 94/10325, it was chosen to clone the $NAD^+$-specific Xylitol dehydrogenase (E.C 1.1.1.9) from *Pichia stipitis* (XYL2) allowing the production of xylitol and balancing the NADH/$NAD^+$ redox couple with the oxidation of NADH produced by the previous metabolic step. But as mentioned before, the results are not really convincing.

The inventors found that, by cloning a gene encoding a mutated protein possessing NADPH-specific xylitol dehydrogenase, the D-xylulose is converted to xylitol to balance the NADPH/$NADP^+$ redox couple such as done by the intrinsic production of D-arabitol from D-ribulose.

Due to its low affinity of the NADPH-specific D-ketopentose-oxidoreductase for D-arabitol, the *Pichia ohmeri* wild type host strain does not consume the extracellular D-arabitol.

Because of the introduction of a $NAD^+$-specific D-arabitol 4-oxidoreductase (D-xylulose-forming) activity into the genetically modified strain, the D-arabitol produced into the broth could be well consumed by the modified strain the same way as the cytosolic D-arabitol.

Consequently, xylitol is produced at the same time from intracellular and extracellular D-arabitol.

Its production could be improved by enhancing the efficiency of the xylitol pathway extension to totally avoid the exportation of the intermediary D-arabitol.

Thus only xylitol would be produced from D-glucose with the same physiological effect as D-arabitol. This improvement could be the result of the genetic modifications but also of the adaptation of the culture conditions.

The Choice of the Two Enzymatic Activities to be Cloned in the Host Strain

The choice of these two enzymatic activities is supported by their cofactor specificity, as described above.

The first enzyme oxidizes D-arabitol into D-xylulose.

Two types of D-arabitol dehydrogenases are known: D-xylulose-forming (EC 1.1.1.11) (D-arabinitol $NAD^+$ 4-oxidoreductase) and D-ribulose-forming (EC 1.1.1.250). Unless otherwise stated, it is the D-xylulose-forming arabitol dehydrogenase that is intended herein and referred to herein as arabitol dehydrogenase. D-ribulose-forming dehydrogenases are found in wild-type yeasts and fungi.

D-xylulose-forming arabitol dehydrogenases are mainly known in bacteria. For instance, they have been identified in *Enterobacteriaceae*, in particular *E. coli*, *Klebsiella aerogenes*, and *Aerobacter aerogenes* strain PRL-R3, in *Gluconobacter oxydans*, and additionally also in *Pichia stipitis*. In particular, several enzymes are referenced in UniprotKB database, such as, *Klebsiella pneumoniae* (# O052720), *Ralstonia solanacearum* (# P58708), *Yersinia pestis* (# P58709), *Aerobacter aerogenes* (# L8BEF0), *E. coli* (# K3EX35, I2ZSJ5, W1BYD6, W1H8N7, E7U4R7).

For the purposes of the present invention, *Escherichia coli* is the preferred source of the $NAD^+$-specific D-arabitol 4-oxidoreductase (D-xylulose-forming) gene. More specifically, its amino acid sequence is disclosed in SEQ ID No 2. In particular, SEQ ID Nos 1 and 3 disclose nucleic acids encoding $NAD^+$-specific D-arabitol 4-oxidoreductase of *Escherichia coli*. The encoding sequence has been optimized for *Pichia ohmeri* by taking into account its codon specificity.

In addition, *Ralstonia solanacearum* is also a preferred source of the $NAD^+$-specific D-arabitol 4-oxidoreductase (D-xylulose-forming) gene. More specifically, its amino acid sequence is disclosed in SEQ ID No 43. In particular, SEQ ID No 42 disclose nucleic acids encoding $NAD^+$-specific D-arabitol 4-oxidoreductase of *Ralstonia solanacearum*. The encoding sequence has been optimized for *Pichia ohmeri* by taking into account its codon specificity.

The second enzyme converts D-xylulose into xylitol.

Although the majority of yeasts and fungi possess an endogenous xylitol dehydrogenase (EC 1.1.1.9) gene, the change of their cofactor specificity from NADH to NADPH is necessary for the implementation of the present invention. Indeed, a key aspect of the present invention is to use a NADPH-specific xylitol dehydrogenase. In addition, this enzyme is preferably overexpressed in the host.

Numerous xylitol dehydrogenases are known and several scientific articles teach how to change the cofactor specificity from NADH to NADPH. Watanabe et al (*J; Biol. Chem.*, 2005, 280, 10340-10345) discloses mutated xylitol dehydrogenase of *Pichia stipitis* with a modified cofactor specificity, especially the triple mutant (D207A/I208R/F209S) and the quadruple mutant (D207A/I208R/F209S/N211R). The amino acid sequence of the quadruple mutant is disclosed in SEQ ID No 5. A double mutant of xylitol dehydrogenase of *Gluconobacter oxydans* (D38S/M39R) with a NADPH cofactor specificity is disclosed in Ehrensberger et al (2006, *Structure*, 14, 567-575). The amino acid sequence of the double mutant is disclosed in SEQ ID No 8.

The mutation and cloning of the *Pichia stipitis* XYL2 nucleic acid sequence encoding the NADPH-specific xylitol dehydrogenase have been prepared by the inventors. In particular, SEQ ID Nos 4 and 6 disclose nucleic acids encoding specific NADPH xylitol dehydrogenase of *Pichia stipitis*.

Alternatively, the inventors have also performed the mutation and cloning of the *Gluconobacter oxydans* nucleic acid sequence encoding the NADPH-specific xylitol dehydrogenase. In particular, SEQ ID Nos 7 and 9 disclose nucleic acids encoding NADPH specific xylitol dehydrogenase of *Gluconobacter oxydans*. The encoding sequence has been optimized for *Pichia ohmeri* by taking into account its codon specificity.

Expression Cassette, Vector and Recombinant Host Cell

In a particular aspect, the present invention relates to a nucleic acid comprising an encoding sequence optimized for Pichia ohmeri selected from the group consisting of SEQ ID No 3, 7, 9 and 42.

It further relates to an expression cassette comprising a nucleic acid comprising an encoding sequence optimized for Pichia ohmeri selected from the group consisting of SEQ ID No 1, 3, 7, 9 and 42.

It also relates to the nucleic acid construct of SEQ ID No 4 and a nucleic acid comprising said nucleic acid construct.

In addition, it relates to a recombinant vector, in particular an expression vector, comprising said nucleic acid or expression cassette. Generally, an expression cassette comprises all the elements required for gene transcription and translation into a protein. In particular, it comprises a promoter, optionally an enhancer, a transcription terminator and the elements for translation. More particularly, the promoter used to control the expression of the NADPH-specific xylitol dehydrogenase is selected in order to drive a strong expression. Indeed, this enzyme is preferably overexpressed in the host cell. Such promoters are well-known in the art. For instance, the promoter could be the *P. ohmeri* ribulose reductase promoter (poRR) or the *P. ohmeri* phosphoglycerate kinase (poPGK1).

It relates to a recombinant vector, in particular an expression vector, comprising a nucleic acid encoding a NAD$^+$-specific D-arabitol 4-oxidoreductase and a nucleic acid encoding NADPH-specific xylitol dehydrogenase. It also relates to a kit comprising a recombinant vector, in particular an expression vector, comprising a nucleic acid encoding a NAD$^+$-specific D-arabitol 4-oxidoreductase, and a recombinant vector, in particular an expression vector, comprising a nucleic acid encoding NADPH-specific xylitol dehydrogenase.

Preferably, said NAD$^+$-specific D-arabitol 4-oxidoreductase and NADPH-specific xylitol dehydrogenase are selected among the enzymes disclosed above. In particular, said NAD$^+$-specific D-arabitol 4-oxidoreductase comprises or consists of an amino acid sequence of SEQ ID No 2 or 42 or a sequence with 1-3 additions, substitutions or deletions of amino acids. In particular, said NADPH-specific xylitol dehydrogenase comprises or consists of an amino acid sequence of SEQ ID No 5 or 8 or a sequence with 1-3 additions, substitutions or deletions of amino acids.

A preferred vector is a plasmid. Suitable plasmids are well-known by the person skilled in the art and can be for instance selected among those specifically disclosed in Examples.

Genetically modified host of the invention are first produced by cloning the genes coding for NAD$^+$-specific D-arabitol 4-oxidoreductase and for NADPH-specific xylitol dehydrogenase under control of suitable promoters into a recombinant vector and introduced into the host cells of the D-arabitol producing organism by transformation.

The present invention relates to a recombinant or genetically engineering host cell comprising an heterologous nucleic acid sequence encoding a NAD specific D-arabitol 4-oxidoreductase (EC 1.1.1.11) and an heterologous nucleic acid sequence encoding a NADPH-specific xylitol dehydrogenase. The NAD$^+$-specific D-arabitol 4-oxidoreductase uses D-arabitol as substrate and produces D-xylulose as product. The NADPH-specific xylitol dehydrogenase uses D-xylulose as substrate and produces xylitol. The sequence encoding NADPH-specific xylitol dehydrogenase and NAD$^+$-specific D-arabitol 4-oxidoreductase can be episomal or be integrated into the chromosome of the host cell. Indeed, genetically stable transformants are preferably constructed through transformation systems using a vector, whereby a desired DNA is integrated into the host chromosome. Such integration occurs de novo within the cell or can be assisted by transformation with a vector which functionally inserts itself into the host chromosome, with DNA elements which promote integration of DNA sequences in chromosomes.

The recombinant or genetically engineering host cell can comprise several copies of a sequence encoding a NAD$^+$-specific D-arabitol 4-oxidoreductase and/or several copies of a sequence encoding the NADPH-specific xylitol dehydrogenase, preferably integrated into the host cell chromosome. In particular, the recombinant or genetically engineering host cell can comprise two, three or four sequences encoding a NAD$^+$-specific D-arabitol 4-oxidoreductase and/or two, three or four sequences encoding the NADPH-specific xylitol dehydrogenase. For instance, the host cell may comprise two or three NAD$^+$-specific D-arabitol 4-oxidoreductases from *E. coli* and/or one or two NAD$^+$-specific D-arabitol 4-oxidoreductases from *R. solanacearum*, more specifically two or three NAD$^+$-specific D-arabitol 4-oxidoreductases from *E. coli* and/or one NAD$^+$-specific D-arabitol 4-oxidoreductase from *R. solanacearum*. The NAD$^+$-specific D-arabitol 4-oxidoreductases can be from the same organism or from different organisms. The NADPH-specific xylitol dehydrogenases can be from the same organism or from different organisms. For instance, the host cell may comprise one, two or three NADPH-specific xylitol dehydrogenases from *P. stipitis* and/or one, two or three NADPH-specific xylitol dehydrogenases from *G. oxydans*, more specifically one NADPH-specific xylitol dehydrogenase from *P. stipitis* and/or three NADPH-specific xylitol dehydrogenases from *G. oxydans*.

In a particular aspect of the invention, the recombinant or genetically engineering host cell is a *Pichia ohmeri* strain comprising:
  two NAD$^+$-specific D-arabitol 4-oxidoreductases and two NADPH-specific xylitol dehydrogenases; or
  two NAD$^+$-specific D-arabitol 4-oxidoreductases from *E. coli* and two NADPH-specific xylitol dehydrogenases, one from *P. stipitis* and the other from *G. oxydans*; or
  two NAD$^+$-specific D-arabitol 4-oxidoreductases and three NADPH-specific xylitol dehydrogenases; or
  two NAD$^+$-specific D-arabitol 4-oxidoreductases from *E. coli* and three NADPH-specific xylitol dehydrogenases, one from *P. stipitis* and two from *G. oxydans*; or
  three NAD$^+$-specific D-arabitol 4-oxidoreductases and three NADPH-specific xylitol dehydrogenases; or
  three NAD$^+$-specific D-arabitol 4-oxidoreductases, two from *E. coli* and one from *R. solanacearum*, and three NADPH-specific xylitol dehydrogenases, one from *P. stipitis* and two from *G. oxydans*; or four NAD+-specific D-arabitol 4-oxidoreductases and four NADPH-specific xylitol dehydrogenases; or four NAD+-specific D-arabitol 4-oxidoreductases, three from *E. coli* and one from *R. solanacearum*, and four NADPH-specific xylitol dehydrogenases, one from *P. stipitis* and three from *G. oxydans*.

The host cell is selected among the microorganisms detailed above. In a preferred embodiment, the host cell is *Pichia ohmeri*. The starting host cell is preferably the mutant *Pichia ohmeri* deposited at the CNCM under number I-4605.

In a particular aspect of the invention, the host cell is a strain selected from strains I-4982, I-4960 and I-4981 deposited at the CNCM.

The present invention relates to a method for producing xylitol comprising culturing the recombinant or genetically engineering host cell in a culture medium and recovering the produced xylitol. Preferably, the culture medium provides the microorganism with the convenient carbon source. The carbon source preferably includes D-glucose, and various D-glucose-containing syrups and mixtures of D-glucose with other sugars. The method may further comprises a step of purifying xylitol.

The present invention relates to the use of a recombinant or genetically engineering host cell as disclosed herein for producing xylitol.

Xylitol produced by such genetically modified strains can be purified from the medium of the hosts of the invention according to any technique known in the art. For example, U.S. Pat. No. 5,081,026, incorporated herein by reference, described the chromatographic separation of xylitol from yeast cultures. Thus, from the fermentation step, xylitol can be purified from the culture medium using chromatographic steps as described in U.S. Pat. No. 5,081,026, followed by crystallization.

Other characteristic features and advantages of the invention will be apparent on reading the following Examples. However, they are given here only as an illustration and are not limiting.

FIGURES AND SEQUENCES

FIG. 1: 12 ABYWMP: Restriction map of the synthesized NAD+-specific D-arabitol 4-oxidoreductase from *E. coli* flanked by AscI and SphI restriction sites.

Figure 2A:
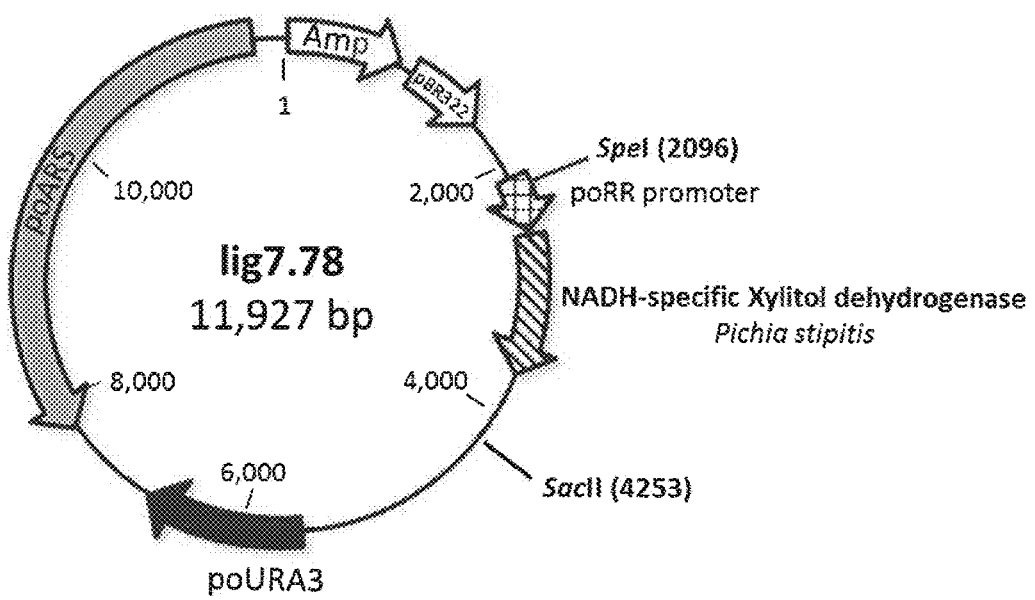

FIG. 2A: lig7.78: Restriction map of the NADH-specific xylitol dehydrogenase from *Pichia stipitis*.

Figure 2B:
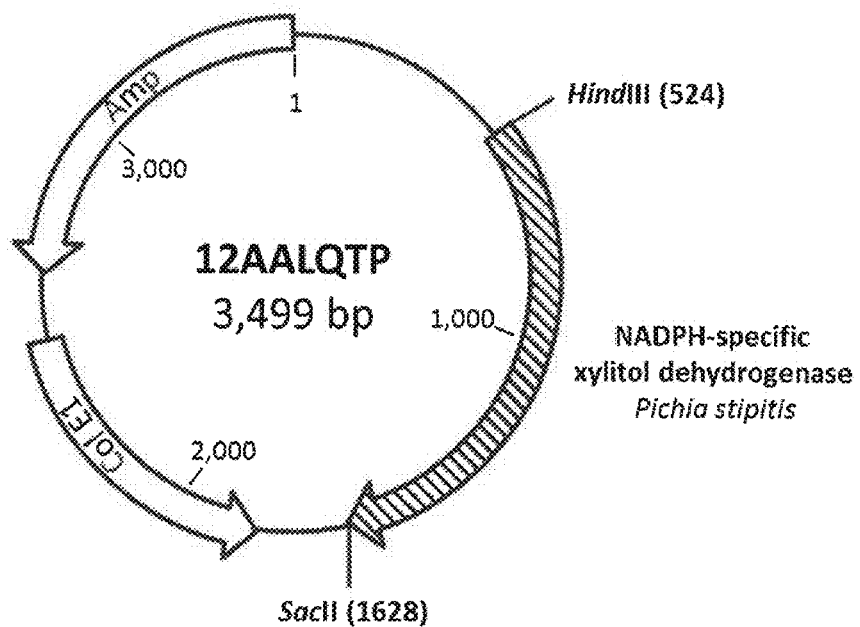

FIG. 2B: 12AALQTP: Restriction map of the synthesized NADPH-specific xylitol dehydrogenase from *Pichia stipitis* flanked by HindIII and SacII restriction sites.

Figure 3:
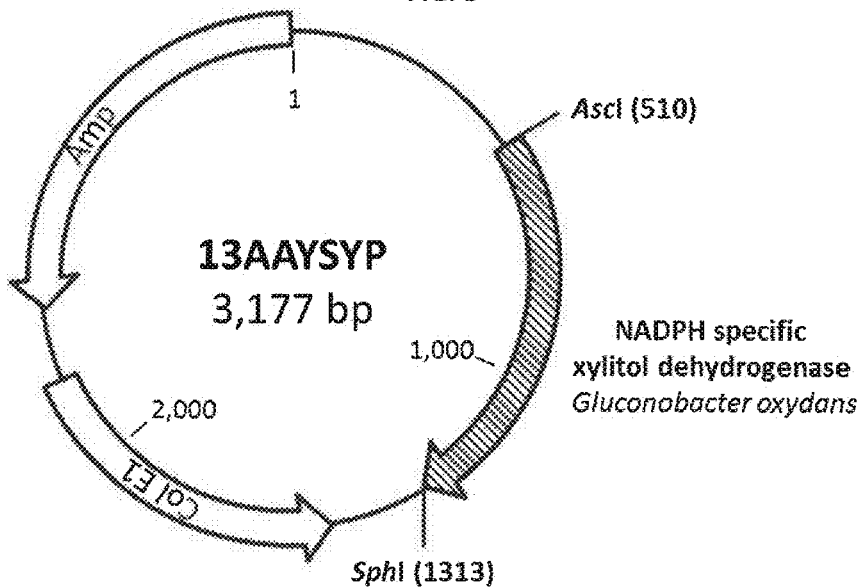

FIG. 3: 13AAYSYP: Restriction map of the synthesized NADPH-specific xylitol dehydrogenase from *Gluconobacter oxydans* flanked by AscI and SphI restriction sites.

Figure 4:
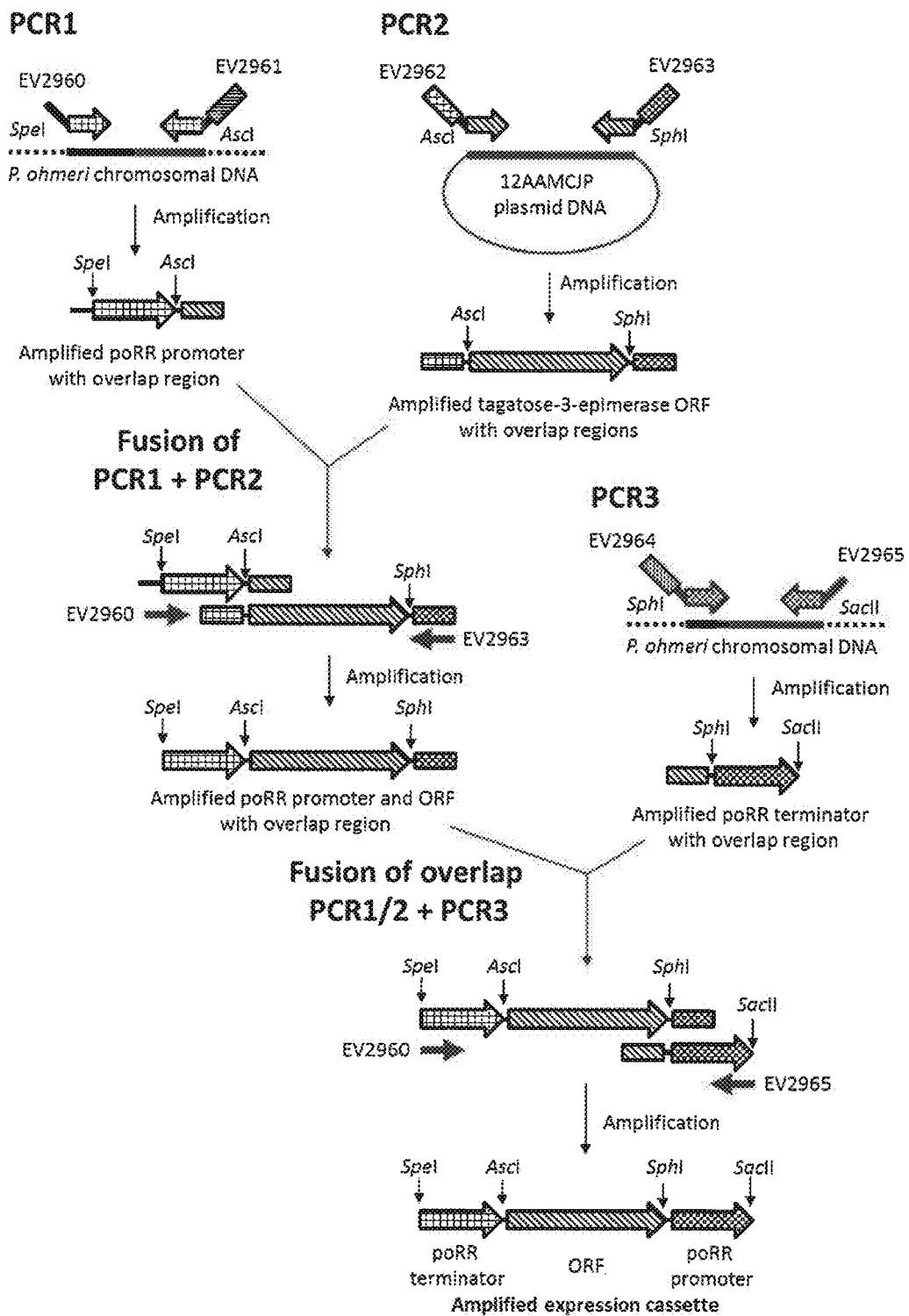

FIG. 4: Construction of an expression cassette consisting of an open reading frame flanked by a poRR promoter and terminator using overlap PCR.

Figure 5:
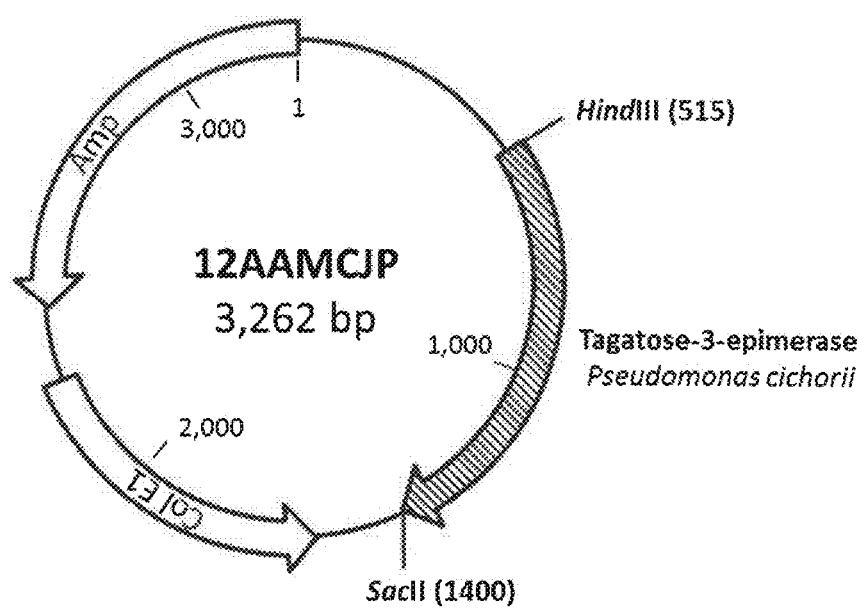

FIG. 5: 12 AAMCJP: Restriction map of the synthesized tagatose-3-epimerase of *Pseudomonas cichorii* flanked by HindIII and SacII restriction sites.

Figure 6:
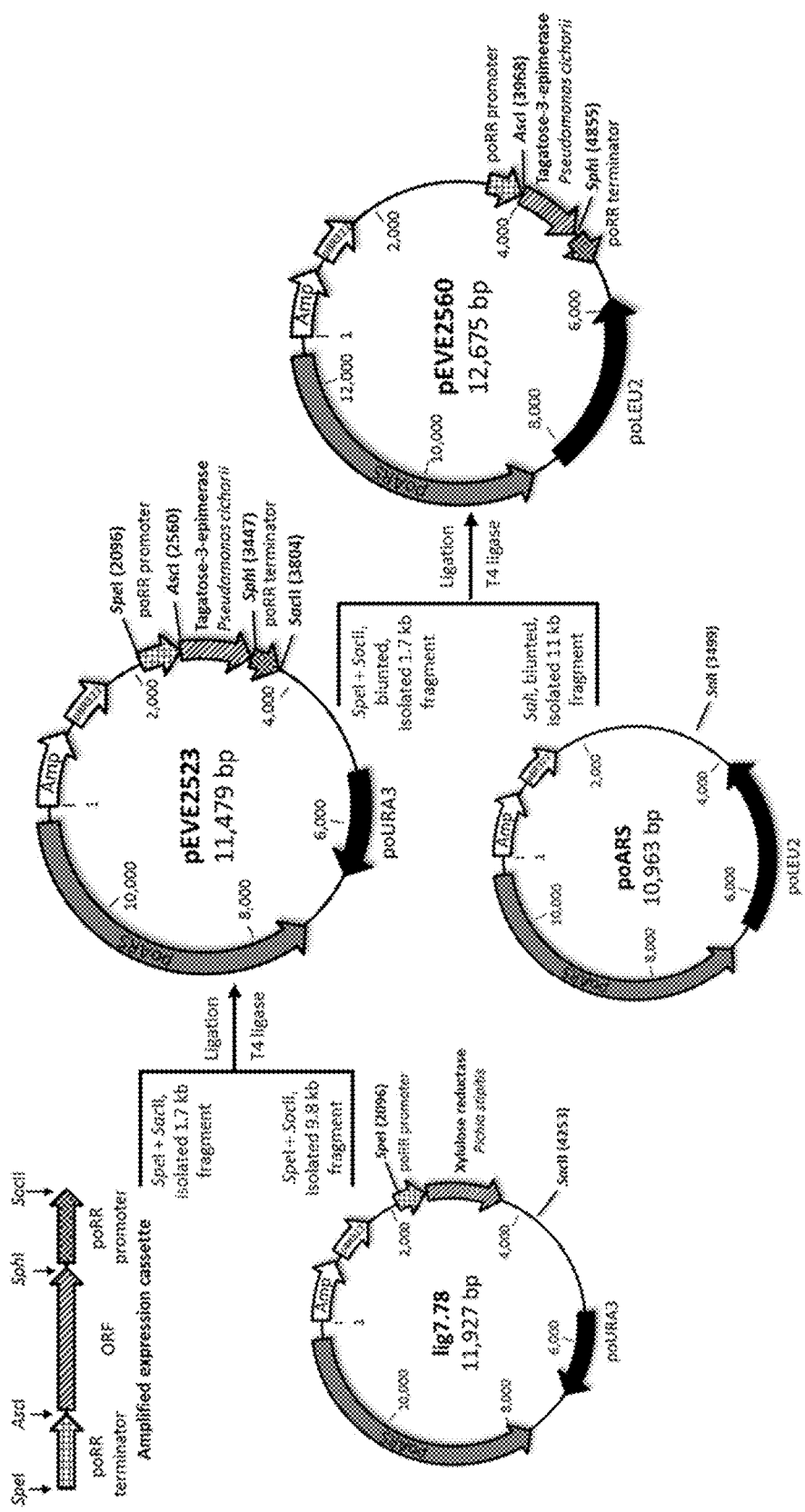

FIG. 6: Construction of *P. ohmeri* shuttle vectors with poLEU2 and poURA3 selection markers.

Figure 7:
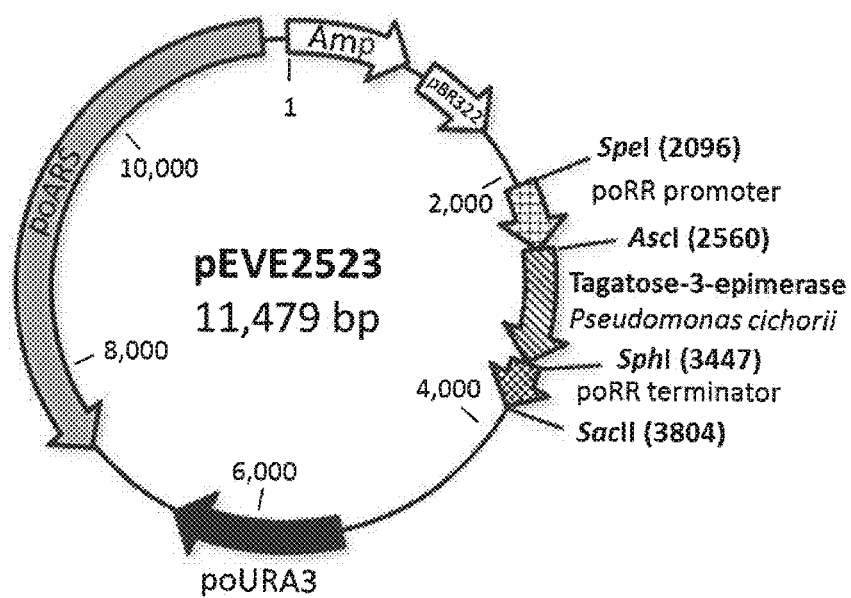

FIG. 7: pEVE2523: Restriction map of the *P. ohmeri* poURA3 expression vector pEVE2523, with a cloned expression cassette containing the open reading frame of tagatose-3-epimerase of *Pseudomonas cichorii* flanked by a *P. ohmeri* ribulose reductase (poRR) promoter and terminator.

Figure 8:
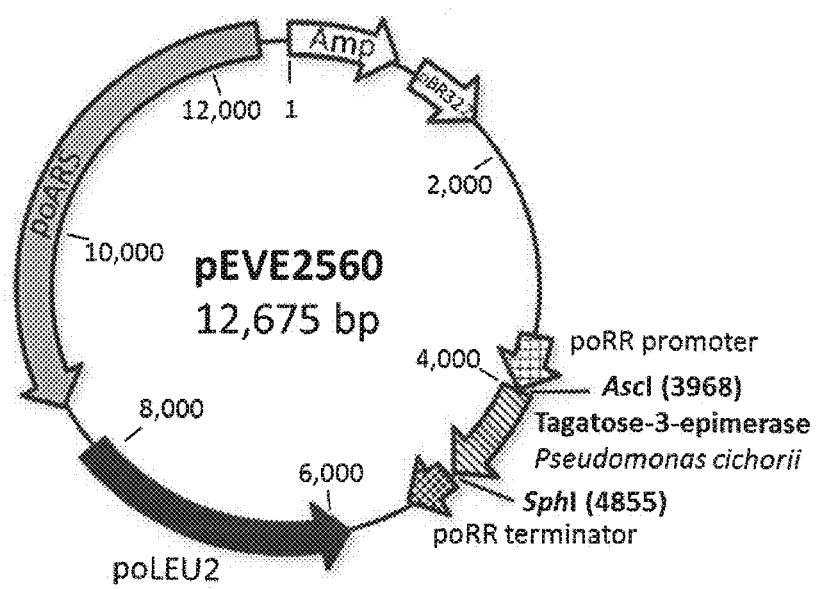

FIG. 8: pEVE2560: Restriction map of the *P. ohmeri* poLEU2 expression vector pEVE2560, with a cloned expression cassette containing the open reading frame of tagatose-3-epimerase of *Pseudomonas cichorii* flanked by a *P. ohmeri* ribulose reductase (poRR) promoter and terminator.

Figure 9:
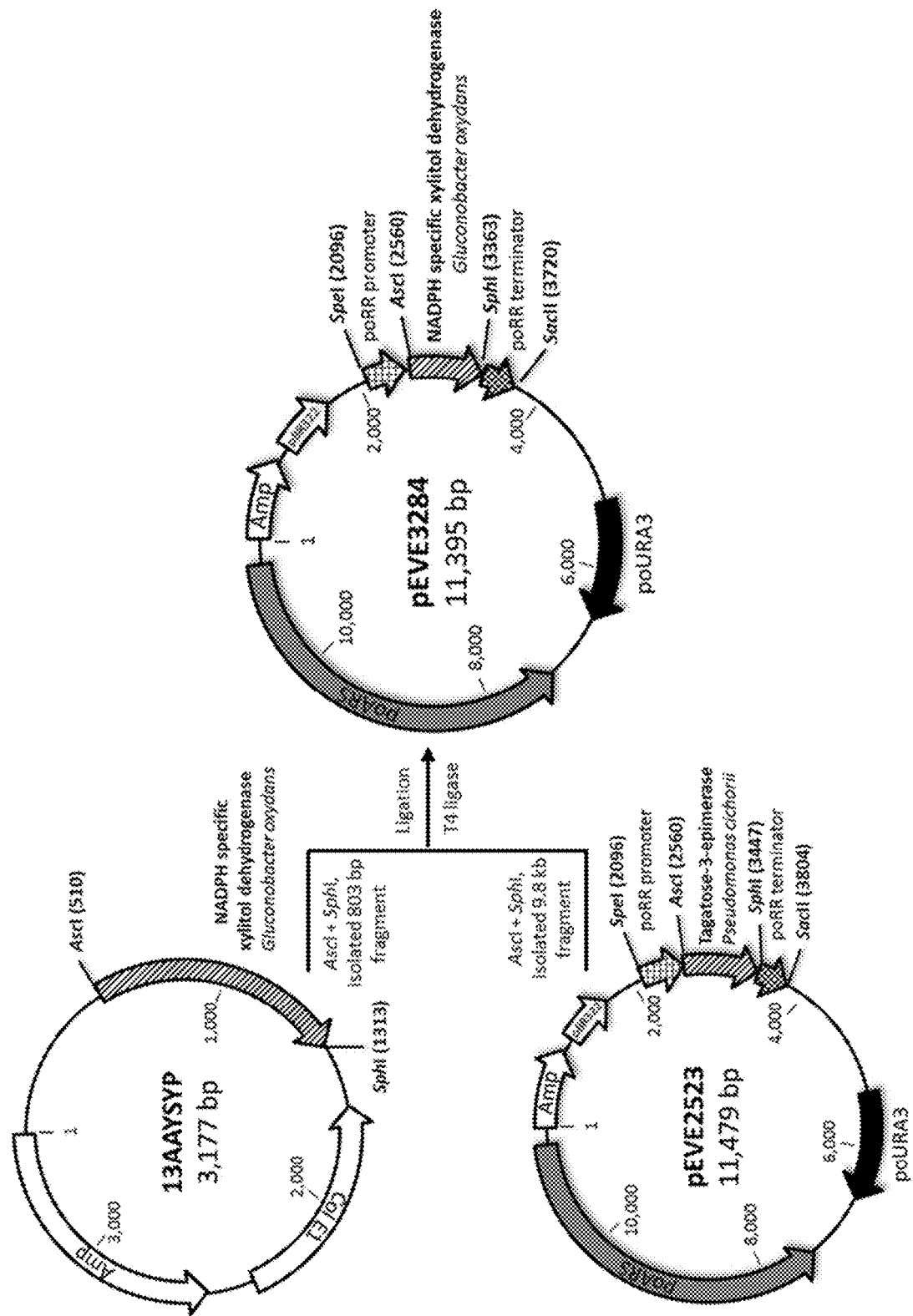

FIG. 9: Construction of a *P. ohmeri* vector for overexpression of *Gluconobacter oxydans* NADPH-specific xylitol dehydrogenase.

Figure 10:
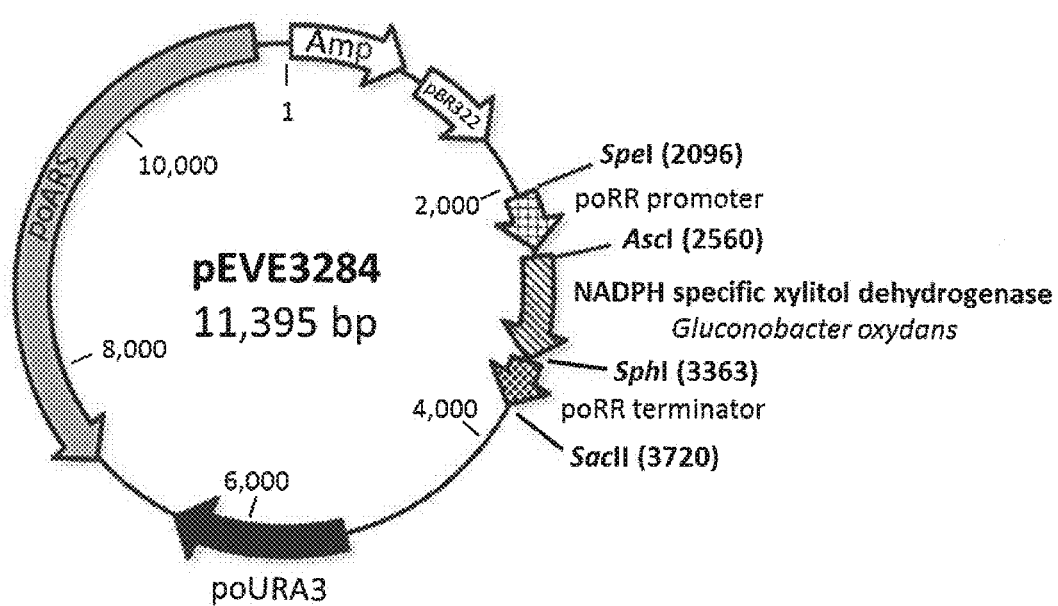

FIG. 10: pEVE3284: Restriction map of the *P. ohmeri* pEVE3284 expression vector, with a cloned expression cassette containing the NADPH-specific xylitol dehydrogenase of *Gluconobacter oxydens* flanked by a *P. ohmeri* ribulose reductase (poRR) promoter and terminator.

Figure 11:
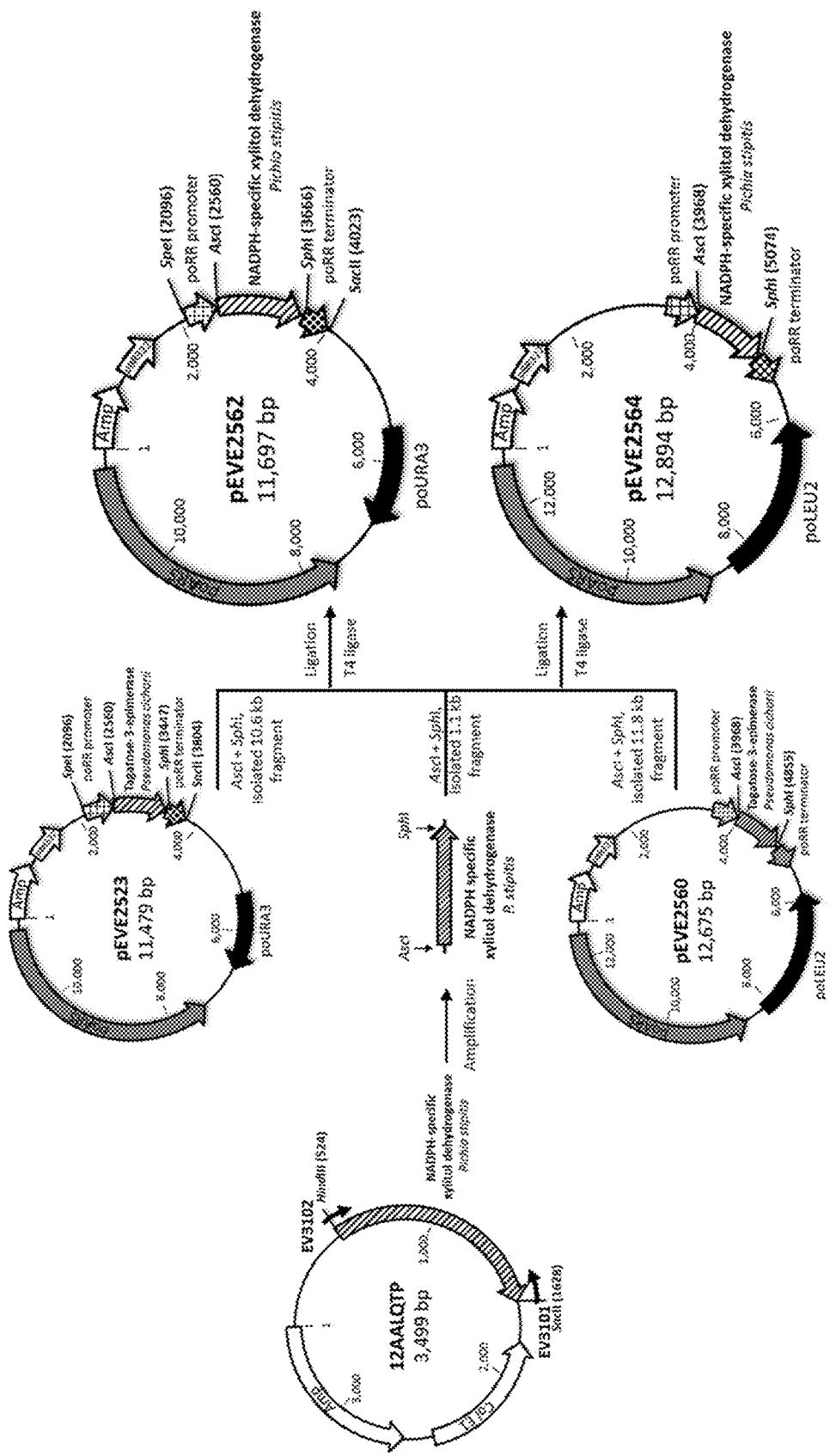

FIG. 11: Construction of a *P. ohmeri* vectors for overexpression of *Pichia stipitis* NADPH-specific xylitol dehydrogenase.

Figure 12:
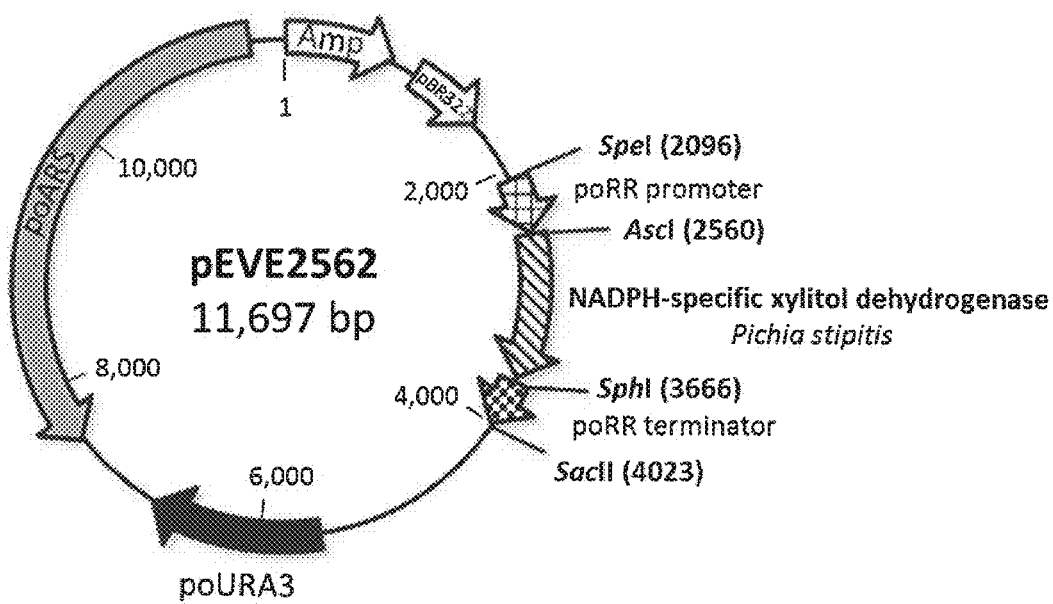
Figure 12:
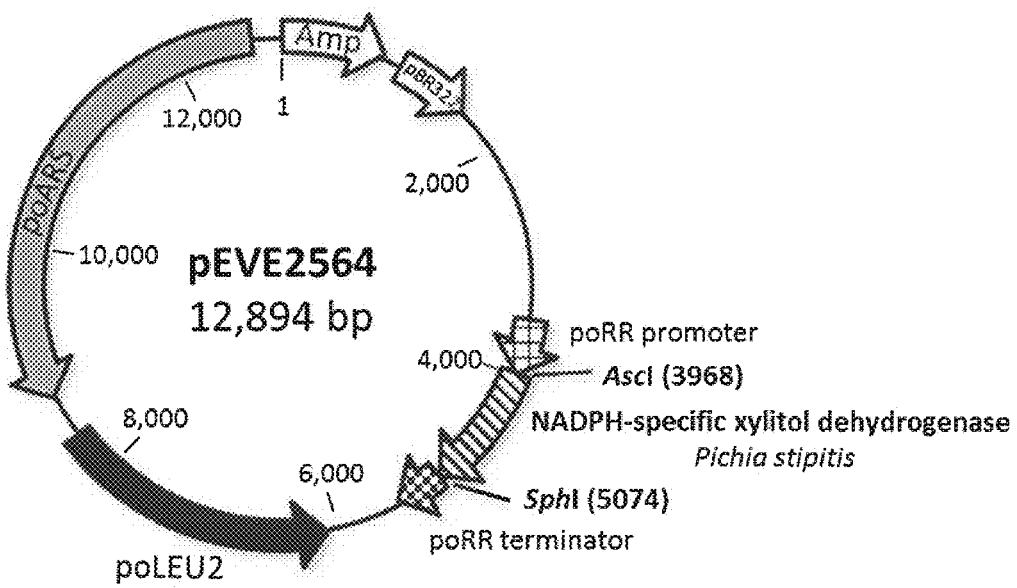

FIG. 12: pEVE2562/pEVE2564: Restriction map of the *P. ohmeri* pEVE2562/pEVE2564 expression vectors, with a cloned expression cassette containing the NADPH-specific xylitol dehydrogenase of *Pichia stipitis* flanked by a *P. ohmeri* ribulose reductase (poRR) promoter and terminator with either a poURA3 or poLEU2 selection marker, respectively.

Figure 13:
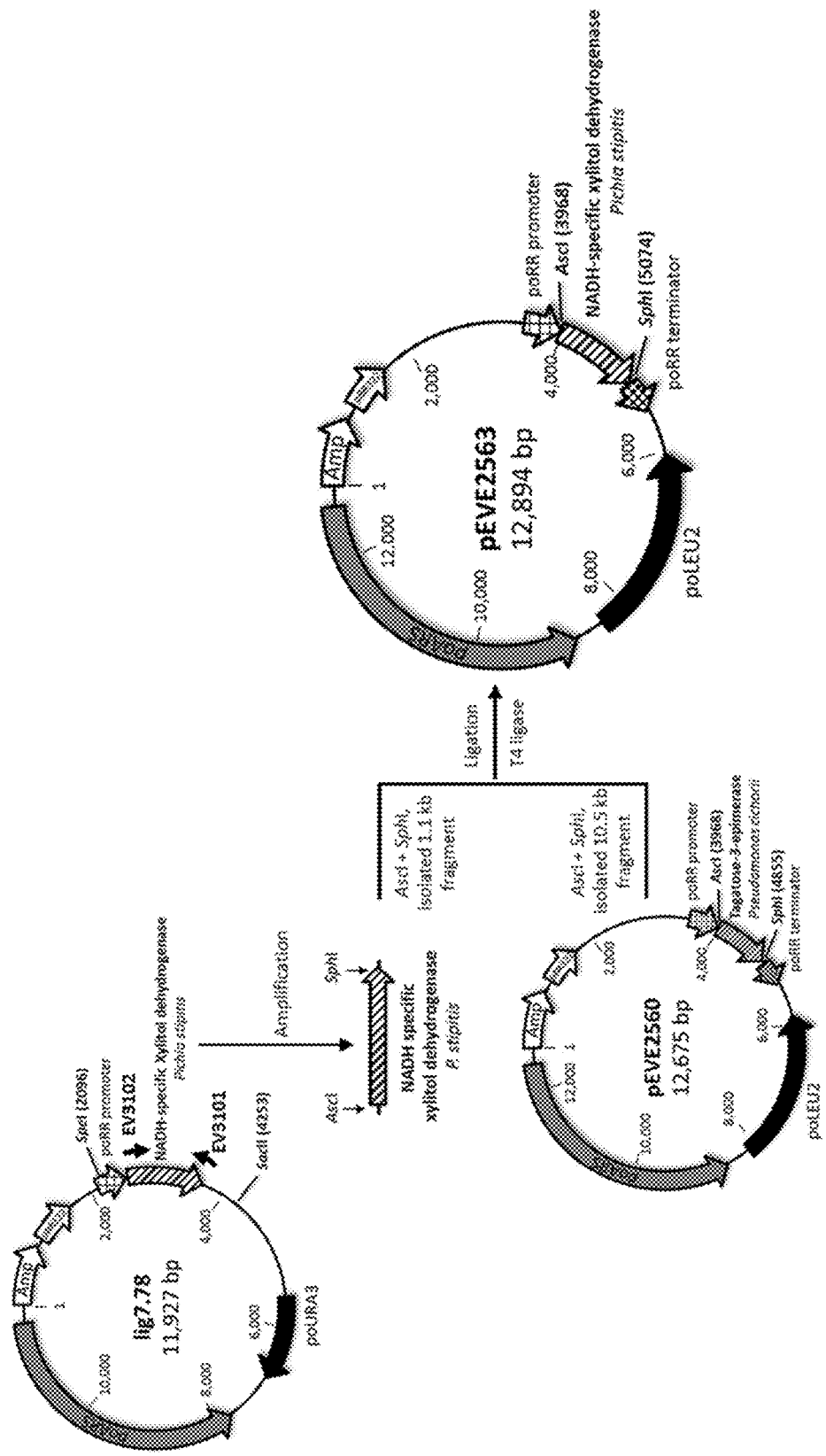

FIG. 13: Construction of a *P. ohmeri* vector for overexpression of *Pichia stipitis* NADH-specific xylitol dehydrogenase.

Figure 14:
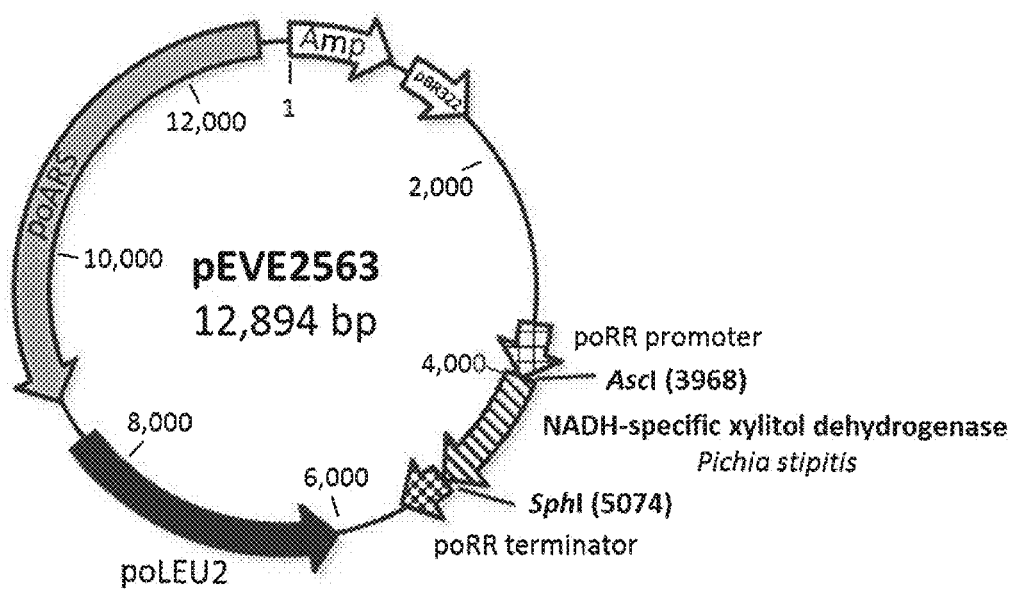

FIG. 14: pEVE2563: Restriction map of the *P. ohmeri* pEVE2563 expression vector, with a cloned expression cassette containing the NADH-specific xylitol dehydrogenase of *Pichia stipitis* flanked by a *P. ohmeri* ribulose reductase (poRR) promoter and terminator.

Figure 15:
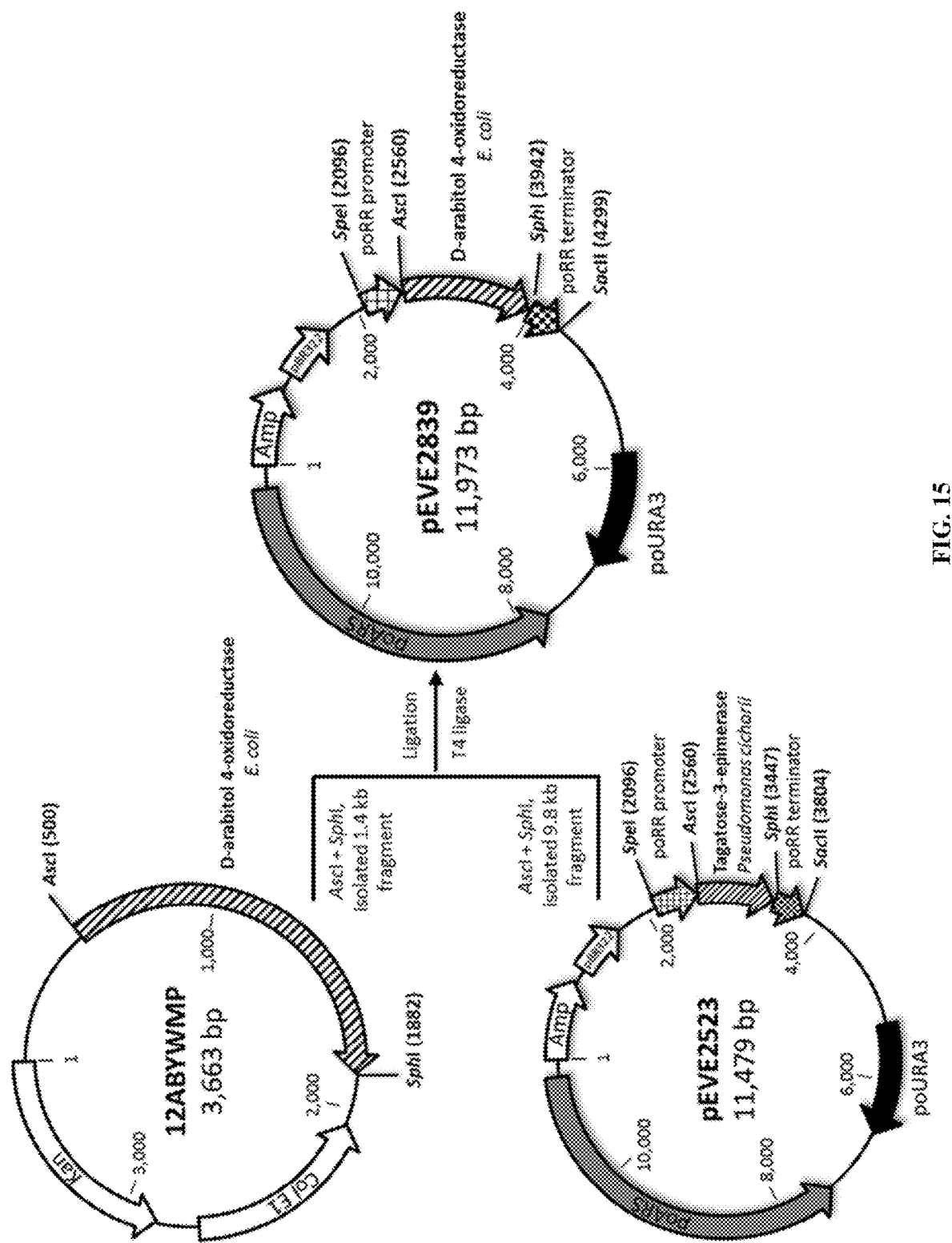

FIG. 15: Construction of a *P. ohmeri* vector for overexpression of *E. coli* NAD+-specific D-arabitol 4-oxidoreductase under the control of the *P. ohmeri* ribulose reductase (poRR) promoter and terminator using a poURA3 selection marker.

Figure 16:
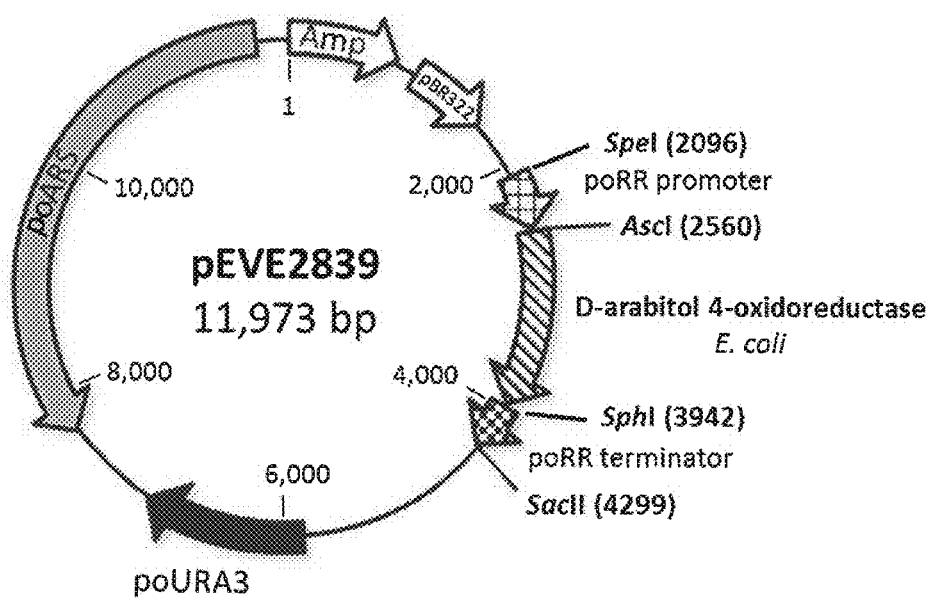

FIG. 16: pEVE2839: Restriction map of the *P. ohmeri* pEVE2839 expression vector, with a cloned expression cassette containing the NAD+-specific D-arabitol 4-oxidoreductase of *E. coli* flanked by a *P. ohmeri* ribulose reductase (poRR) promoter and terminator.

Figure 17:
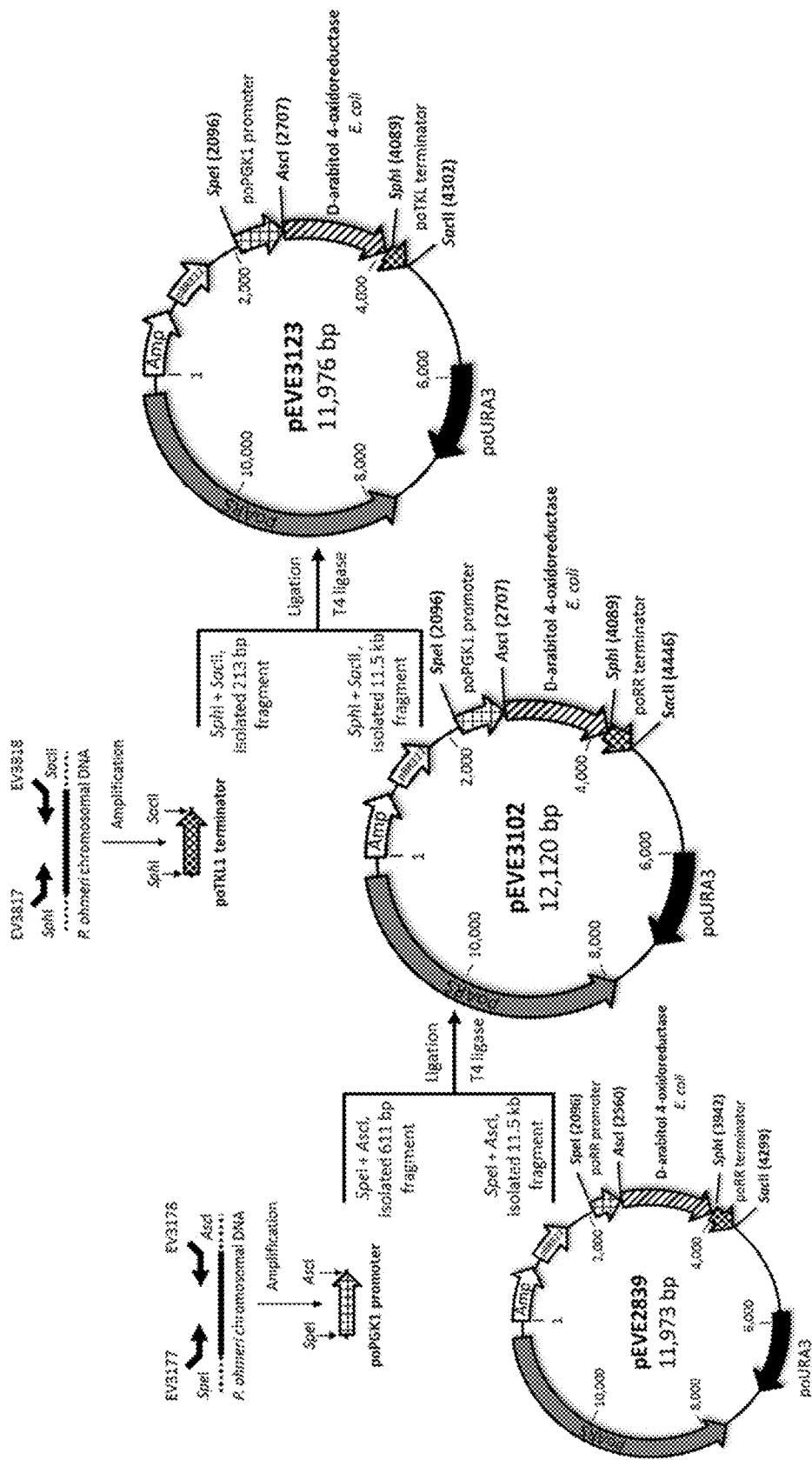

FIG. 17: Construction of a *P. ohmeri* vector for overexpression of *E. coli* NAD+-specific D-arabitol 4-oxidoreductase under the control of the *P. ohmeri* phophoglycerate kinase (poPGK1) promoter and transketolase (poTKL) terminator using a poURA3 selection marker.

Figure 18:
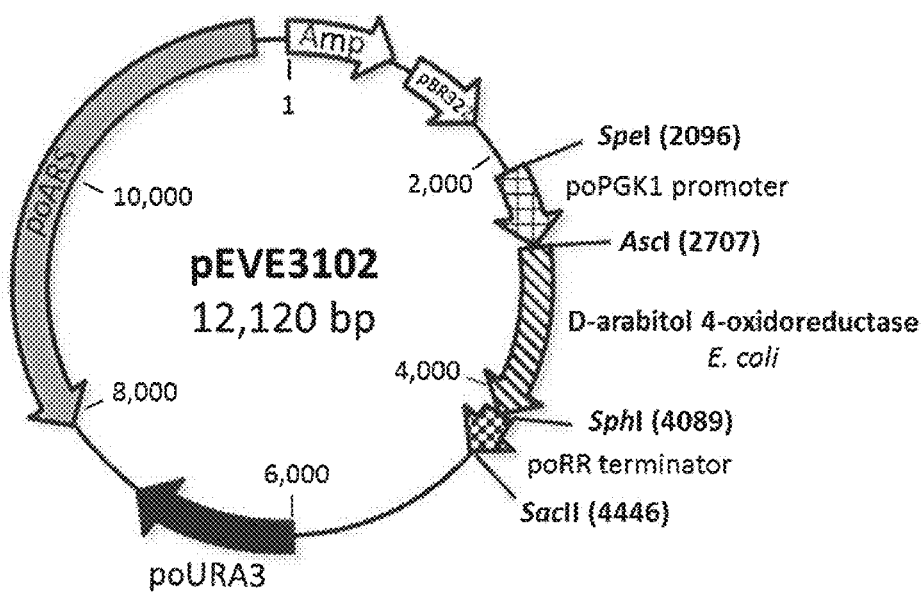

FIG. 18: pEVE3102: Restriction map of the *P. ohmeri* pEVE3102 expression vector, with a cloned expression cassette containing the NAD+-specific D-arabitol 4-oxidoreductase of *E. coli* flanked by a *P. ohmeri* phosphoglycerate kinase (poPGK1) promoter and ribulose reductase (poRR) terminator.

Figure 19:
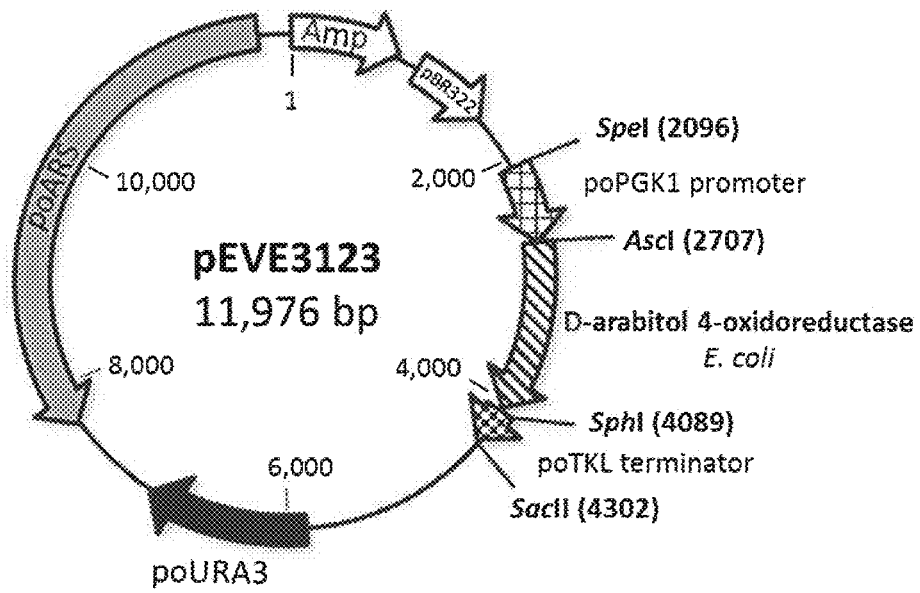

FIG. 19: pEVE3123: Restriction map of the *P. ohmeri* pEVE3123 expression vector, with a cloned expression cassette containing the NAD+-specific D-arabitol oxidoreductase of *E. coli* flanked by a *P. ohmeri* phosphoglycerate kinase (poPGK1) promoter and a transketolase (poTKL) terminator and a poURA3 selection marker.

Figure 20:
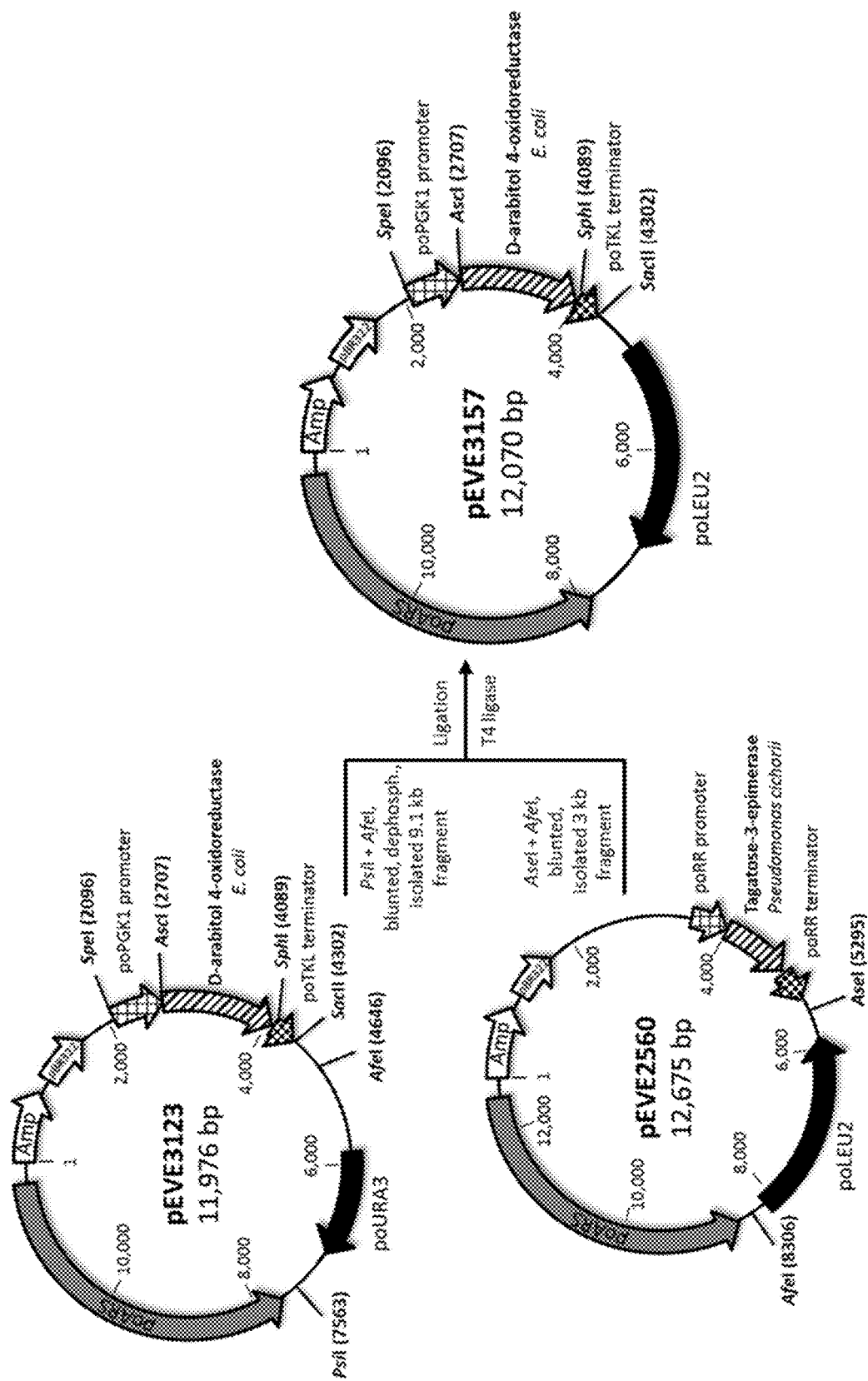

FIG. 20: Construction of a *P. ohmeri* vector for overexpression of *E. coli* NAD+-specific D-arabitol 4-oxidoreductase under the control of the *P. ohmeri* phosphoglycerate kinase (poPGK1) promoter and transketolase (poTKL) terminator using a poLEU2 selection marker.

Figure 21:
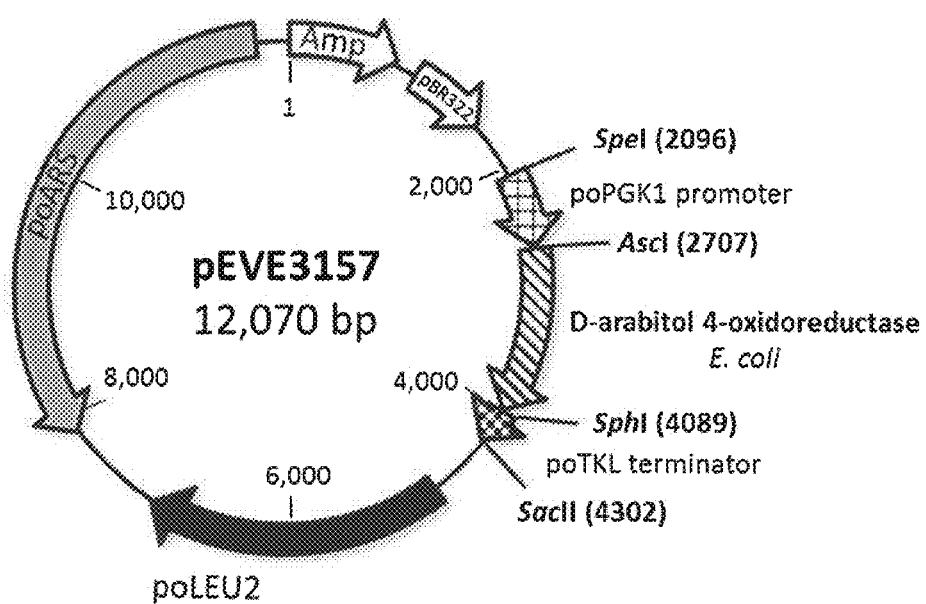

FIG. 21: pEVE3157: Restriction map of the *P. ohmeri* pEVE3157 expression vector, with a cloned expression cassette containing the NAD+-specific D-arabitol 4-oxidoreductase of *E. coli* flanked by a *P. ohmeri* phosphoglycerate kinase (poPGK1) promoter and a transketolase (poTKL) terminator and a poLEU2 selection marker.

Figure 22:
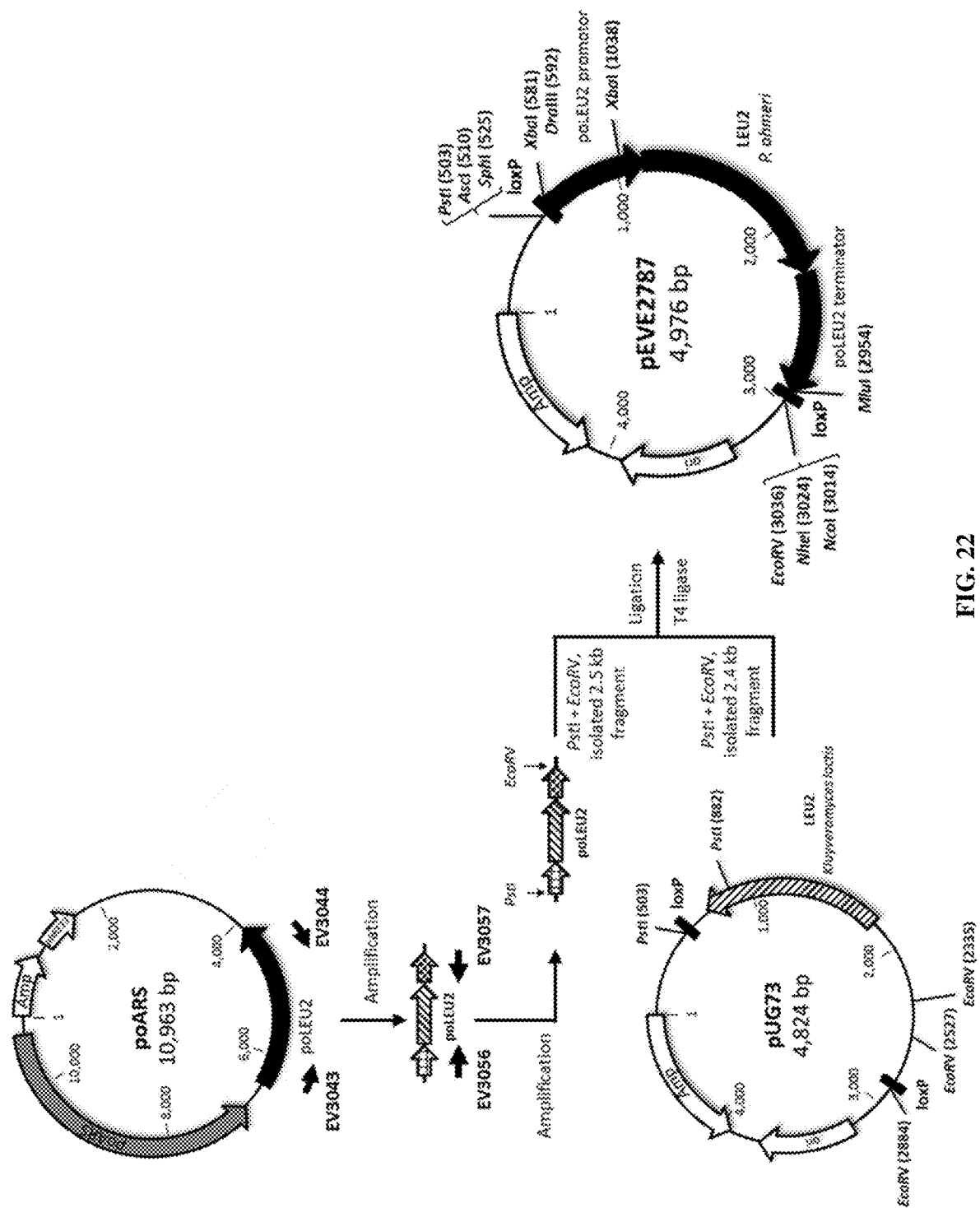
Figure 23:
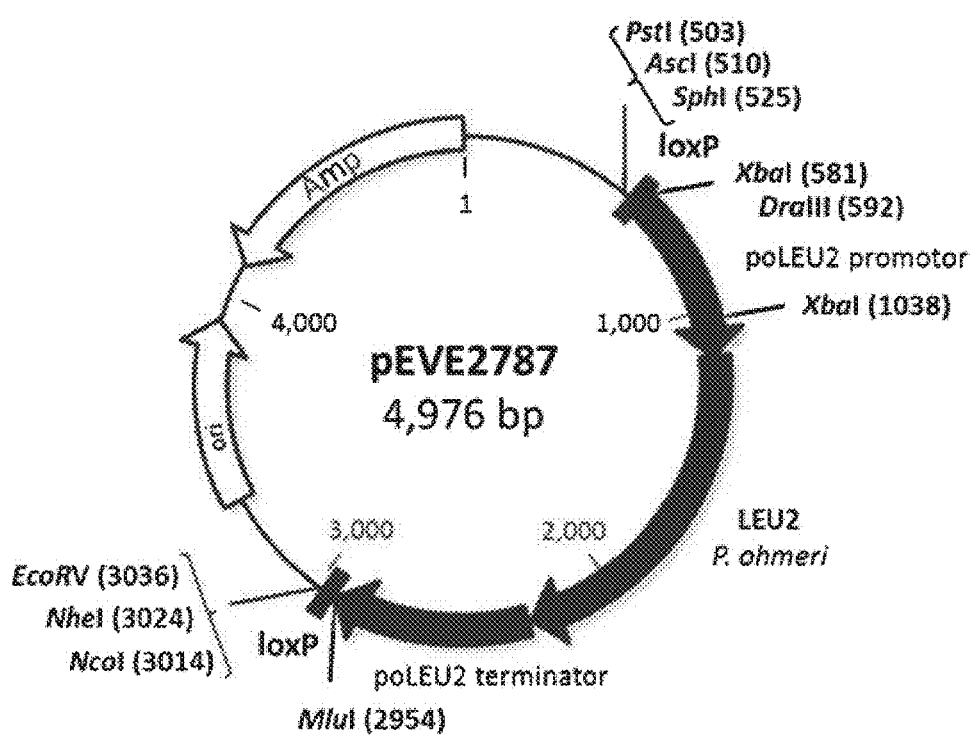

FIG. 22: Construction of a *P. ohmeri* loxP vector with a poLEU2 selection marker FIG. 23: pEVE2787: Restriction map of the *P. ohmeri* pEVE2787 integration vector, with a cloned *P. ohmeri* LEU2 selection marker under the control of the endogenous promoter and terminator, flanked by two loxP sites.

Figure 24:
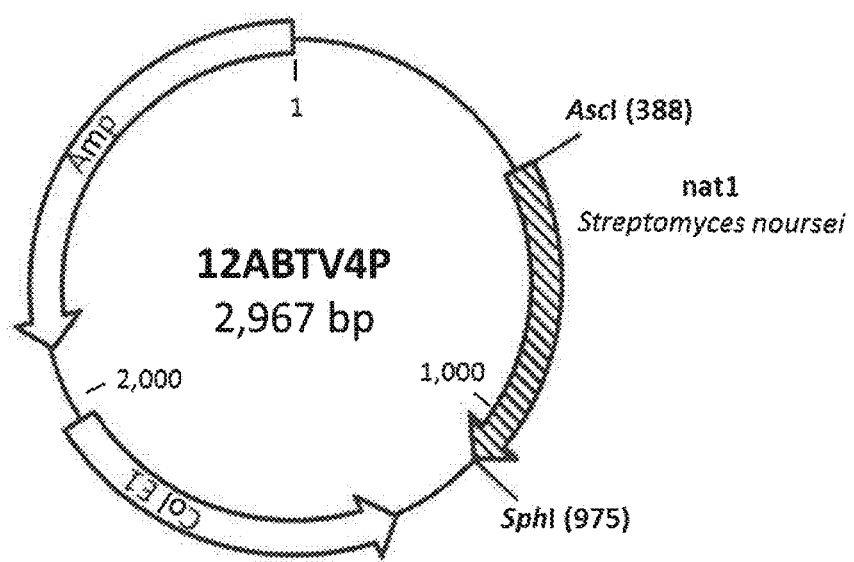

FIG. 24: 12ABTV4P: Restriction map of the synthesized nat1 gene from *Streptomyces noursei* flanked by AscI and SphI restriction sites.

Figure 25:
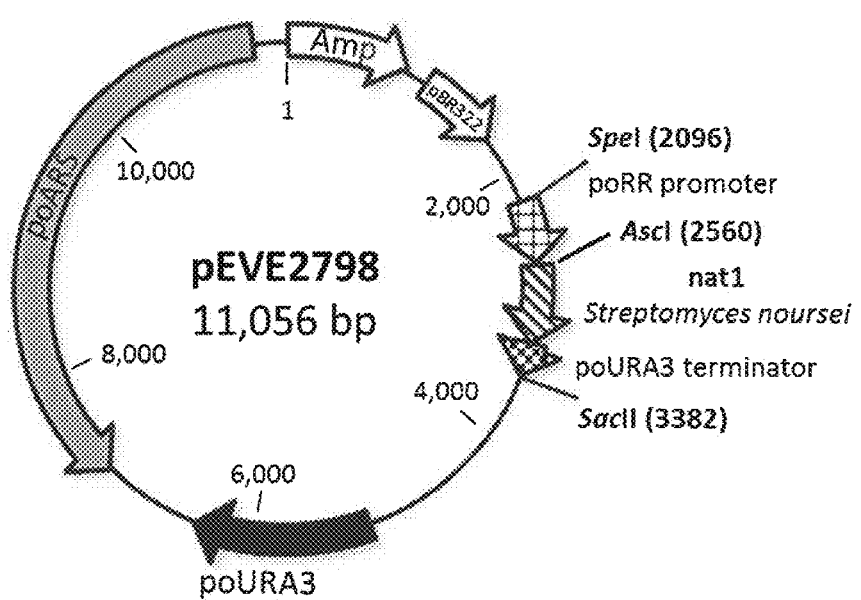

FIG. 25: pEVE2798: Restriction map of the *P. ohmeri* pEVE2798 expression vector, with a cloned nat1 marker under the control of a ribulose reductase (poRR) promoter and an orotidine-5'-phosphate decarboxylase (poURA3) terminator.

Figure 26:
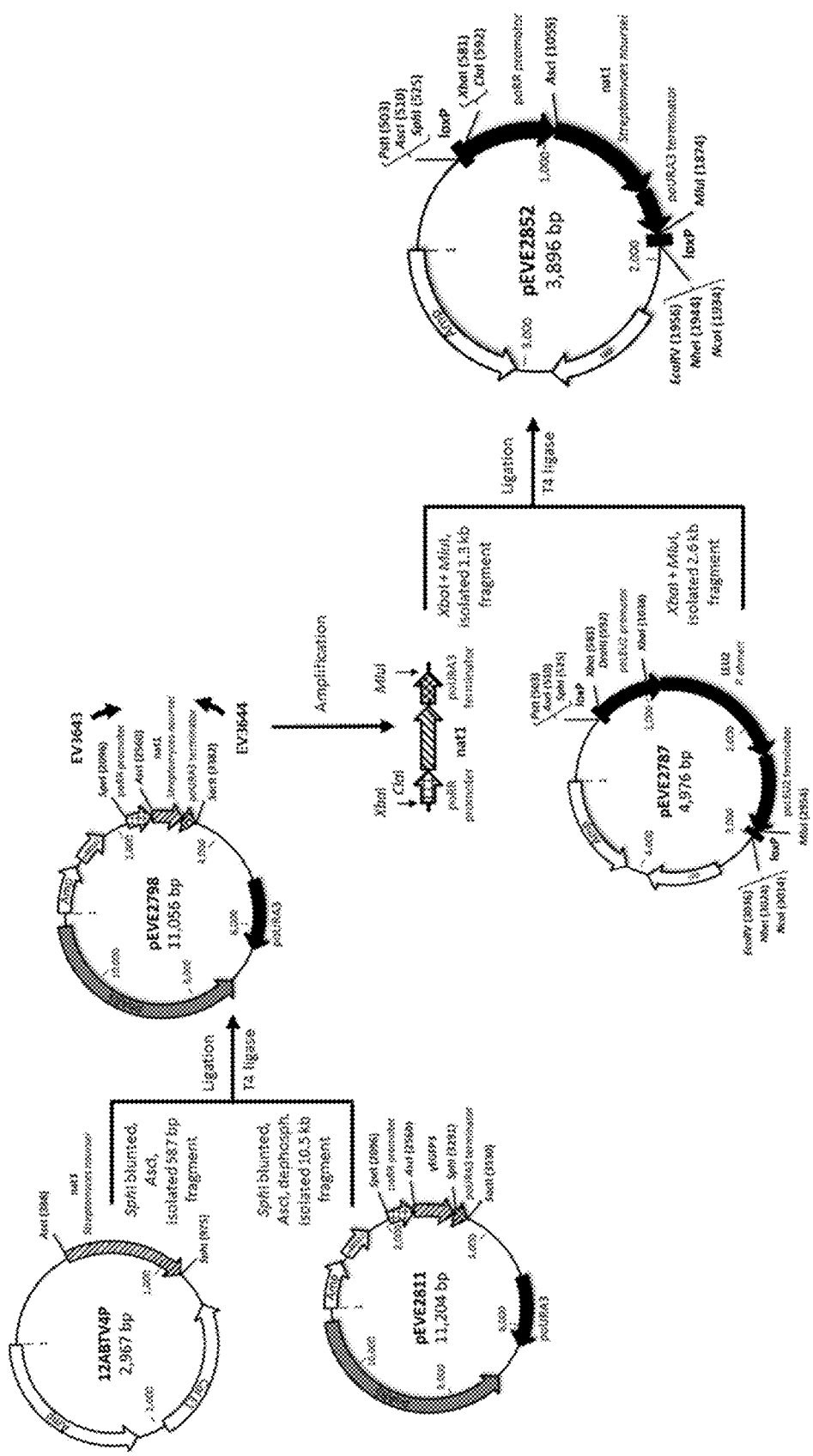

FIG. 26: Construction of a *P. ohmeri* loxP vector with a nat1 selection marker.

Figure 27:
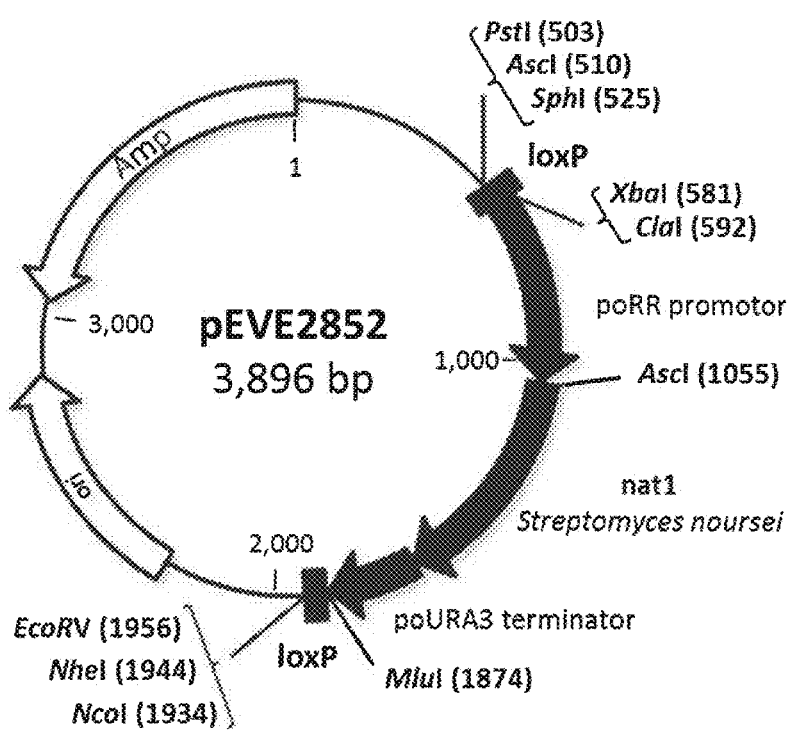

FIG. 27: pEVE2852: Restriction map of the *P. ohmeri* pEVE2852 integration vector, with a cloned with a cloned nat1 marker under the control of a ribulose reductase (poRR) promoter and an orotidine-5'-phosphate decarboxylase (poURA3) terminator, flanked by two loxP sites.

Figure 28:
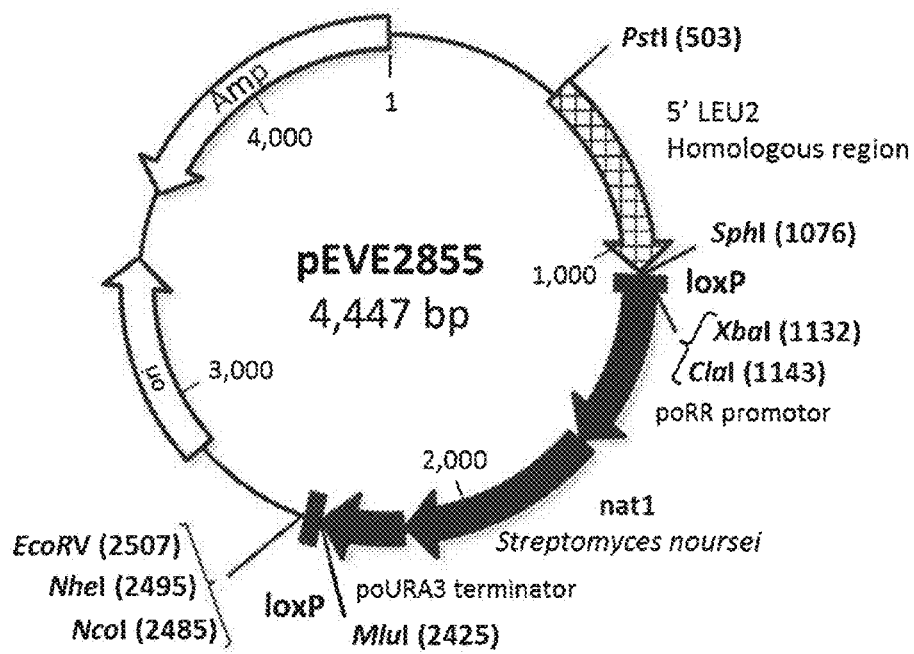

FIG. 28: pEVE2855: Restriction map of the *P. ohmeri* pEVE2855 integration vector, with a cloned fragment homologous to the 5' region upstream of the LEU2 open reading frame and a nat1 selection marker flanked by two loxP sites.

Figure 29:
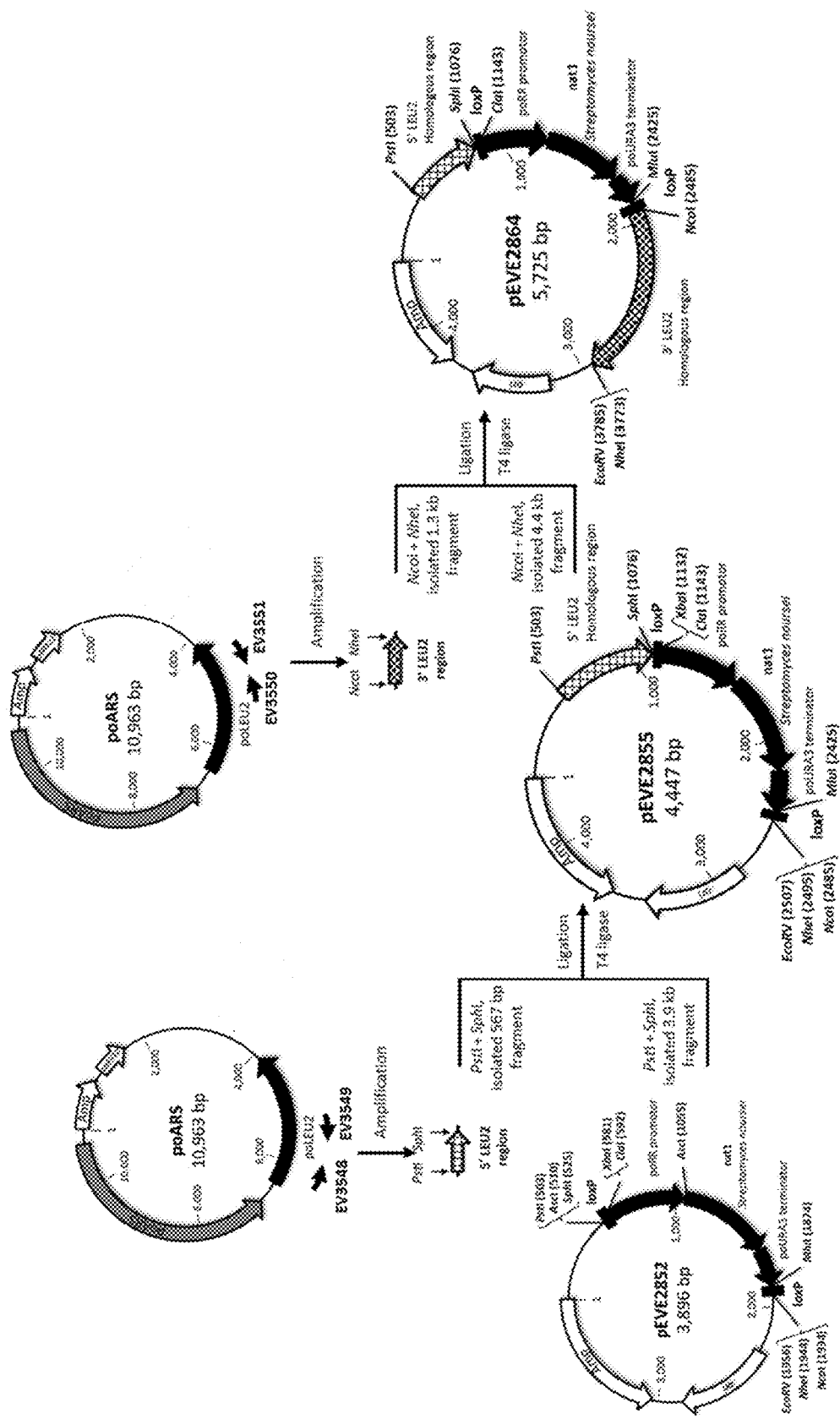

FIG. 29: Construction of a *P. ohmeri* loxP vector for the deletion of the LEU2 open reading frame.

Figure 30:
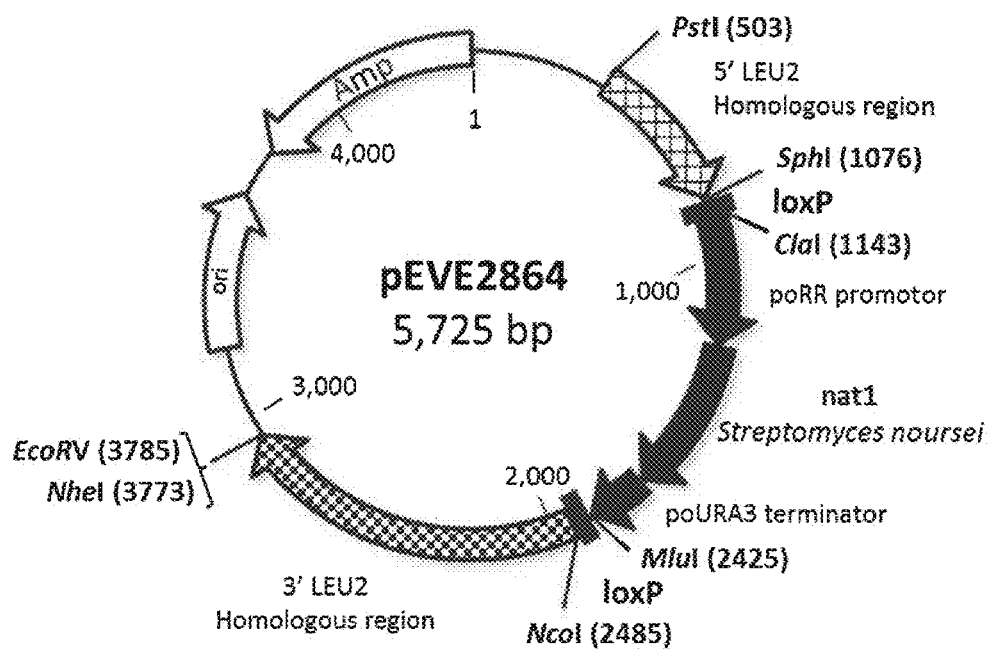

FIG. 30: pEVE2864: Restriction map of the *P. ohmeri* pEVE2864 integration vector, with a cloned fragment homologous to the 5' region upstream of the LEU2 open reading frame and fragment homologous to the 3' region downstream of the LEU2 open reading frame, and a nat1 selection marker flanked by two loxP sites.

Figure 31:
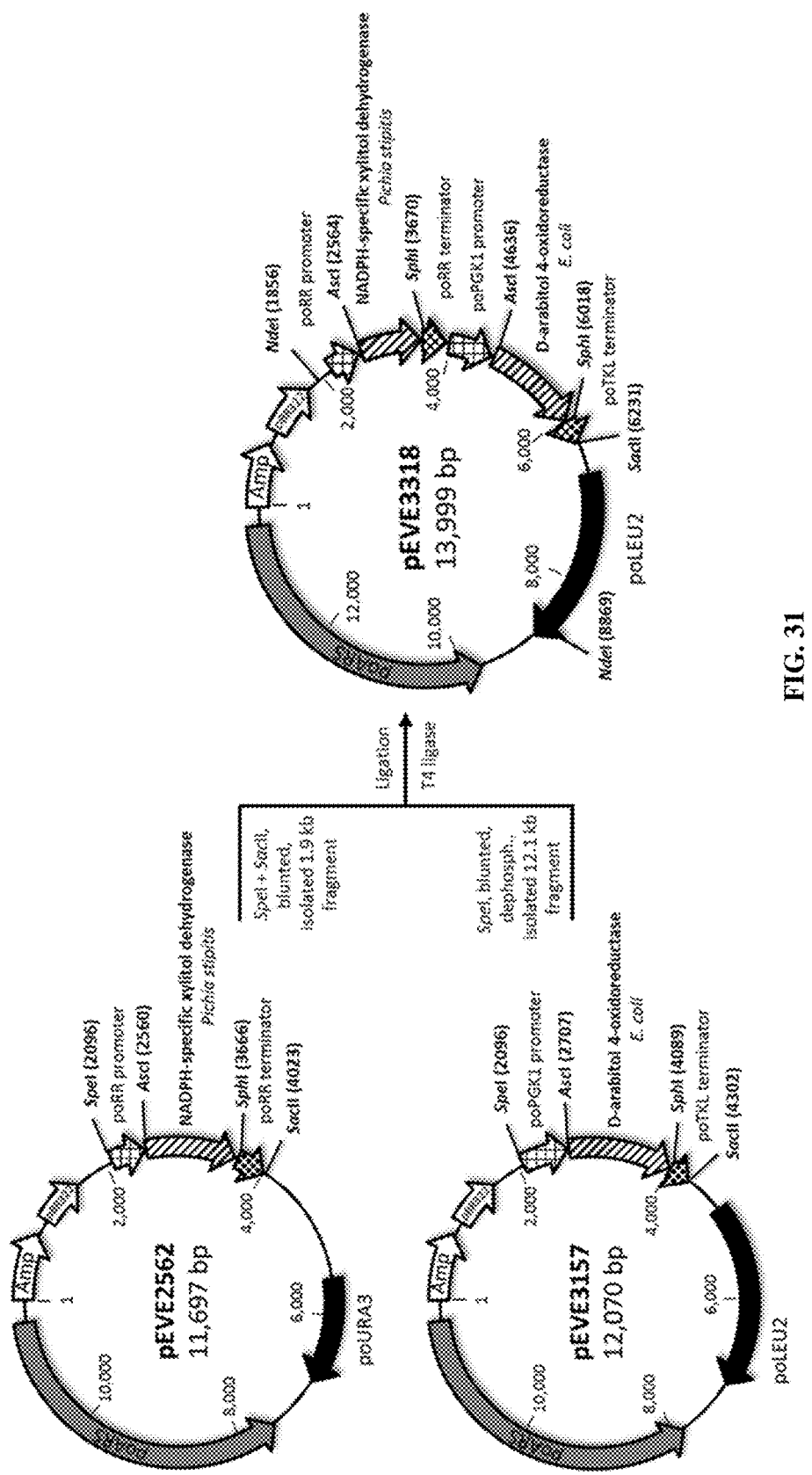

FIG. 31: Construction of a double expression plasmids comprising the NADPH-specific xylitol dehydrogenase of *P. stipitis* and the NAD$^+$-specific D-arabitol 4-oxidoreductase of *E. coli*.

Figure 32:
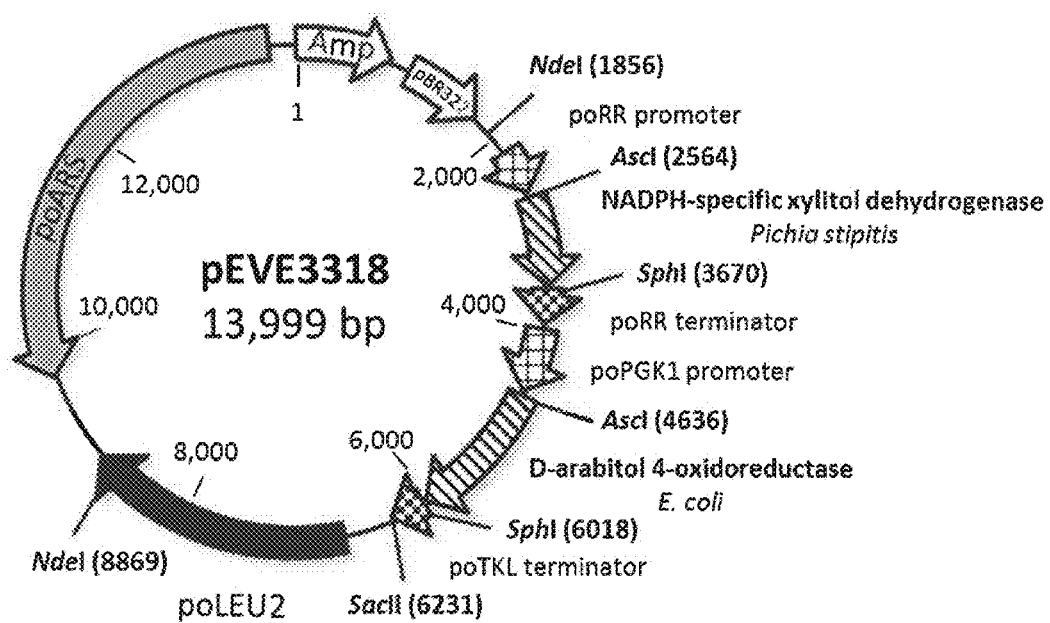

FIG. 32: pEVE3318: Restriction map of the *P. ohmeri* pEVE3318 expression vector, containing the double expression construct of the NADPH-specific xylitol dehydrogenase of *P. stipitis* and the NAD$^+$-specific D-arabitol 4-oxidoreductase of *E. coli*.

Figure 33:
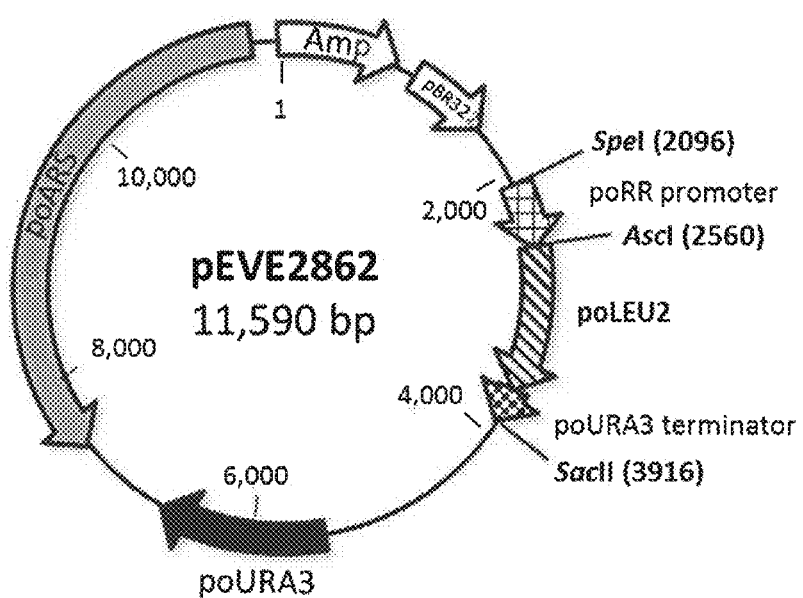

FIG. 33: pEVE2862: Restriction map of the *P. ohmeri* pEVE2862 expression vector, containing the *P. ohmeri* LEU2 marker flanked by a *P. ohmeri* ribulose reductase (poRR) promoter and an orotidine-6-phosphate decarboxylase (poURA3) terminator.

Figure 34:
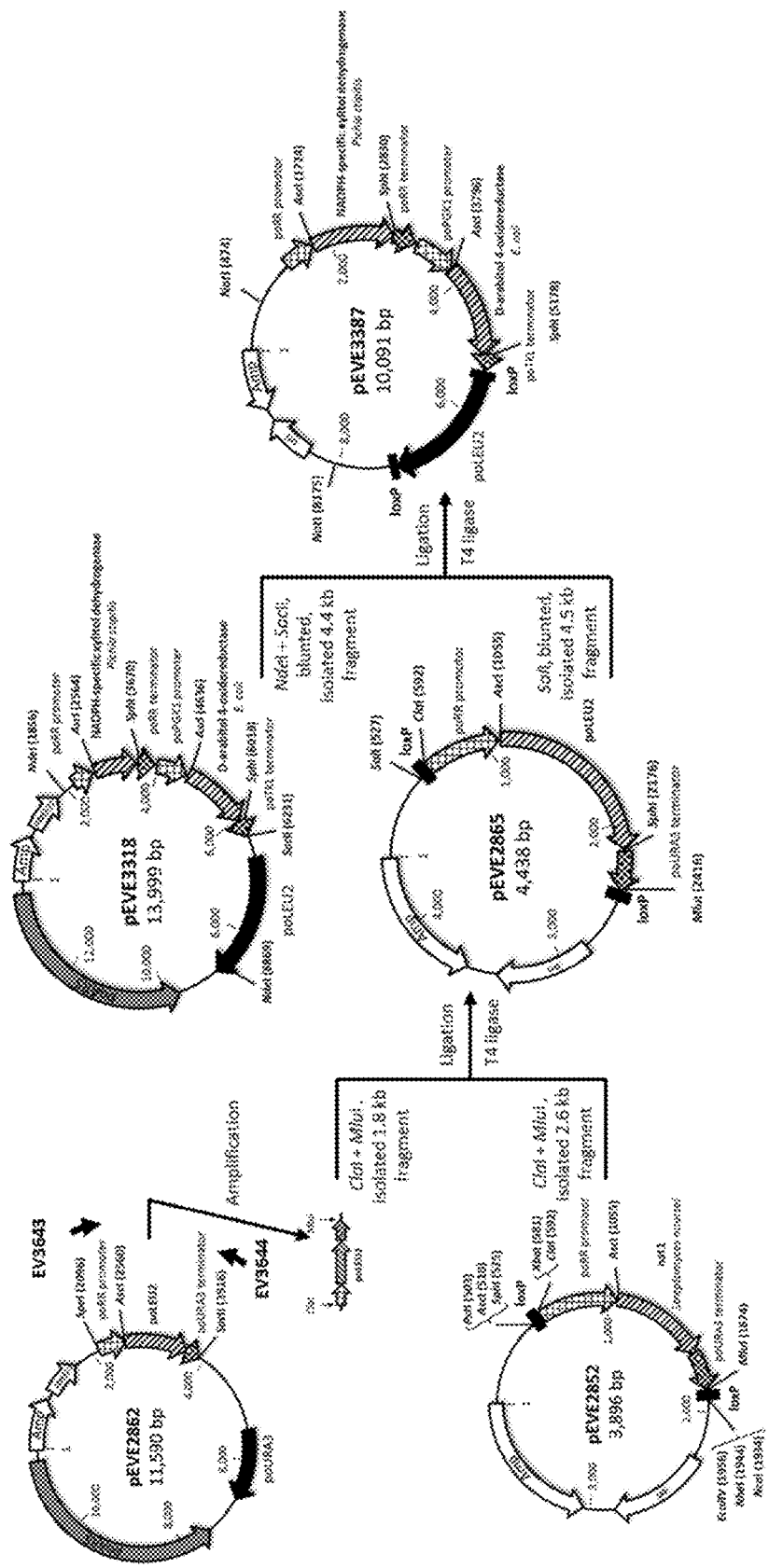

FIG. 34: Construction of an integrative vector for the genomic expression of the *E. coli* NAD+-specific D-arabitol 4-oxidoreductase gene and the *P. stipitis* NADPH-specific xylitol dehydrogenase gene in *P. ohmeri*.

Figure 35:
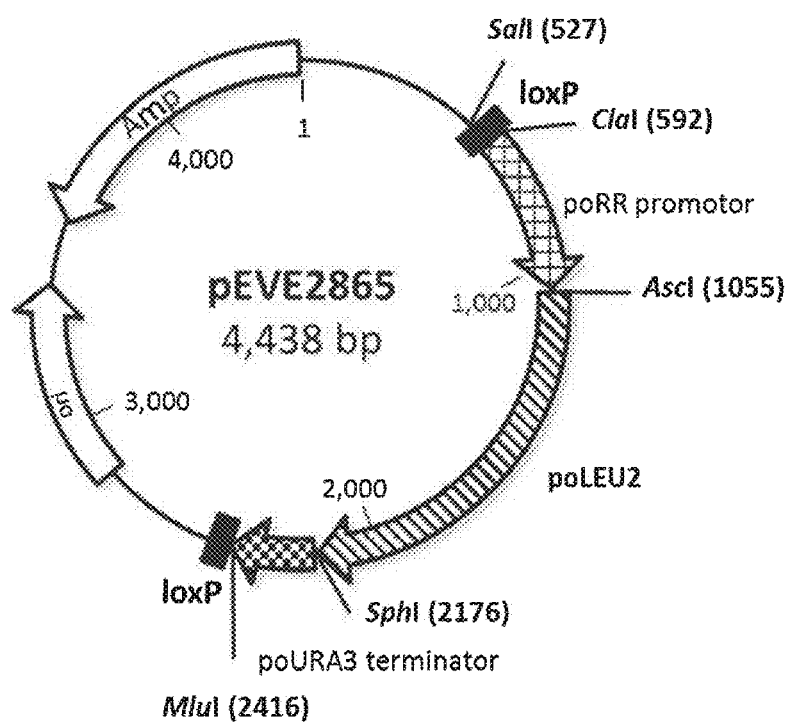

FIG. 35: pEVE2865: Restriction map of the *P. ohmeri* pEVE2865 integration vector, containing the *P. ohmeri* LEU2 marker flanked by two loxP sites.

Figure 36:
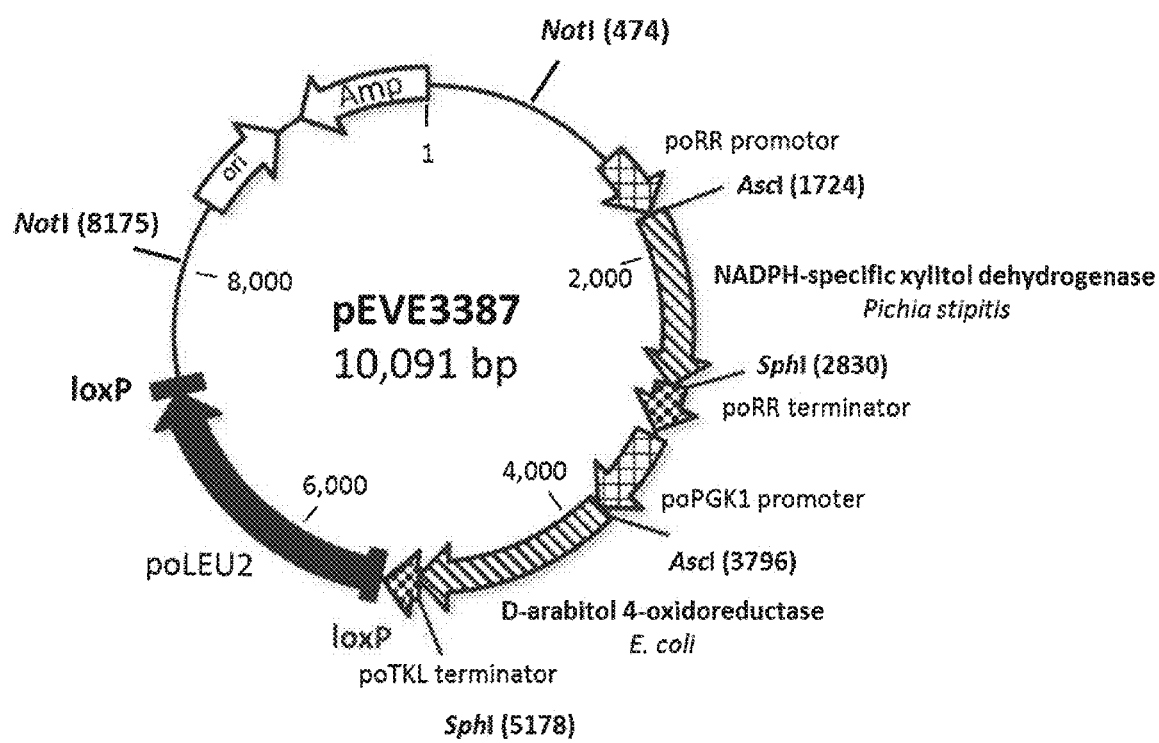

FIG. 36: pEVE3387: Restriction map of the *P. ohmeri* pEVE3387 integration vector, containing the double expression construct of the NADPH-specific xylitol dehydrogenase gene of *P. stipitis* and the NAD$^+$-specific D-arabitol 4-oxidoreductase of *E. coli* with a *P. ohmeri* LEU2 selection marker flanked by two loxP sites.

Figure 37:
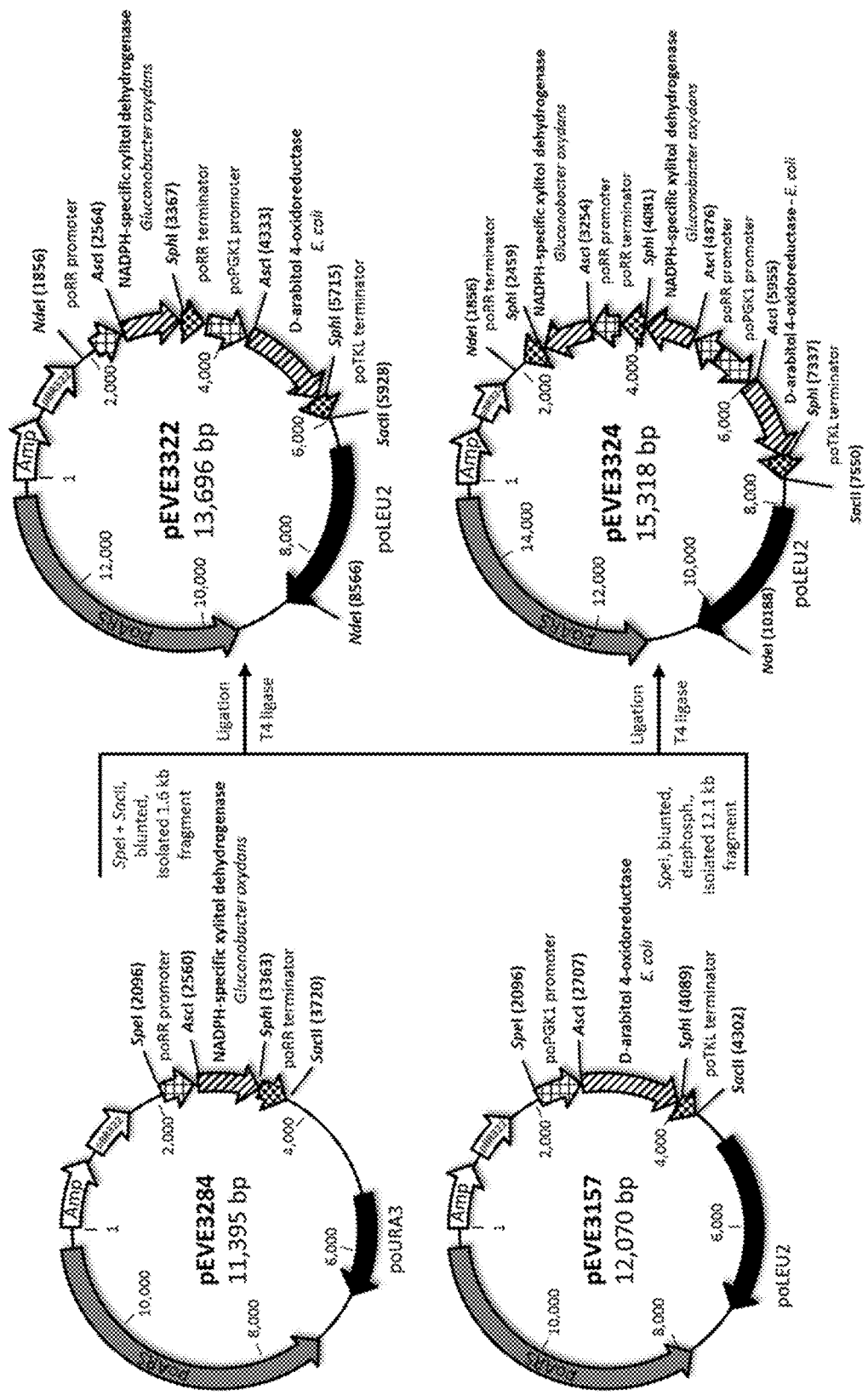

FIG. 37: Construction of double/triple expression plasmids comprising the NADPH-specific xylitol dehydrogenase of *G. oxydans* and the NAD$^+$-specific D-arabitol 4-oxidoreductase of *E. coli*.

Figure 38:
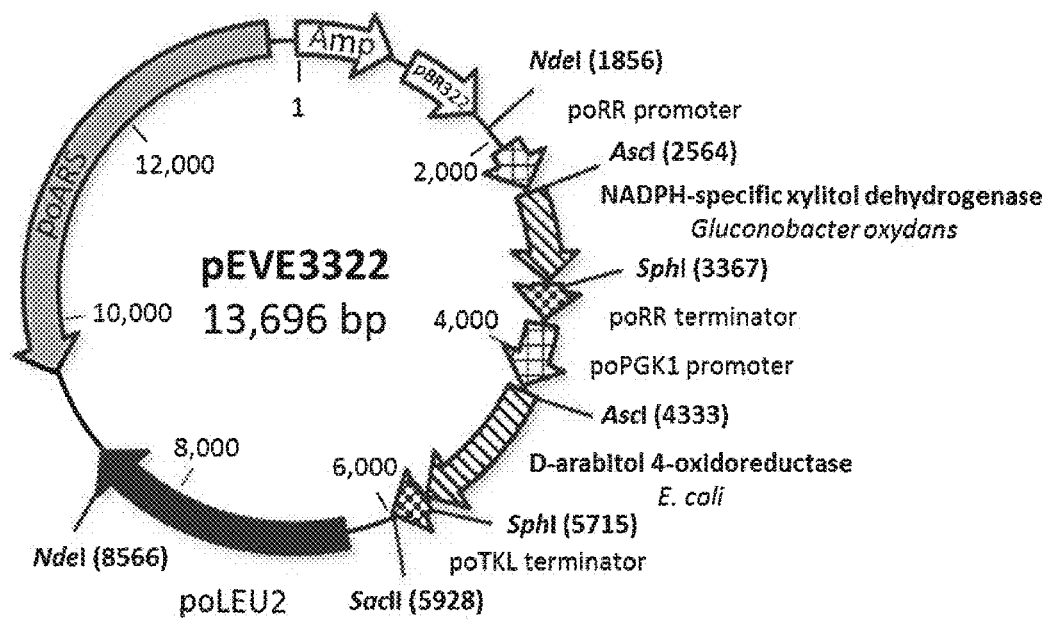
Figure 38:
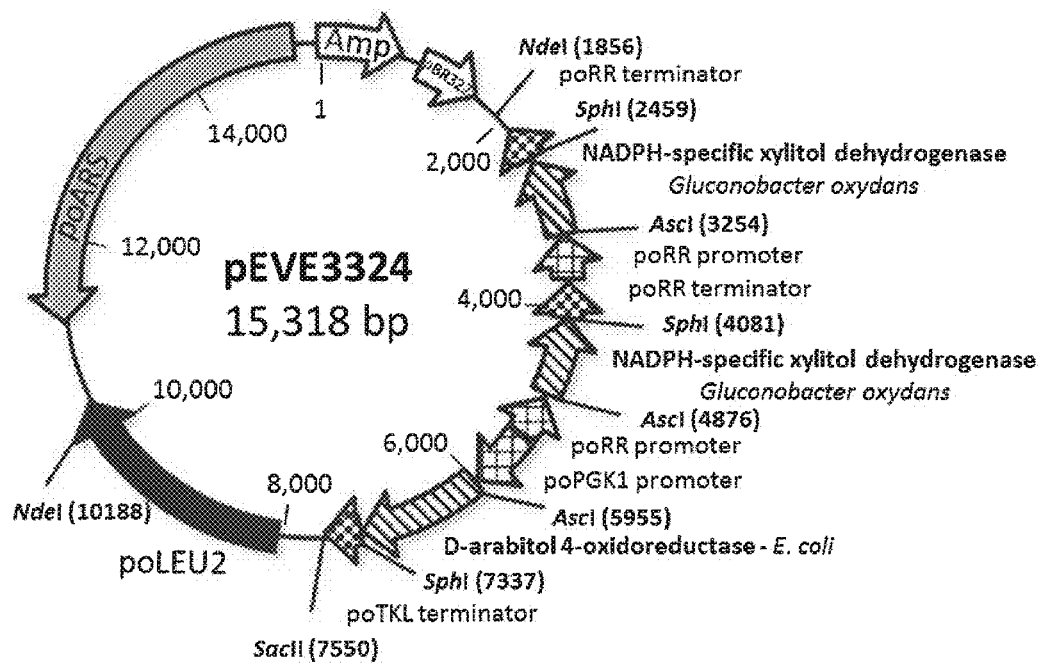

FIG. 38: pEVE3322/pEVE3324: Restriction map of the *P. ohmeri* pEVE3322/pEVE3324 expression vectors, containing either the double expression construct of the NADPH-specific xylitol dehydrogenase of *G. oxydans* and the NAD$^+$-specific D-arabitol 4-oxidoreductase of *E. coli* or the triple expression construct of two NADPH-specific xylitol dehydrogenase genes of *G. oxydans* and one NAD$^+$-specific D-arabitol 4-oxidoreductase of *E. coli*.

Figure 39:
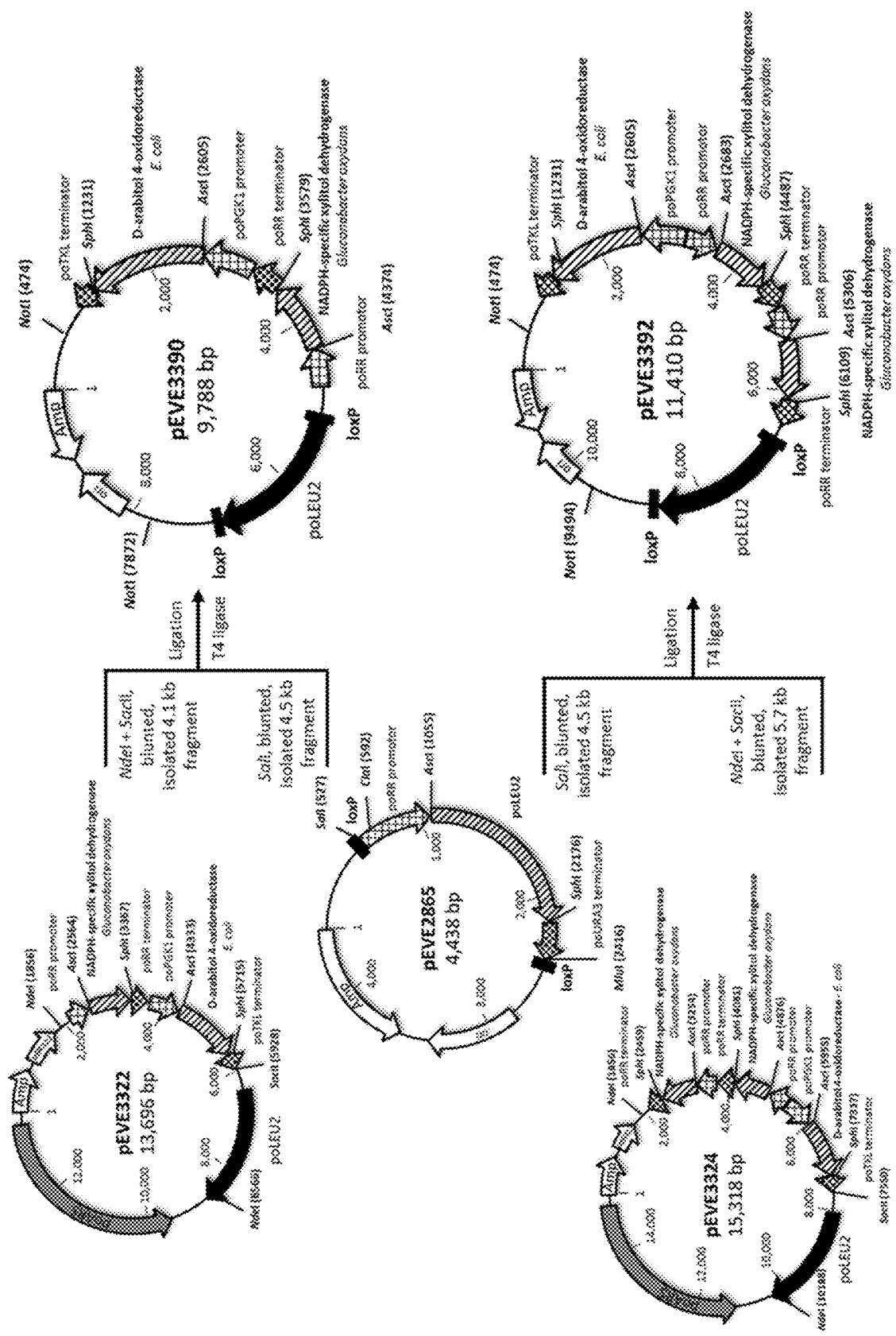

FIG. 39: Construction of an integrative vector for the genomic expression of the *E. coli* NAD+-specific D-arabitol 4-oxidoreductase gene and the *G. oxydans* NADPH-specific xylitol dehydrogenase gene in *P. ohmeri*.

Figure 40:
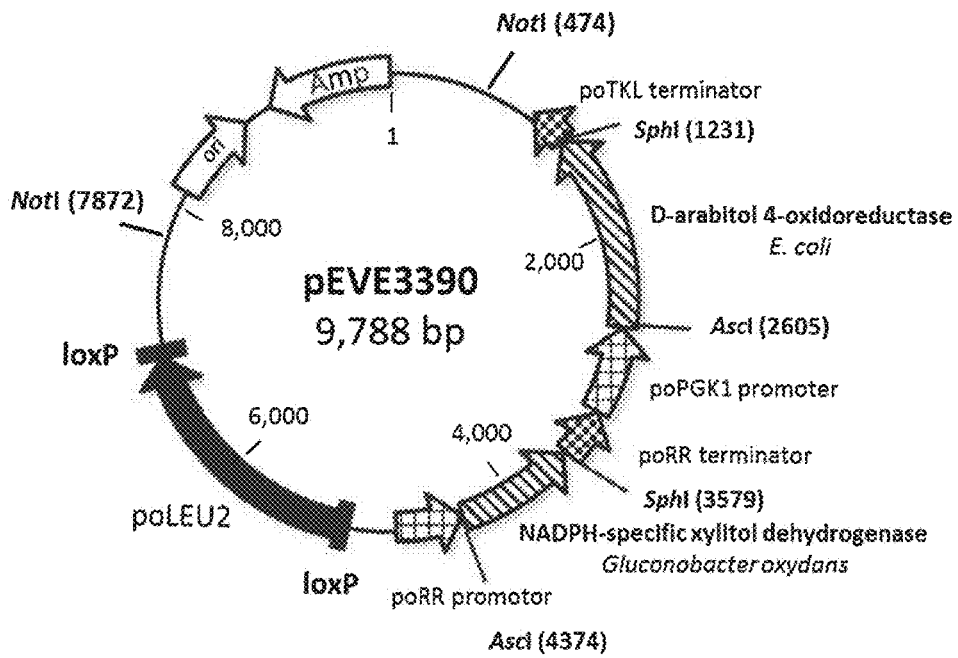
Figure 40:
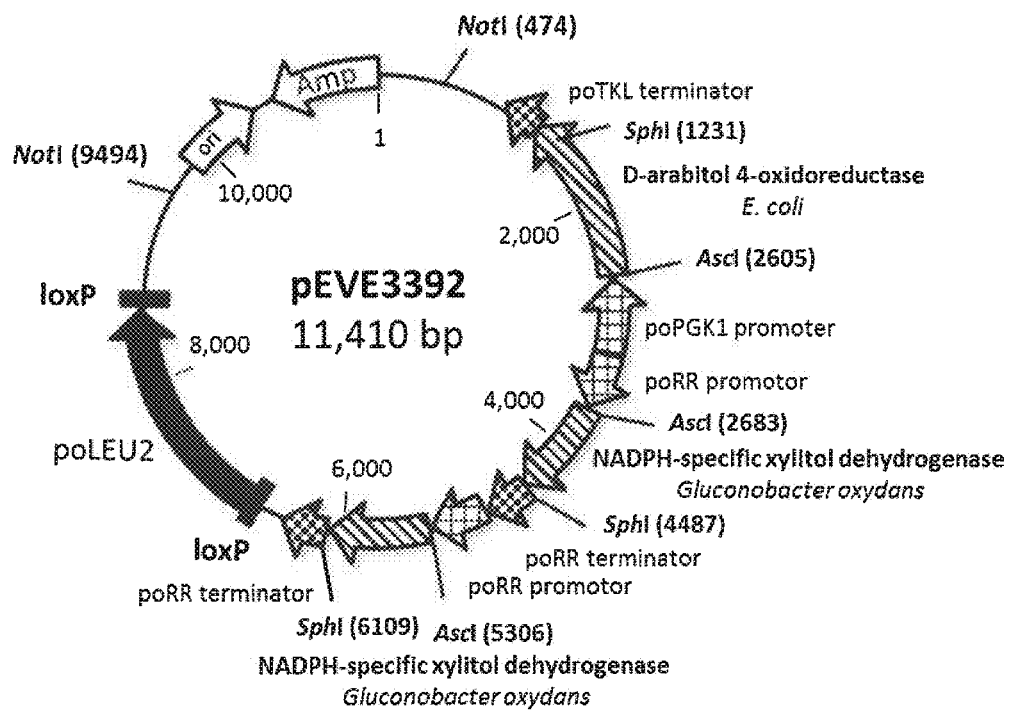

FIG. 40: pEVE3390IpEVE3392: Restriction map of the *P. ohmeri* pEVE3390/pEVE3392 integration vectors, containing either the double expression construct of the NADPH-specific xylitol dehydrogenase of *G. oxydans* and the NAD$^+$-specific D-arabitol 4-oxidoreductase of *E. coli* or the triple expression construct of two NADPH-specific xylitol dehydrogenase genes of *G. oxydans* and one NAD$^+$-specific D-arabitol 4-oxidoreductase of *E. coli* with a *P. ohmeri* LEU2 selection marker flanked by two loxP sites.

Figure 41:
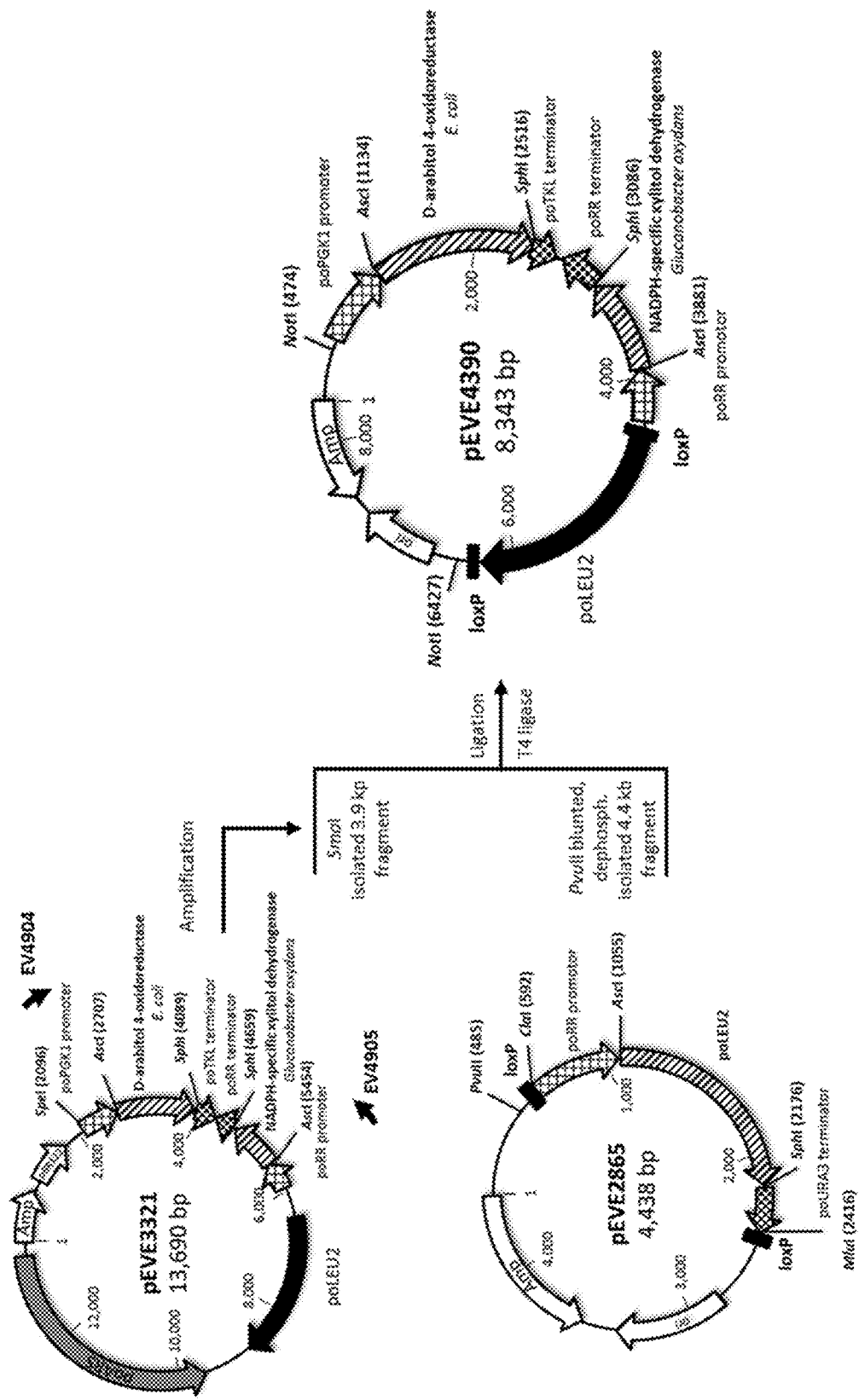

FIG. 41: Construction of an integrative vector for the genomic expression of the *E. coli* NAD+-specific D-arabitol 4-oxidoreductase gene and the *G. oxydans* NADPH-specific xylitol dehydrogenase gene in *P. ohmeri*.

Figure 42:
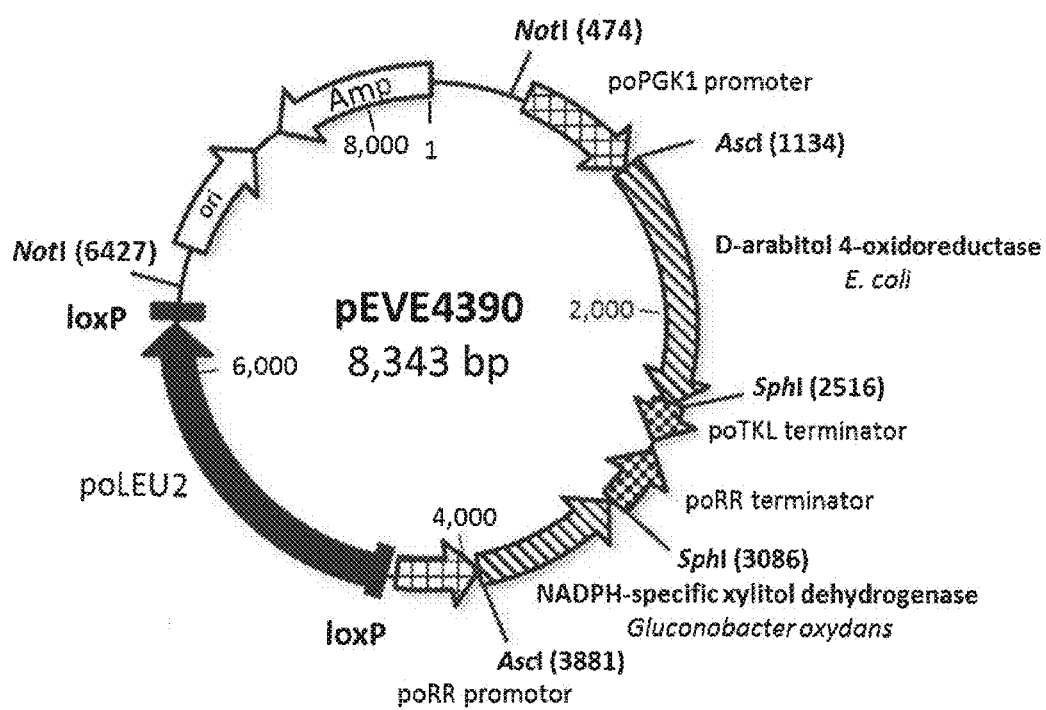

FIG. 42: pEVE4390: Restriction map of the *P. ohmeri* pEVE4390 expression vector, containing the double expression construct of the NAD$^+$-specific D-arabitol 4-oxidoreductase of *E. coli* and the NADPH-specific xylitol dehydrogenase gene of *G. oxydans* with a *P. ohmeri* LEU2 selection marker flanked by two loxP sites.

Figure 43:
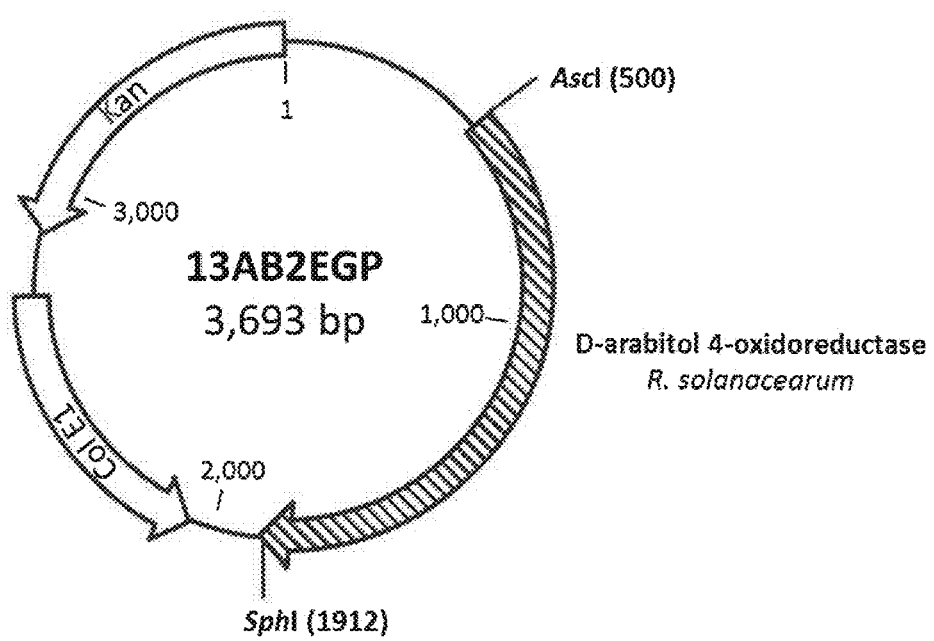

FIG. 43: 13AB2EGF: Restriction map of the synthesized NAD+-specific D-arabitol 4-oxidoreductase from *R. solanacearum* flanked by AscI and SphI restriction sites.

Figure 44:
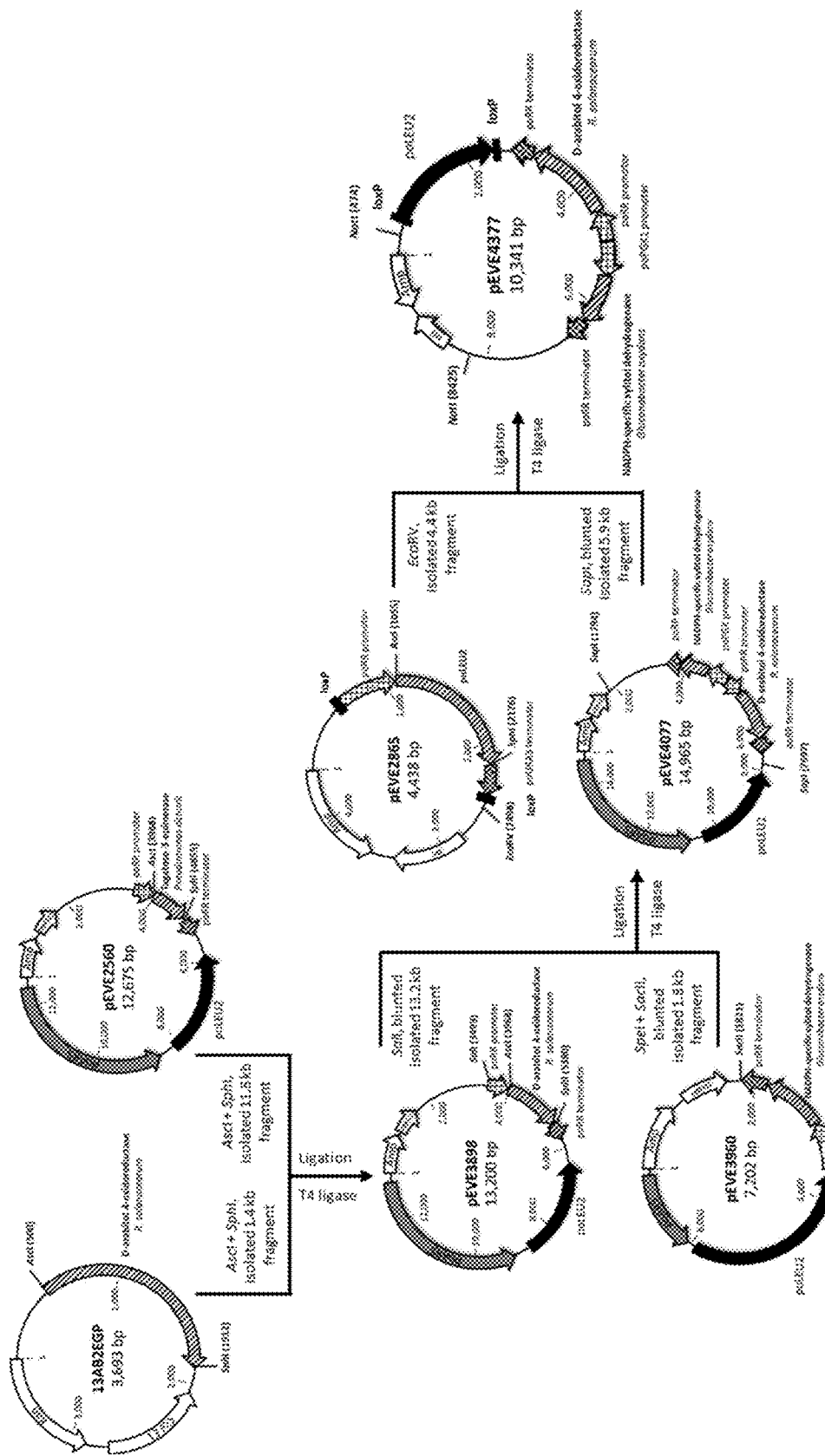

FIG. 44: Construction of an integrative vector for the genomic expression of the *R. solanacearum* NAD+-specific D-arabitol 4-oxidoreductase gene and the *G. oxydans* NADPH-specific xylitol dehydrogenase gene in *P. ohmeri*

Figure 45:
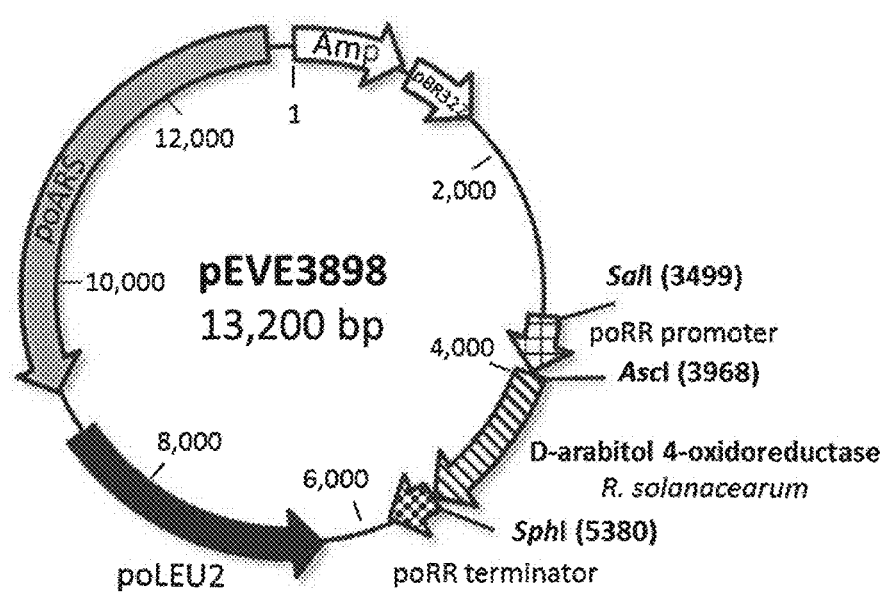

FIG. 45: pEVE3898: Restriction map of the *P. ohmeri* pEVE3898 expression vector, with a cloned expression cassette containing the NAD+-specific D-arabitol 4-oxidoreductase of *Ralstonia solanacearum* flanked by a *P. ohmeri* ribulose reductase (poRR) promoter and terminator.

Figure 46:
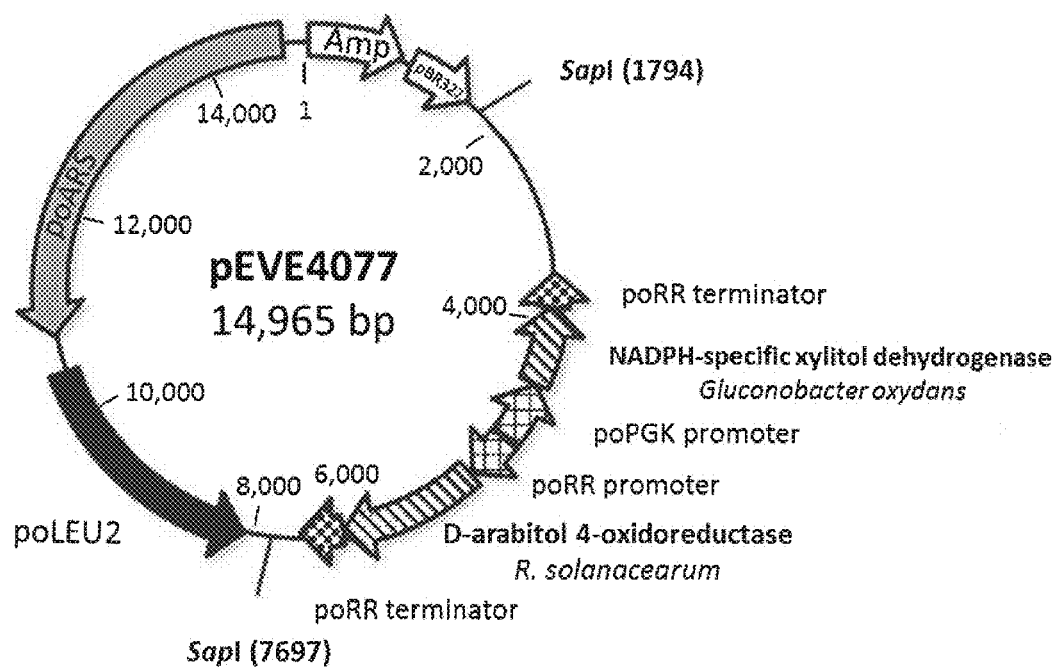

FIG. 46: pEVE4077: Restriction map of the *P. ohmeri* pEVE4077 expression vector, with a double expression construct of the NADPH-specific xylitol dehydrogenase of *G. oxydans* and the NAD$^+$-specific D-arabitol 4-oxidoreductase of *R. solanacearum*.

Figure 47:
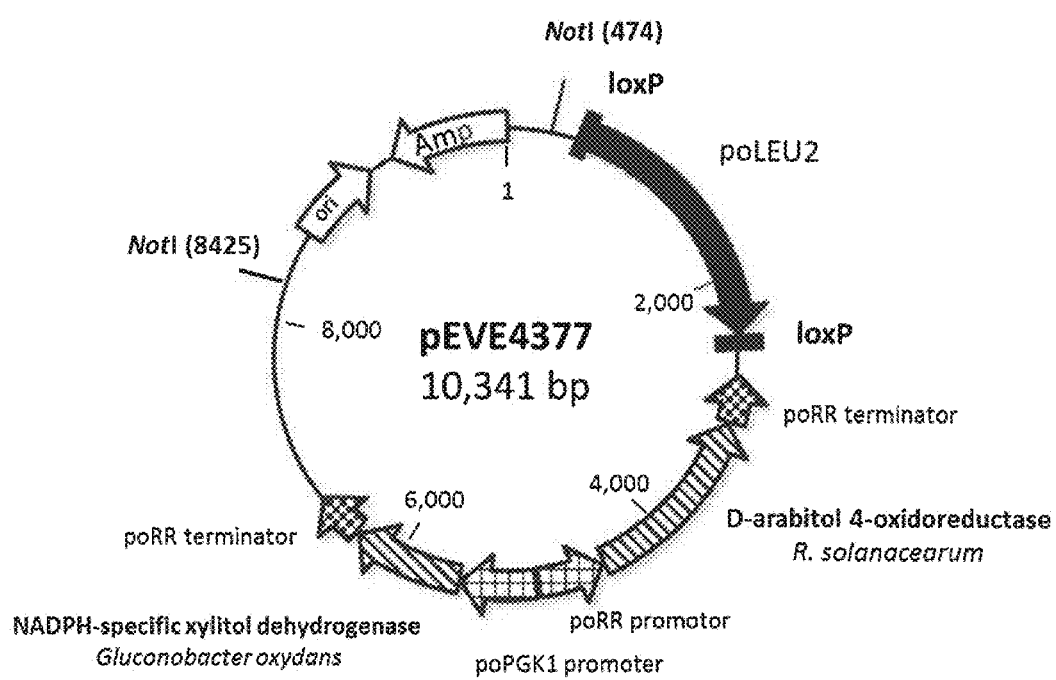

FIG. 47: pEVE4377: Restriction map of the *P. ohmeri* pEVE4377 integration vector, with a double expression construct of the NADPH-specific xylitol dehydrogenase of *G. oxydans* and the NAD$^+$-specific D-arabitol 4-oxidoreductase of *R. solanacearum* and the poLEU2 selection marker flanked by two loxP sites.

SEQUENCE LISTING

| SEQ ID No | Description |
|---|---|
| 1 | Sequence encoding NAD$^+$-specific D-arabitol 4-oxidoreductase from *E. coli* flanked by AscI and SphI restriction sites |
| 2 | Amino acid sequence of NAD$^+$-specific D-arabitol 4-oxidoreductase from *E. coli* |
| 3 | Sequence encoding NAD$^+$-specific D-arabitol 4-oxidoreductase from *E. coli* |

| SEQ ID No | Description |
|---|---|
| 4 | Sequence encoding NADPH-specific xylitol dehydrogenase from *Pichia stipitis* flanked by HindIII and SacII restriction sites |
| 5 | Amino acid sequence of NADPH-specific xylitol dehydrogenase from *P. stipitis* |
| 6 | Sequence encoding NADPH-specific xylitol dehydrogenase from *Pichia stipitis* |
| 7 | Sequence encoding NADPH-specific xylitol dehydrogenase from *Gluconobacter oxydans* flanked by AscI and SphI restriction sites |
| 8 | Amino acid sequence of NADPH-specific xylitol dehydrogenase from *Gluconobacter oxydans* |
| 9 | Sequence encoding NADPH-specific xylitol dehydrogenase from *Gluconobacter oxydans* |
| 10 | Sequence encoding tagatose-3-epimerase of *Pseudomonas cichorii* ST24 |
| 11 | Amino acid sequence of tagatose-3-epimerase of *Pseudomonas cichorii* ST24 |
| 28 | Sequence encoding the nat1 gene of *Streptomyces noursei* flanked by AscI and SphI restriction sites |
| 42 | Sequence encoding the NAD+-specific D-arabitol 4-oxidoreductase from *R. solanacearum* flanked by AscI and SphI restriction sites |
| 43 | Amino acid sequence of NAD+-specific D-arabitol 4-oxidoreductase from *R. solanacearum* |

EXAMPLES

Example 1. Choice of a *Pichia ohmeri* Strain as Preferred Host for Genetic Engineering As host strain of choice, *Pichia ohmeri*:

is a producer of significant amounts of arabitol from glucose, under high osmotic pressure medium, for example medium containing 10-60% D-glucose, and preferably 25% D-glucose ("Normal" medium usually contains only 2-3% glucose.)

has a redox balance that permits the generation of the cofactors needed.

As an illustration of its performances, the following tables indicate the enzyme activities involved in the arabitol metabolic pathway of *Pichia ohmeri* (Sophie HUCHETTE Thesis, 1992)

The Hexose Monophosphate Pathway: from Glucose-6-P to D-Ribulose-5-P and D-Xylulose-5-P The oxidative part of the PPP, also named the Hexose Monophosphate Pathway (HMP), is a NADPH-producing pathway. The two NADP+-dependent enzymes which are Glucose-6-P dehydrogenase (E.C.1.1.1.49) and 6-P-Gluconate dehydrogenase (E.C.1.1.1.44) participate to the oxidation of 1 mole of glucose-6-P in 1 mole of D-ribulose-5-P and generate 2 moles of NADPH.

TABLE 1

Hexose Monophosphate Pathway in *P. ohmeri* ATCC 20209

| Enzymes | Specific activity U/mg |
|---|---|
| NADP+ G6P dehydrogenase | 1.5 |
| NADP+ 6PG dehydrogenase | 0.55 |

One unit of enzyme activity was defined as the consumption of 1 μmole of NAD(P)H or NAD(P)+ per minute per mL of crude extract. One unit of specific activity was defined as one unit of enzyme activity per mg of proteins in crude extract.

The kinetic parameters of the following enzymes were determined: D-ribulose-5-P 3-epimerase (E.C 5.1.3.1), D-ribose-5-P keto-isomerase (E.C.5.3.1.6), transketolase (E.C.2.2.1.1) and acidic phosphatases (E.C. 3.1.3.2).

TABLE 2

Kinetic parameters of enzymes using D-Ribulose-5-P as substrate in *P. ohmeri* ATCC 20209

| Enzymes | $K_M$ mM | $V_M$ U/mg |
|---|---|---|
| D-Ribulose-5-P 3-epimerase | 6.3 | 3 |
| D-Ribose-5-P keto-isomerase | 0.35 | 1.8 |
| Acid phosphatase | 4.3 | 0.65 |

One unit of enzyme activity was defined as the consumption of 1 μmole of NAD(P)H or NAD(P)+ per minute per mL of crude extract. One unit of specific activity was defined as one unit of enzyme activity per mg of proteins in crude extract.

TABLE 3

Kinetic parameters of enzymes using D-Xylulose-5-P as substrate in *P. ohmeri* ATCC 20209

| Enzymes | $K_M$ mM | $V_M$ U/mg |
|---|---|---|
| D-Ribulose-5-P 3-epimerase | 6.6 | 0.7 |
| Transketolase (D-ribose-5-P) | 0.2 | 0.9 |
| Transketolase (Erythrose-4-P) | 0.6 | 1.45 |
| Acid phosphatase | 16 | 0.11 |

One unit of enzyme activity was defined as the consumption of 1 μmole of NAD(P)H or NAD(P)+ per minute per mL of crude extract. One unit of specific activity was defined as one unit of enzyme activity per mg of proteins in crude extract.

In vivo, D-xylulose-5-P, synthetized from the epimerization of D-ribulose-5-P, enters efficiently into the non-oxidative part of the PPP via the transketolization. Consequently, D-xylulose-5-P is not available for its dephosphorylation into D-xylulose.

NADH and NADPH Specific D-Ketopentose-oxidoreductases

D-Ribulose and D-Xylulose are produced by dephosphorylization of D-Ribulose-5-P and D-Xylulose-5-P.

The Michaelis-Menten constants highlight the affinities of the NADH and NADPH-D-ketopentose-oxidoreductases for each substrate and the corresponding maximum velocities.

TABLE 4

NADH-specific D-ketopentose-oxidoreductase kinetic parameters of *P. ohmeri* ATCC 20209

| Substrate | $K_M$ mM | $V_M$ U/mg |
|---|---|---|
| D-Ribulose | 90 | 1 |
| Ribitol | 16 | 0.16 |

TABLE 4-continued

NADH-specific D-ketopentose-oxidoreductase kinetic parameters of
P. ohmeri ATCC 20209

| Substrate | $K_M$ mM | $V_M$ U/mg |
|---|---|---|
| D-Xylulose | 5 | 0.6 |
| Xylitol | 7 | 0.2 |

One unit of enzyme activity was defined as the consumption of 1 μmole of NAD(P)H or NAD(P)+ per minute per mL of crude extract. One unit of specific activity was defined as one unit of enzyme activity per mg of proteins in crude extract.

NADH-specific D-ketopentose-oxidoreductase, forming ribitol and xylitol respectively from D-ribulose and D-xylulose shows a higher affinity for D-xylulose than D-ribulose. The reverse reaction shows a good affinity for xylitol and ribitol explaining the good growth of the host strain on these two polyols.

TABLE 5

NADPH-specific D-ketopentose-oxidoreductase kinetic parameters of
P. ohmeri ATCC 20209

| Substrate | $K_M$ mM | $V_M$ U/mg |
|---|---|---|
| D-Ribulose | 72 | 3.4 |
| D-Arabitol | 1300 | 0.8 |
| D-Xylulose | 262 | 1.5 |
| Xylitol | 200 | 0.15 |

One unit of enzyme activity was defined as the consumption of 1 μmole of NAD(P)H or NAD(P)+ per minute per mL of crude extract. One unit of specific activity was defined as one unit of enzyme activity per mg of proteins in crude extract.

NADPH-specific D-ketopentose-oxidoreductase, forming D-arabitol from D-ribulose and forming xylitol from D-xylulose shows a higher affinity for D-ribulose than D-xylulose. The reverse reaction shows a very low affinity for D-arabitol explaining the non-growth of the host strain on this polyol.

The two ketopentose-oxidoreductases from the host strain were characterized as different from the previous enzymes described in *Saccharomyces rouxii* by Ingram and Wood, 1965 (Journal of Bacteriology, vol. 89, n°5, 1186-1194). Indeed, in *Saccharomyces rouxii*, no forward reaction was detected on D-ribulose and NADH and a backward reaction was detected on D-arabitol with NADPH.

The Haldane relationship predicts in vivo enzyme kinetic behaviors.

TABLE 6

| Substrat/Product | $K_{eq}$ mM$^{-1}$ |
|---|---|
| Haldane constants determination: NADH-specificD-Ketopentose-oxidoreductase | |
| D-Ribulose/Ribitol | 78 |
| D-Xylulose/Xylitol | 104 |
| Haldane constants determination: NADPH-specificD-Ketopentose-oxidoreductase | |
| D-Ribulose/D-Arabitol | 104 |
| D-Xylulose/Xylitol | 24 |

The two enzymes favor the forward reaction (D-ketopentose oxidation) over the backward reaction (pentitol reduction).

The PPP in the host strain is extremely efficient and 2 moles of NADPH are generated from 1 mole of glucose consumed. Consequently, NADPH would be available in excess for both anabolic reactions and maintenance reactions. The host strain must produce D-arabitol from D-ribulose or xylitol from D-xylulose to balance the NADPH/NADP$^+$ redox couple.

The inhibitory effect of NADP$^+$ on NADPH-specific D-ketopentose-oxidoreductase has been determined in vitro. The activity is 80% less when NADP$^+$ is added in excess. Even if this concentration is not compatible with the intracellular NADP$^+$ concentration, this result gives some overview of the role of the NADPH-specific D-ketopentose oxidoreductase into the balance of the NADPH/NADP$^+$ redox couple.

The host strain produces only D-arabitol from D-ribulose as D-xylulose is not available because of the entrance of D-xylulose-5-P into the non-oxidative part of the PPP. The link between the production of D-arabitol and the NADPH/NADP$^+$ redox balance has been demonstrated in the host strain by evaluating the impact of the overexpression of Glucose-6-P dehydrogenase onto the D-arabitol production. So, the obtained strain harbors a G6PDH activity 1.5 times higher and produces 10% more of D-arabitol compared to the host strain (FR2772788).

Example 2. *Pichia ohmeri* Codon Usage

The codon usage of *P. ohmeri* was determined from the available DNA and corresponding amino acid sequence of five *P. ohmeri* genes: transketolase, glucose-6-phosphate dehydrogenase (FR 2772788), ribulose reductase, beta-isopropylmalate dehydrogenase—LEU2 (Piredda and Gaillardin, Yeast, vol. 10:1601-1612 (1994) and orotidine-5'-phosphate decarboxylase—URA3 (Piredda and Gaillardin, 1994, supra).

Every individual gene was divided in nucleotide triplets encoding for a single amino acid. The five genes consisted of a total of 2091 codons.

For each amino acid, the number of every codon present in the five genes was counted, divided by 2091 and multiplied by 1000. This way, the frequency of a specific codon in 1000 codons was estimated.

The preliminary codon usage of *P. ohmeri* is depicted in Table 7.

All heterologous genes expressed in *P. ohmeri*, except the xylitol dehydrogenase from *P. stipitis*, were codon optimized using this table and the Optimizer program (*Nucleic Acids Research*, 2007, 35, W126-W131).

The obtained sequence was sent for gene synthesis after manual addition of recognition sites for restriction enzymes at the respective 5' and 3' ends of the sequence encoding the enzyme.

TABLE 7

Codon usage table of *P. ohmeri* derived from
5 coding sequences (CDS)
*Pichia ohmeri* [gbpln]: 5 CDS's (2091 codons)
fields: [triplet] [frequency: per thousand] ([number])

| | | | |
|---|---|---|---|
| TTT | 10.5( 22) | TCT | 30.6( 64) |
| TTC | 30.1( 63) | TCC | 23.4( 49) |
| TTA | 5.3( 11) | TCA | 4.8( 10) |
| TTG | 64.1( 134) | TCG | 9.6( 20) |
| CTT | 10.5( 22) | CCT | 12.0( 25) |
| CTC | 12.0( 25) | CCC | 0.0( 0) |
| CTA | 0.0( 0) | CCA | 34.0( 71) |
| CTG | 2.9( 6) | CCG | 0.5( 1) |
| ATT | 27.7( 58) | ACT | 22.0( 46) |
| ATC | 30.6( 64) | ACC | 24.4( 51) |
| ATA | 2.4( 5) | ACA | 3.3( 7) |
| ATG | 14.3( 30) | ACG | 1.4( 3) |

TABLE 7-continued

Codon usage table of *P. ohmeri* derived from
5 coding sequences (CDS)
Pichia ohmeri [gbpln]: 5 CDS's (2091 codons)
fields: [triplet] [frequency: per thousand] ([number])

| | | | |
|---|---|---|---|
| GTT | 27.3( 57) | GCT | 46.9( 98) |
| GTC | 19.1( 40) | GCC | 27.7( 58) |
| GTA | 1.9( 4) | GCA | 11.0( 23) |
| GTG | 21.5( 45) | GCG | 3.3( 7) |
| TAT | 7.7( 16) | TGT | 5.7( 12) |
| TAC | 27.3( 57) | TGC | 1.4( 3) |
| TAA | 1.4( 3) | TGA | 0.0( 0) |
| TAG | 1.0( 2) | TGG | 12.9( 27) |
| CAT | 3.3( 7) | CGT | 5.7( 12) |
| CAC | 15.8( 33) | CGC | 1.0( 2) |
| CAA | 12.4( 26) | CGA | 0.0( 0) |
| CAG | 17.7( 37) | CGG | 0.5( 1) |
| AAT | 7.7( 16) | AGT | 1.9( 4) |
| AAC | 29.2( 61) | AGC | 2.4( 5) |
| AAA | 11.0( 23) | AGA | 26.3( 55) |
| AAG | 64.1( 134) | AGG | 0.0( 0) |
| GAT | 23.0( 48) | GGT | 60.7( 127) |
| GAC | 35.9( 75) | GGC | 10.5( 22) |
| GAA | 18.7( 39) | GGA | 12.0( 25) |
| GAG | 46.9( 98) | GGG | 1.0( 2) |

Example 3. Cloning of the *E. coli* Bacterial NAD$^+$-Specific D-Arabitol 4-Oxidoreductase (D-Xylulose-Forming) Gene A DNA fragment encoding the NAD$^+$-specific D-arabitol 4-oxidoreductase altD from *E. coli* was chemically synthesized (GeneArt® Gene Synthesis, Life Technologies, Regensburg, Germany), according to the submitted sequence of SEQ ID NO: 1.

Nucleotides 1441 to 2808 of sequence AF378082A (obtained from the NCBI GenBank database) coding for the altD gene were used as template and subjected to codon optimization for use in *P. ohmeri* ATCC 20209 according to Table 7 of example 2, using the Optimizer program.

At the 5' and 3' ends of the resulting sequence, nucleotides encoding for the recognition sites of the restriction enzymes AscI (GGCGCGCC) and SphI (GCATGC) respectively, were added in order to facilitate further cloning.

Additionally, an adenosine triplet was included in front of the start ATG to account for an adenosine at the −3 position in the Kozak-like sequence of yeasts.

The final sequence (SEQ ID NO: 1) was then submitted for synthesis (GeneArt, Regensburg, Germany).

The synthesized DNA fragment encoding the NAD$^+$-specific D-arabitol 4-oxidoreductase from *E. coli* was delivered as 5 μg lyophilized plasmid DNA in a pMK-RQ derived vector (12ABYWMP, FIG. 1).

For further sub-cloning the gene was released by restriction cutting with AscI and SphI enzymes (New England Biolabs, Ipswich, Mass.).

Example 4. Mutagenesis and Cloning of the *Pichia stipitis* NADH and NADPH-Specific Xylitol Dehydrogenase Cloning of the *Pichia stipitis* NADH-Specific Xylitol Dehydrogenase Gene The known nucleotide sequence of the yeast (*Pichia stipitis*) gene XYL2, encoding xylitol dehydrogenase (Kotter et al., Curr. Genet. 18:493-500 (1990)) was cloned in the plasmidic vector lig 7.78 following the teaching of FR 2 765 589 (see example 4 and FIG. 7 of this patent). The restriction map of the vector is presented in FIG. 2A.

Mutagenesis and Cloning of the *Pichia stipitis* NADPH-Specific Xylitol Dehydrogenase Gene A DNA fragment encoding the NADPH-specific xylitol dehydrogenase XYL2 from *Pichia stipitis* was chemically synthesized (GeneArt® Gene Synthesis, Life Technologies, Regensburg, Germany) according to the sequence of SEQ ID NO: 4.

Nucleotides 319 to 1410 of sequence X55392.1 (obtained from the NCBI GenBank database) coding for the XYL2 gene were used as template.

According to the paper from Watanabe et al. (*J. Biol. Chem.*, 2005, 280, 10340-10345), the cofactor preference of the xylitol dehydrogenase could be changed from NADH to NADPH by introducing four published amino acid mutations: D207A/I208R/F209S/N211R (numbering based on P22144 protein sequence obtained from the UniProt database).

Accordingly, the codons encoding for D207, I208, F209 and N211 were manually replaced by GCT, AGA, TCA and AGA in the corresponding sequence, respectively.

Additionally, nucleotides coding for the recognition sites of the restriction enzymes HindIII (AAGCTT) and SacII (CCGCGG) were manually included at the respective 5' and 3' ends, in order to facilitate further cloning.

Furthermore, an adenosine triplet was included in front of the start ATG to account for an adenosine at the —3 position in the Kozak-like sequence of yeasts. The final sequence (SEQ ID NO: 4) was submitted for synthesis (GeneArt, Regensburg, Germany).

The synthesized DNA fragment encoding the NADPH-specific xylitol dehydrogenase from *P. stipitis* was delivered as 5 μg lyophilized plasmid DNA in a pMA-T derived vector (12AALQTP, FIG. 2B).

Example 5. Mutagensis and Cloning, of the *Gluconobacter oxydans* NADPH-Specific Xylitol Dehydrogenase Gene A DNA fragment encoding the NADPH-specific xylitol dehydrogenase Xdh from *Gluconobacter oxydans* was chemically synthesized (GeneArt® Gene Synthesis, Life Technologies, Regensburg, Germany), according to the submitted sequence of SEQ ID NO: 7.

Nucleotides 1063 to 1851 of sequence AB091690.1 (obtained from the NCBI GenBank database) coding for the Xdh gene were used as template and subjected to codon optimization for use in *P. ohmeri* ATCC 20209 according to Table 7 (Example 2) using the Optimizer program.

Based on the publication by Ehrensberger et al. (*Structure*, 2006, 14, 567-575), the cofactor specificity of the enzyme could be changed from NADH to NADPH by introducing two published amino acid mutations: D38S/M39R (numbering based on Q8GR61 protein sequence obtained from the UniProt database).

Thus, the codons encoding for D38 and M39 were manually replaced by TCT and AGA in the corresponding sequence, respectively. Additionally, nucleotides encoding for the recognition sites of the restriction enzymes AscI (GGCGCGCC) and SphI (GCATGC) were manually included at the respective 5' and 3' ends, in order to enable further cloning.

Furthermore, an adenosine triplet was included in front of the start ATG to account for an adenosine at the −3 position in the Kozak-like sequence of yeasts. The final sequence (SEQ ID NO: 7), was submitted for synthesis (GeneArt, Regensburg, Germany).

The synthesized DNA fragment encoding the NADPH-specific xylitol dehydrogenase from *Gluconobacter oxydans* was delivered as 5 μg lyophilized plasmid DNA in a pMA-T derived vector (13AAYSYP, FIG. 3). For further subcloning, the gene was released by restriction cutting with AscI and SphI enzymes (New England Biolabs, Ipswich, Mass.).

Example 6. Construction of a *P. ohmeri* Vector for Heterologous Gene Expression Using the poURA3 Selection Marker The Cloning of a Vector with Replaceable:
promoter,
open reading frame, and
terminator elements
was performed by two successive overlap PCRs of three individual fragments (FIG. 4).

The vector was originally planned as an expression model, to test the cloning and the overexpression of the tagatose 3-epimerase gene in the recombinant *Pichia ohmeri* strain.

As it will be described below, the tagatose 3-epimerase gene has been cloned into specific AscI-SphI restriction sites cassette, allowing the cloning of any gene of interest by using these same sites of insertion.

The cloning was conceived by the following way.

In a first PCR (PCR1), a 490 bp long ribulose reductase promoter fragment of *P. ohmeri* flanked by SpeI and AscI sites (underlined in primer sequence) was amplified using:

```
primer EV2960:
                                      (SEQ ID No 12)
GAACTAGTGGATCCGTAGAAATCTTG
and primer EV2961:
                                      (SEQ ID No 13)
CTTTGTTCATTTTGGCGCGCCTTTTAGTTTAATAAGGGTCCGTG
```

Additionally, at the 5' end of the reverse primer EV2961, a 13 nucleotide long fragment representing the 5' end of the tagatose-3-epimerase gene was added. This fragment together with the 8 nucleotides of the AscI site and the 10 following nucleotides of 3' end of the ribulose reductase promoter were needed as overlap for fusing the fragment of PCR1 with the fragment of PCR2 described below. Genomic DNA of *P. ohmeri* ATCC 20209 was used as template.

For this purpose, a freshly streaked out *P. ohmeri* colony was resuspended in 30 μl of 0.2% SDS and heated for 4 min at 95° C. After full speed centrifugation, 0.5 μl of the supernatant was used for PCR.

The template was amplified in a reaction mix consisting of 200 μM of each dNTP and 0.5 μM of each primer with 0.02 U/μl of iProof™ polymerase (BIO-RAD, Hercules, Calif.) in the appropriate 1× buffer.

The PCR was performed with an initial denaturation step of 30 sec at 98° C. followed by 25 cycles with 10 sec at 98° C./20 sec at 50° C./15 sec at 72° C., and a final extension step of 10 minutes at 72° C. The PCR product was separated on a 1% agarose gel, extracted and purified using the Zymoclean™ Gel DNA Recovery Kit (Zymo Research Corporation, Irvine, Calif.).

In a second PCR (PCR2), a 911 bp long fragment of the tagatose-3-epimerase of *Pseudomonas cichorii* ST24 flanked by AscI and SphI sites (underlined in primer sequence) was amplified using:

```
primer EV2962:
                                      (SEQ ID No 14)
AAACTAAAAGGCGCGCCAAAATGAACAAAGTTGGCATG
and primer EV2963:
                                      (SEQ ID No 15)
TTCTCTTCGAGAGCATGCTCAGGCCAGCTTGTCACG.
```

The 5' end of primer EV2962 contains a 9 nucleotide long fragment representing the 3' of the ribulose reductase promoter.

This fragment together with the 8 nucleotides of the AscI site and the following 12 nucleotides of the tagatose-3-epimerase open reading frame, is used for the overlap PCR to fuse the PCR2 product to the previously described PCR1 product.

Additionally, the 5' end of reverse primer EV2963 contains a 12 nucleotide long fragment representing the 5' end of the ribulose reductase terminator of *P. ohmeri*.

This fragment, together with the 6 nucleotides of the SphI site and the following 12 nucleotides of the 3' end of the tagatose-3-epimerase open reading frame, is needed as overlap for fusing PCR2 with the PCR fragment of PCR3 described below.

As template 25 ng of vector 12AAMCJP (FIG. 5) (GeneArt, Regensburg, Germany) containing a synthesized copy of the tagatose-3-epimarease gene of *Pseudomonas cichorii* ST24 was used (nucleotide 719 to 1591 of AB000361.1, from the NCBI GenBank database) SEQ ID No: 11.

The template was amplified in a reaction mix consisting of 200 μM of each dNTP and 0.5 μM of each primer with 0.02 U/μl of iProof™ polymerase (BIO-RAD, Hercules, Calif.) in the appropriate 1× buffer.

The PCR was performed with an initial denaturation step of 30 sec at 98° C. followed by 25 cycles with 10 sec at 98° C./20 sec at 48° C./30 sec at 72° C., and a final extension step of 10 minutes at 72° C.

In a third PCR (PCR3), a 380 bp long fragment of the ribulose reductase terminator of *P. ohmeri* flanked by SphI and SacII sites (underlined in primer sequence) was amplified using:

```
primer EV2964
                                      (SEQ ID No 16)
AAGCTGGCCTGAGCATGCTCTCGAAGAGAATCTAG
and primer EV2965
                                      (SEQ ID No 17)
GTTCCGCGGAGAATGACACGGCCGAC
```

The 5' end of primer EV2964 contains a 12 nucleotide long fragment of the 3' end of the tagatose-3-epimerase open reading frame that, together with the 6 nucleotides of the SphI site and the following 12 nucleotides of the ribulose reductase terminator of *P. ohmeri* is used for the fusion of PCR3 to the previously described PCR2.

Genomic DNA of *P. ohmeri* ATCC 20209 was used as template. After full speed centrifugation, 0.5 μl of the supernatant was used in PCR. For this purpose, a freshly streaked out *P. ohmeri* colony was resuspended in 30 μl of 0.2% SDS and heated for 4 min at 95° C.

The template was amplified in a reaction mix consisting of 200 µM of each dNTP, 0.5 µM of each primer and 0.02 U/µl of iProof™ polymerase (BIO-RAD, Hercules, Calif.) in the appropriate 1× buffer.

The PCR was performed with an initial denaturation step of 30 sec at 98° C. followed by 25 cycles with 10 sec at 98° C./20 sec at 50° C./15 sec at 72° C., and a final extension step of 10 minutes at 72° C. The PCR product was separated on a 1% agarose gel, extracted and purified using the Zymoclean™ Gel DNA Recovery Kit (Zymo Research Corporation, Irvine, Calif.). The PCR product was separated on a 1% agarose gel, extracted and purified using the Zymoclean™ Gel DNA Recovery Kit (Zymo Research Corporation, Irvine, Calif.).

Fusion of the three individual PCR fragments was performed as follows: 50 ng of each gel purified product of PCR1 and PCR2 was used as template in a PCR reaction with EV2960 and EV2963.

A 30 nucleotide long homologous segment in the two fragments, resulting from the primer design described above, was used as overlap in the fusion reaction.

This way, a 1.4 kb long fragment, consisting of a ribulose reductase promoter of *P. ohmeri* flanked by SpeI and AscI sites was fused to the open reading frame of the tagatose-3-epimerase of *Pseudomonas cichorii* ST24.

The templates were amplified in a reaction mix consisting of 200 µM of each dNTP, 0.5 µM of each primer and 0.02 U/µl of iProof™ polymerase (BIO-RAD, Hercules, Calif.) in the appropriate 1× buffer.

The PCR was performed with an initial denaturation step of 30 sec at 98° C., followed by 30 cycles with 10 sec at 98° C./20 sec at 62° C./45 sec at 72° C., and a final extension step of 10 minutes at 72° C. The PCR product was separated on a 1% agarose gel, extracted and purified using the Zymoclean™ Gel DNA Recovery Kit (Zymo Research Corporation, Irvine, Calif.).

The purified fragment was fused in a second overlap PCR to the product of PCR3. 40 ng of each fragment was used as template and amplified with EV2960 and EV2965.

A 30 nucleotide long homologous segment in the two fragments, resulting from the primer design described above, was used as overlap in the fusion.

This way, a 1.8 kb long fragment, consisting of a ribulose reductase promoter of *P. ohmeri* flanked by SpeI and AscI and the open reading frame of the tagatose-3-epimerase of *Pseudomonas cichorii* ST24 flanked by AscI and SphI sites was fused to the ribulose reductase terminator of *P. ohmeri*.

The templates were amplified in a reaction mix consisting of 200 µM of each dNTP, 0.5 µM of each primer and 0.02 U/µl of iProof™ polymerase (BIO-RAD, Hercules, Calif.) in the appropriate 1× buffer.

The PCR was performed with an initial denaturation step of 30 sec at 98° C. followed by 30 cycles with 10 sec at 98° C./20 sec at 65° C./55 sec at 72° C., and a final extension step of 10 minutes at 72° C. The PCR product was separated on an agarose gel, extracted and purified using the Zymoclean™ Gel DNA Recovery Kit (Zymo Research Corporation, Irvine, Calif.).

The final PCR product consisting of a 1.7 kb long fragment of the tagatose-3-epimerase of *Pseudomonas cichorii* ST24 flanked by a ribulose reductase promoter and terminator was digested with restriction enzymes SpeI and SacII (New England Biolabs, Ipswich, Mass.), gel purified and ligated overnight at 16° C. with a 9.8 kb long isolated SpeI/SacII fragment of a lig7.78 vector backbone using T4 DNA ligase (New England Biolabs. Ipswich, Mass.) (FIG. 6).

After transformation of XL.10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.). The purified plasmid DNA was used for further characterization by restriction digestion and sequencing (Microsynth, Balgach, Switzerland).

The newly cloned expression plasmid pEVE2523 (FIG. 7) is a shuttle *E. coli-P. ohmeri* vector consisting of a bacterial (*E. coli*) origin of replication and an ampicillin resistance gene, the yeast (*P. ohmeri*) autonomous replication sequence, and the poURA3 (*P. ohmeri*) gene for selection in yeast.

Moreover, it contains an exchangeable *P. ohmeri* ribulose reductase promoter element (via SpeI and AscI restriction) and terminator element (via SphI and SacII) flanking an open reading frame of the tagatose-3-epimerase of *Pseudomonas cichorii* (exchangeable via AscI and SphI restriction).

Example 7. Construction of a *P. ohmeri* Vector for Heterologous Gene Expression Using the poLEU2 Selection Marker For the construction of a second *P. ohmeri* expression vector, the expression cassette of plasmid pEVE2523 (FIG. 7) described previously in Example 6 was cloned into a vector containing the *P. ohmeri* poLEU2 selection marker (FIG. 6).

A blunted 1.7 kb fragment of vector pEVE2523 (FIG. 7) cut with SpeI and SacII (New England Biolabs, Ipswich, Mass.) was used as insert. Blunting was performed with the Blunting Enzyme Mix (New England Biolabs, Ipswich, Mass.) for 15 min at room temperature, followed by heat inactivation of the enzymes for 10 min at 70° C.

The vector backbone was obtained from a poARS vector (plig3-FR 2772788) linearized with SalI (New England Biolabs, Ipswich, Mass.), blunted and dephosphorylated for 1 h at 37° C. using Antarctic phosphatase (New England Biolabs, Ipswich, Mass.). Gel purified insert and vector backbone using Zymoclean™ Gel DNA Recovery Kit (Zymo Research Corporation, Irvine, Calif.) were ligated for 1 h at RT using T4 DNA ligase (New England Biolabs, Ipswich, Mass.).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and used for further characterization by restriction digestion and sequencing (Microsynth, Balgach, Switzerland).

The new cloned expression plasmids pEVE2560 (FIG. 8) is a shuttle *E. coli-P. ohmeri* vector containing a bacterial (*E. coli*) origin of replication and an ampicillin resistance gene, the yeast (*P. ohmeri*) autonomous replication sequence, and the poLEU2 (*P. ohmeri*) gene for selection in yeast.

Moreover, the open reading frame of the tagatose-3-epimerase of *Pseudomonas cichorii* flanked by a *P. ohmeri* ribulose reductase promoter and terminator is exchangeable via AscI and SphI restriction.

Example 8. Construction of a *P. ohmeri* Vector for Overexpression of *Gluconobacter oxydans* NADPH-Specific Xylitol Dehydrogenase A *P. ohmeri* vector for overexpression of *Gluconobacter oxydans* NADPH-specific xylitol dehydrogenase was constructed.

For cloning into the expression vector, the DNA fragment encoding the *Gluconobacter oxydans* NADPH-specific xylitol dehydrogenase was released from vector 13AAYSYP (FIG. 3) by cutting with AscI and SphI restriction enzymes (New England Biolabs, Ipswich, Mass.).

The 803 bp fragment was gel-purified using Zymoclean™ Gel DNA Recovery Kit (Zymo Research Corporation, Irvine, Calif.) and ligated for 2 h at room temperature to the 9.8 kb AscI/SphI-digested and gel-purified vector backbone of pEVE2523 (FIG. 7) using T4 DNA ligase (New England Biolabs, Ipswich, Mass.) (FIG. 9).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3284 (FIG. 10) contains the codon-optimized NADPH-specific xylitol dehydrogenase of *Gluconobacter oxydans* flanked by a ribulose reductase promoter and terminator of *P. ohmeri* and the poURA3 selection marker.

Example 9. Construction of a *P. ohmeri* Vector for Overexpression of *Pichia stipitis* NADPH-Specific Xylitol Dehydrogenase For sub-cloning into the expression vector, the DNA fragment encoding the NADPH-specific xylitol dehydrogenase from *Pichia stipitis* had to be flanked with AscI and SphI restriction sites.

For this purpose:

```
EV3101 primer
                                         (SEQ ID No 18)
AAGGCGCGCCAAA ATGACTGCTAACCCTTCC containing an AscI site (underlined)
and EV3102 primer
                                         (SEQ ID No 19)
GAGCATGCTTACTCAGGGCCGTCAATG containing a SphI (underlined)
``` were used in a PCR reaction with 30 ng of vector 12AALQTP (FIG. 2B) as template.

The template was amplified in a reaction mix consisting of 200 µM of each dNTP and 0.5 µM of each primer with 0.02 U/µl iProof™ polymerase (BIO-RAD, Hercules, Calif.) in the appropriate 1× buffer.

The PCR was performed with an initial denaturation step of 30 sec at 98° C. followed by 25 cycles with 10 sec at 98° C./20 sec at 55° C./30 sec at 72° C., and a final extension step of 10 minutes at 72° C.

The 1.1 kb PCR product was separated on a 1% agarose gel, extracted, purified using the Zymoclean™ Gel DNA Recovery Kit (Zymo Research Corporation, Irvine, Calif.) and restriction digested with AscI and SphI (New England Biolabs, Ipswich, Mass.). After column purification with the DNA Clean & Concentrator™-5 Kit (Zymo Research Corporation, Irvine, Calif.), it was ligated for 2 h at room temperature to the 10.6 kb AscI/SphI-digested and gel-purified vector backbone of pEVE2523 (FIG. 7) and the 11.8 kb AscI/SphI-digested and gel-purified vector backbone of pEVE2560 (FIG. 8) respectively, using T4 DNA ligase (New England Biolabs, Ipswich, Mass.) (FIG. 11).

After transformation of XL10 Gold ultracompetent cells (Agilent Technologies, Santa Clara, Calif.) with the ligation mixture, plasmid DNA was isolated and further characterized by restriction digestion and sequencing (Microsynth, Balgach, Switzerland).

The resulting plasmids pEVE2562 and pEVE2564 (FIG. 12) contain the codon optimised NADPH-specific xylitol dehydrogenase of *Pichia stipitis* flanked by a ribulose reductase promoter and terminator of *P. ohmeri* and either the poURA3 or poLEU2 selection marker, respectively.

Example 10. Construction of a *P. ohmeri* Vector for Overexpression of *Pichia stipitis* NADH-Specific Xylitol Dehydrogenase For sub-cloning into the expression vector, the DNA fragment encoding the NADH-specific xylitol dehydrogenase from *Pichia stipitis* had to be flanked with AscI and SphI restriction sites.

For this purpose:

```
EV3101
                                         (SEQ ID No 18)
(AAGGCGCGCCAAA ATGACTGCTAACCCTTCC)

containing an AscI site (underlined)
and

EV3102
                                         (SEQ ID No 19)
(GA GCATGCTTACTCAGGGCCGTCAATG)

containing a SphI (underlined)
``` were used in a PCR reaction with 30 ng of vector lig7.78 (FIG. 2A) as template.

The template was amplified in a reaction mix consisting of 200 µM of each dNTP and 0.5 µM of each primer with 0.02 U/µl iProof™ polymerase (BIO-RAD, Hercules, Calif.) in the appropriate 1× buffer.

The PCR was performed with an initial denaturation step of 30 sec at 98° C. followed by 25 cycles with 10 sec at 98° C./20 sec at 55° C./30 sec at 72° C., and a final extension step of 10 minutes at 72° C.

The 1.1 kb PCR product was separated on a 1% agarose gel, extracted, purified using the Zymoclean™ Gel DNA Recovery Kit (Zymo Research Corporation, Irvine, Calif.) and restriction digested with AscI and SphI (New England Biolabs, Ipswich, Mass.).

After column purification with the DNA Clean & Concentrator™-5 Kit (Zymo Research Corporation, Irvine, Calif.), it was ligated for 2 h at room temperature to the 10.5 kb AscI/SphI-digested and gel-purified vector backbone of pEVE2560 (FIG. 8) using T4 DNA ligase (New England Biolabs, Ipswich, Mass.) (FIG. 13).

After transformation of XL10 Gold uitracompetent cells (Agilent Technologies, Santa Clara, Calif.) with the ligation mixture, plasmid DNA was isolated and further characterized by restriction digestion and sequencing (Microsynth, Balgach, Switzerland).

The resulting plasmid pEVE2563 (FIG. 14) contains the codon optimised NADH-specific xylitol dehydrogenase of *Pichia stipitis* flanked by a ribulose reductase promoter and terminator of *P. ohmeri* and the poLEU2 selection marker.

Example 11. Construction of *P. ohmeri* Vectors for Overexpression of *E. coli* NAD$^+$-Specific D-Arabitol 4-Oxidoreductase A *P. ohmeri* vector for overexpression of *E. coli* NAD$^+$-specific D-arabitol 4-oxidoreductase was constructed.

For cloning into the expression vector, the DNA fragment encoding the codon-optimised *E. coli* NAD$^+$-specific D-arabitol 4-oxidoreductase was released from vector 12ABY-WMP (FIG. 1) by cutting with AscI and SphI restriction enzymes (New England Biolabs, Ipswich, Mass.).

The 1.4 kb fragment was gel-purified using Zymoclean™ Gel DNA Recovery Kit (Zymo Research Corporation, Irvine, Calif.) and ligated for 2 h at room temperature to the 9.8 kb AscI/SphI-digested and gel-purified vector backbone of pEVE2523 (FIG. 7) using T4 DNA ligase (New England Biolabs, Ipswich, Mass.) (FIG. 15).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2839 (FIG. 16) contains the codon-optimised *E. coli* NAD$^+$-specific D-arabitol 4-oxidoreductase flanked by a ribulose reductase promoter and terminator of *P. ohmeri* and the poURA3 selection marker.

In addition to the *P. ohmeri* ribulose reductase promoter, the NAD$^+$-specific D-arabitol 4-oxidoreductase from *E. coli* was also cloned under the control of the *P. ohmeri* phosphoglycerate kinase (poPGK1) promoter and transketolase (poTKL) terminator.

Cloning was performed in two consecutive steps, by first replacing the ribulose reductase promoter by the poPGK1 promoter, followed by an exchange of the ribulose reductase terminator for the poTKL terminator.

A 611 bp long fragment of the *P. ohmeri* poPGK1 promoter was amplified from genomic DNA of *P. ohmeri* using:

```
primer EV3177
                                  (SEQ ID No 20)
(GAAGACTAGTTCACGTGATCTC) containing a SpeI site (underlined)
and primer EV3178
                                  (SEQ ID No 21)
(CACT GGCGCGCCTTTTGTGTGGTGGTGTCC), containing an AscI site (underlined).
```

The genomic DNA template was prepared by resuspending a freshly streaked out *P. ohmeri* colony in 30 µl of 0.2% SDS and heating for 4 min at 95° C. After full speed centrifugation, 0.5 µl of the supernatant was used for PCR.

Amplification was performed in a reaction mix consisting of 200 µM of each dNTP and 0.5 µM of each primer with 0.02 U/µl of iProof™ polymerase (BIO-RAD, Hercules, Calif.) in the appropriate 1× buffer.

The PCR was accomplished with an initial denaturation step of 2 min at 96° C. followed by 25 cycles with 10 sec at 96° C./10 sec at 58° C./30 sec at 72° C., and a final extension step of 2 minutes at 72° C.

The PCR product was separated on a 1% agarose gel, extracted and purified using the Zymoclean™ Gel DNA Recovery Kit (Zymo Research Corporation, Irvine, Calif.).

The amplified 610 bp long poPGK1 promoter fragment was restriction digested with SpeI and AscI (New England Biolabs, Ipswich, Mass.) and ligated for 2 h at room temperature to the 11.5 kb SpeI/AscI-digested and gel-purified vector backbone of pEVE2839 (FIG. 16) using T4 DNA ligase (New England Biolabs, Ipswich, Mass.) (FIG. 17).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3102 (FIG. 18) contains the codon-optimised *E. coli* NAD$^+$-specific D-arabitol 4-oxidoreductase flanked by a phosphoglycerate kinase (poPGK1) promoter and ribulose reductase terminator of *P. ohmeri* and the poURA3 selection marker.

In the next step the ribulose reductase terminator of pEVE3102 was exchanged for the tranketolase (poTKL) terminator of *P. ohmeri*.

A 213 bp long fragment of the *P. ohmeri* poTKL terminator was amplified from genomic DNA of *P. ohmeri* using:

```
primer EV3817
                                  (SEQ ID No 22)
(TAGCAGCATGCATAGGTTAGTGAATGAGGTATG)

containing a SphI site (underlined)
and (SEQ ID No 23)
primer EV3818 (TAGGTCCGCGGGAGCTTCGTTAAAGGGC)

containing a SacII site (underlined).
```

The genomic DNA template was prepared as described above.

Amplification was performed in a reaction mix consisting of 200 µM of each dNTP and 0.5 µM of each primer with 0.02 U/µl of iProof™ polymerase (BIO-RAD, Hercules, Calif.) in the appropriate 1× buffer.

The PCR was accomplished with an initial denaturation step of 2 min at 96° C. followed by 25 cycles with 10 sec at 96° C./10 sec at 57° C./30 sec at 72° C., and a final extension step of 2 minutes at 72° C. The PCR product was separated on a 1% agarose gel, extracted and purified using the Zymoclean™ Gel DNA Recovery Kit (Zymo Research Corporation, Irvine, Calif.).

The amplified 213 bp long poTKL terminator fragment was restriction digested with SphI and SacII (New England Biolabs, Ipswich, Mass.) and ligated for 2 h at room temperature to the 11.5 kb SphI/SacII-digested and gel-purified vector backbone of pEVE3102 (FIG. 18) using T4 DNA ligase (New England Biolabs, Ipswich, Mass.) (FIG. 17).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3123 (FIG. 19) contains the codon-optimised *E. coli* NAD$^+$-specific D-arabitol 4-oxidoreductase flanked by a phosphoglycerate kinase (poPGK1) promoter and a transketolase (poTKL) terminator of *P. ohmeri* and the poURA3 selection marker.

In order to be able to express the NAD$^+$-specific D-arabitol 4-oxidoreductase of *E. coli* from a plasmid using another selection, the poURA3 marker of pEVE3123 was exchanged for the poLEU2 marker.

For this purpose the poURA3 marker was released from vector pEVE3123 (FIG. 19) by restriction digestion with PsiI and AfeI (New England Biolabs, Ipswich, Mass.).

The 9.1 kb vector backbone was gel-purified using Zymoclean™ Gel DNA Recovery Kit (Zymo Research Corporation, Irvine, Calif.), blunted with the Blunting Enzyme Mix kit (New England Biolabs, Ipswich, Mass.) for 15 min at room temperature, followed by heat inactivation of the enzymes for 10 min at 70° C. and dephosphorylated for 1 h at 37° C. using Antarctic phosphatase (New England Biolabs, Ipswich, Mass.).

As insert, a 3 kb blunted and gel-purified fragment of the poLEU2 marker released from vector pEVE2560 (FIG. 8) by AseI and AfeI restriction digestion was used, Ligation of the fragments was performed for 2 h at room temperature using T4 DNA ligase (New England Biolabs, Ipswich, Mass.) (FIG. 20).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3157 (FIG. 21) contains the codon-optimised E. coli NAD-specific D-arabitol 4-oxidoreductase flanked by a phosphoglycerate kinase (poPGK1) promoter and a transketolase (poTKL) terminator of P. ohmeri and the poLEU2 selection marker.

Example 12. Expression of the Plasmidic E. coli NAD$^+$-Specific D-arabitol 4-Oxidoreductase and of the Plasmidic Pichia stipitis NADPH-Specific Xylitol Dehydrogenase Gene in Pichia ohmeri Strain ATCC 20209

For the biosynthetic conversion of arabitol into xylitol, the simultaneous expression of the NAD$^+$-specific E. coli D-arabitol 4-oxidoreductase and the NADP-specific xylitol dehydrogenase of P. stipitis is necessary.

The first enzyme leads to the formation of xylulose and the second ones convert xylulose into xylitol.

P. ohmeri strain SRLU (MATh$^-$ leu2 ura3) derived from ATCC 20209 and auxotrophic for leucine and uracil (Piredda and Gaillardin, 1994, supra) was used as host for the construction of a yeast strains secreting xylitol by transformation with plasmids:
pEVE2839 (NAD$^+$-specific D-arabitol 4-oxidoreductase of E. coli) and
pEVE2564 (NADPH-specific xylitol dehydrogenase of P. stipitis)
leading to strain EYS2755
Additionally, as a control (following the teaching of WO 94/10325) a strain expressing the NADH-specific wild type xylitol dehydrogenase of P. stipitis was also constructed by transformation with plasmids:
pEVE2839 (NAD$^+$-specific D-arabitol 4-oxidoreductase of E. coli) and
pEVE2563 (NADH-specific xylitol dehydrogenase of P. stipitis)
into the SRLU host, leading to strain EYS2962.
As control, strains transformed with the single plasmids:
pEVE2839 (NAD$^+$-specific D-arabitol 4-oxidoreductase of E. coli),
pEVE2563 (NADH-specific xylitol dehydrogenase of P. stipitis), and
pEVE2564 (NADPH-specific xylitol dehydrogenase of P. stipitis)
leading to EYS2943, EYS2696 and EYS2697 respectively, were also generated.

Yeast transformation was carried out in essential by the spheroplasting method of Green et al. (Green E D., Hieter, P., and Spencer F. A., chapter 5 in Genome Analysis: A Laboratory Manual, Vol. 3, Cloning Systems, Birren et al. (eds.), Cold Spring Harbor Press, New York, 1999) with the following modifications: Instead of Lyticase, Zymolyase 100T was used for generation of spheroplasts and the incubation with the enzyme was performed at 37° C. until the OD of the cell suspension reached 20-30% of the original OD before Zymolyase treatment.

Briefly, P. ohmeri cells were grown overnight at 30° C. in YPD medium (Yeast extract 1% (w/v), Peptone 2% (w/v), Dextrose 2% (w/v)) to a final OD$_{600}$ of 3-5.

200 OD$_{600}$ units were harvested by centrifugation, washed once with water and 1M sorbitol, and resuspended in SCE buffer (1 M sorbitol, 100 mM citric acid trisodium salt dihydrate, 10 mM EDTA) to a final concentration of 70 ODs/ml.

DTT and Zymolase (LuBio Science, Luzern, Switzerland) were added to a final concentration of 10 mM and 0.5 U/OD, respectively and the mixture incubated at 37° C. with slow shaking.

The cell wall digestion was followed by measuring the optical density of the solution diluted in water. When this value dropped to 80% of the original, the digestion was terminated by careful centrifugation and washing with 1 M sorbitol and STC buffer (0.98 M sorbitol, 10 mM Tris pH 7.5, 10 mM CaCl$_2$).

Speroplasts were carefully resuspended in STC buffer containing 50 µg/ml calf-thymus DNA (Calbiochem/VWR, Dietikon, Switzerland) to a final concentration of 200 OD/ml. Aliquots of 100 µl were mixed with 100-200 ng of plasmid DNA and incubated for 10 min at room temperature.

1 ml PEG solution (19.6% PEG 8000 w/v, 10 mM Tris pH 7.5, 10 mM CaCl$_2$) was added to the suspension, incubated for 10 minutes and pelleted. Spheroplasts were regenerated at 30° C. for 1-2 h in 1 ml of a 1 M sorbitol solution containing 25% YPD and 7 mM CaCl$_2$.

To the regenerated cells 7 ml of 50° C. warm top agar (0.67% yeast nitrogen base w/o amino acids, 0.13% drop-out powder without leucine/uracil/histidine/tryptophan/methionine, 0.086%$_0$ of required missing amino acid, 2% glucose, 1 M sorbitol, pH5.8 and 2.5% Noble agar) was added and the mixture was poured evenly onto pre-warmed, sorbitol containing selective plates (0.67% yeast nitrogen base w/o amino acids, 0.13% drop-out powder without leucine/uracil/histidine/tryptophan/methionine, 0.086% of required missing amino acid, 2% glucose, 1 M sorbitol, pH5.8).

Plates were incubated for 3-5 days at 30° C. Transformants were reselected on the appropriate selective plates.

Each generated strain was tested in triplicates for arabitol, xylitol and ribitol production.

For this purpose clones were first grown at 30° C. overnight in seed media (0.67% yeast nitrogen base without amino acids; 0.13% drop-out powder without leucine/uracil/histidine/tryptophan/methionine; 0.086%$_0$ of required missing amino acid; 5% glucose; pH5.7).

Out of this overnight culture a main culture in production media (0.67% yeast nitrogen base without amino acids; 0.13% drop-out powder without leucine/uracil/histidine/tryptophan/methionine; 0.086%$_0$ of required missing amino acid; 15% glucose; pH5.7) at a starting OD600 of 0.2 was inoculated.

This culture was grown at 37° C. for 48 hours and the arabitol, xylitol and ribitol concentrations of the supernatants were determined by HPLC/MS using a Aminex® HPX-87 column (Bio-Rad, Hercules, Calif.) and a Waters® TQ-Detector (Acquity® UPLC linked to a triple quadrupol detector, Waters, Milford, Mass.) and isocratic conditions with 100% water as mobile phase.

Polyol titers of all tested strains are depicted in Table 8.

TABLE 8

Polyol production of *P. ohmeri* SRLU strains transformed with NADH- and NADPH-specific xylitol dehydrogenase of *P. stipitis* and/or with NAD+-specific D-arabitol 4-oxidoreductase of *E. coli* (average of triplicates)

| Strain | Arabitol (g/L) | Xylitol (g/L) | Ribitol (g/L) |
|---|---|---|---|
| SRLU | 32.9 ± 2.4 | nd | nd |
| EYS2943 [pEVE2839] | 26.4 ± 2.8 | 2.3 ± 0.1 | 0.7 ± 1.2 |
| EYS2696 [pEVE2563] | 36.0 ± 2.7 | nd. | 0.8 ± 0.1 |
| EYS2697 [pEVE2564] | 31.1 ± 1.6 | nd | 6.3 ± 0.1 |
| EYS2962 [pEVE2839/ pEVE2563] | 29.6 ± 0.8 | 7.0 ± 0.3 | 2.3 ± 0.1 |
| EYS2755 [pEVE2839/ pEVE2564] | 16.4 ± 2.2 | 19.9 ± 0.8 | 10.9 ± 0.4 | nd—not detected

Use of the NADPH-specific xylitol dehydrogenase of *P. stipitis* leads to a significant increase in xylitol titers, as compared to the wild type NADH-specific enzyme.

Example 13. Expression of the Plasmidic *Gluconobacter oxydans* NADPH-Specific Xylitol Dehydrogenase Gene in *Pichia ohmeri*

In addition to a xylitol producing strain using the NADP-specific xylitol dehydrogenase of *P. stipitis* a second strain expressing the NADP-specific xylitol dehydrogenase of *G. oxydans* was engineered.

*P. ohmeri* strain SRLU (MATh− leu2 ura3) derived from ATCC 20209 and auxotrophic for leucine and uracil (Piredda and Gaillardin, 1994, supra) was used as host for the construction of a yeast strains secreting xylitol by transformation with plasmids pEVE3157 (NAD+-specific D-arabitol 4-oxidoreductase of *E. coli*) and pEVE3284 (NADPH-specific xylitol dehydrogenase of *G. oxydans*) leading to strain EYS3324.

As control, strains transformed with the single plasmids:
pEVE3157 (NAD+-specific D-arabitol 4-oxidoreductase of *E. coli*) and
pEVE3284 (NADH-specific xylitol dehydrogenase of *G. oxydans*), leading to EYS3067 and EYS3323 respectively, were also generated.

The *E. coli* D-arabitol 4-oxidoreductase used for the construction of the above strains is controlled by poPGK1 promoter in contrast to the poRR promoter used in strains expressing the xylitol dehydrogenase of *P. stipitis*.

However, to exclude a promoter influence and therefore, to be able to compare polyol levels in strains expressing the xylitol dehydrogenase from *G. oxydans* with those expressing the corresponding enzyme from *P. stipitis*, an additional strain has been generated.

This strain EYS2963 was obtained by transforming the SRLU host with
pEVE3123 (NAD+-specific D-arabitol 4-oxidoreductase of *E. coli*) and
pEVE2564 (NADPH-specific xylitol dehydrogenase of *P. stipitis*).

Yeast transformation was carried out as described in Example 12. Each generated strain was tested in triplicates for arabitol, xylitol and ribitol production as described in Example 12.

Polyol titers of all tested strains are depicted in Table 9.

TABLE 9

Polyol production of *P. ohmeri* SRLU strains transformed with NADPH-specific xylitol dehydrogenase of *G. oxydans* and/or with NAD+-specific D-arabitol 4-oxidoreductase of *E. coli* (average of triplicates)

| Strain | Arabitol (g/L) | Xylitol (g/L) | Ribitol (g/L) |
|---|---|---|---|
| SRLU | 32.9 ± 2.4 | nd | nd |
| EYS3067 [pEVE3157] | 29.0 ± 3.8 | 1.5 ± 0.3 | 1.8 ± 0.4 |
| EYS3323 [pEVE3284] | 32.8 ± 0.6 | nd | nd |
| EYS3324 [pEVE3157/ pEVE3284] | 26.3 ± 1.7 | 21.1 ± 1.1 | 1.2 ± 0.1 |
| EYS2963 [pEVE3123/ pEVE2564] | 27.3 ± 2.5 | 17.7 ± 1.7 | 13.9 ± 0.7 | nd—not detected

Xylitol titers in strains expressing the NADPH-specific xylitol dehydrogenase from *G. oxydans* (EYS3324) are similar to those of strains expressing the corresponding enzyme from *P. stipitis* (EYS2963). However, the *G. oxydans* enzyme leads to much lower ribitol titers, thus showing a higher substrate specificity towards xylulose.

Example 14. Generation of a Mutant *P. ohmeri* Strain with Increased Arabitol Secretion A higher arabitol producer mutant has been selected from an UV irradiated suspension of *P. ohmeri* ATCC 20209.

The UV-irradiation system (Vilber Lourmat, France), was equipped with a microprocessor-controlled RMX-3 W radiometer. *P. ohmeri* was grown on YPD agar (Dextrose 20 g/L) at 37° C. overnight.

A suspension was prepared to reach $10^6$ cfu/mL ($OD_{620}$=0.4) and 5 mL were put into a sterile Petri dish. The suspension was irradiated after removing the cover from the dish. The UV wavelength was 254 nm and the irradiation energy was $1.8 \cdot 10^{-2}$ J/cm². 90% of mortality of the yeast cells was obtained. After stopping the irradiation and replacing the lid on the dish, the suspension was transferred into a sterile tube located into an iced bath.

20 mL of YPD liquid medium was inoculated with the mutated suspension and was incubated for 12 hours at 37° C., 250 rpm.

After incubation the mutated culture was diluted with sterile 40% glycerol (V/V). Aliquots were distributed into 5 mL vials and frozen at −80° C.

The screening was based on the osmophilic property of *Pichia ohmeri* which is able to grow on very high concentrations of Dextrose (up to 600 g/L).

Our goal was to select mutants able to grow faster than the mother strain on YPD agar containing Dextrose 600 g/L or 700 g/L.

Defrosted aliquots were spread on $YPD_{600}$ and $YPD_{700}$ and the first appearing colonies were selected and tested for the production of arabitol in shake flasks.

The subculture and production medium were made of glucose 50 g/L or 100 g/L respectively, yeast extract 3 g/L, $MgSO_4$ 1 g/L and $KH_2PO_4$ 2 g/L, pH 5.7. The subculture (10 mL in a 100 mL flask) was incubated for 24 h at 37° C., 250 rpm. The production (40 mL in a 500 mL flask) was inoculated by 5 mL of subculture and incubated for 64 hours at 37° C., 250 rpm.

| | Glucose g/L 64 h | Arabitol g/L 64 h |
|---|---|---|
| P. ohmeri ATCC 20209 | 6.0 | 52.7 |
| P. ohmeri CNCM I-4605 | 0 | 58.6 |

The mutant P. ohmeri strain was selected for its faster consumption of glucose and its higher production of arabitol and was deposited in France on Mar. 7, 2012, with the Collection Nationale de Cultures de Microorganismes [National Collection of Microorganism Cultures] of the Institut Pasteur (CNCM), 25 rue du Docteur Roux, 75724 PARIS Cedex 15, under number 1-4605.

Example 15. Construction of a LEU2 Deletion Plasmid

In order to be able to use the newly generated CNCM I-4605 strain for plasmid selection and gene integrations, a plasmid for the deletion of the LEU2 open reading frame was constructed.

In a first step, a general integration vector that can be used in P. ohmeri was adapted from the S. cerevisiae CRE/loxP system. The vector backbone was isolated from pUG73 (Gueldener et al., 2002, *Nucleic Acid Res*, 30, e23) by restriction cutting with PstI and EcoRV enzymes (New England Biolabs, Ipswich, Mass.).

As insert served a PCR fragment containing a LEU2 selection marker of P. ohmeri flanked by loxP sites, generated with primer pair:

```
EV3043
                                            (SEQ ID No 24)
(CACTGGCGCGCCCACTGCATGCGTCGACAACCCTTAATATAACTTCGTA

TAATGTATGCTATACGAAGTTATTAGGTCTAGACACATCGTGGATCCAAG

CTATCAACGAGAGAGTC)
and

EV3044
                                            (SEQ ID No 25)
(AGTGGCTAGCAGTGCCATGGCCTAATAACTTCGTATAGCATACATTATA

CGAAGTTATATTAAGGGTTCTCGAGACGCGTCATCTAGCATCTCATCTAC

CAACTC)
and poARS (plig3 - FR 2772788 - see FIG. 6) as template.
```

The forward primer EV3043 contains an AscI (underlined) site preceding a SphI site (underlined), followed by a 48 bp long loxP fragment (bold) and a DraIII site (underlined). The 3' end of EV3043 contains an additional a 25 bp long fragment for amplification of the P. ohmeri LEU2 gene. The reversed primer EV3044 on the other hand, contains a NheI (underlined) site preceding a NcoI site (underlined), followed by a 48 bp long loxP fragment (bold) and a MluI site (underlined). The 3' end of EV3044 contains an additional a 25 bp long fragment for amplification of the P. ohmeri LEU2 gene. The template was amplified in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was performed with an initial denaturation step of 30 sec at 98° C. followed by 30 cycles with 10 sec at 98° C./10 sec at 65° C./50 sec at 72° C., and a final extension step of 7 minutes at 72° C. The PCR product was separated on a 1% agarose gel, extracted and purified using the Zymoclean™ Gel DNA Recovery Kit (Zymo Research Corporation, Irvine, Calif.)

The amplified fragment was flanked by a PstI and EcoRV site in a second PCR reaction for further subcloning. Amplification was performed with:

```
primer EV3056
                                            (SEQ ID No 26)
(CACTCTGCAGCACTGGCGCGCCCACTGCAT)

containing the PstI site (underlined)
and primer EV3057
                                            (SEQ ID No 27)
(CACTGATATCAGTGGCTAGCAGTGCCATGG)

containing the EcoRV site (underlined)
``` in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was accomplished with an initial denaturation step of 30 sec at 98° C. followed by 30 cycles with 10 sec at 98° C./45 sec at 72° C., and a final extension step of 7 minutes at 72° C. The PCR product was separated on a 1% agarose gel, extracted and purified using the Zymoclean™ Gel DNA Recovery Kit (Zymo Research Corporation, Irvine, Calif.).

The amplified 2.5 kb LEU2 marker was restriction digested with PstI and EcoRV enzymes (New England Biolabs, Ipswich, Mass.), gel-purified with the Zymoclean™ Gel DNA Recovery Kit (Zymo Research Corporation, Irvine, Calif.) and ligated for 2 h at room temperature to the 2.4 kb PstI/EcoRV (New England Biolabs, Ipswich, Mass.), gel-purified (Zymoclean™ Gel DNA Recovery Kit—Zymo Research Corporation, Irvine, Calif.) backbone of vector pUG73 (Gueldener et al., 2002 *Nucleic Acid Res*, 30, e23) using T4 DNA ligase (New England Biolabs, Ipswich, Mass.) (FIG. 22). After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2787 (FIG. 23) contains the P. ohmeri LEU2 selection marker under the control of the endogenous promoter and terminator, flanked by two loxP sites. Additionally, a AscI and SphI site have been introduced upstream of the first loxP and a NheI and NcoI site downstream of the second loxP, in order to help in cloning of regions homologous to the integration sites in the genome.

The LEU2 marker of the integration vector was then replaced by the nat1 resistance gene of Streptomyces noursei, in a second cloning step, since a deletion of the endogenous LEU2 open reading frame was aimed.

A DNA fragment encoding the nat1 gene of Streptomyces noursei was chemically synthesized by GeneArt® Gene Synthesis (Life Technologies, Regensburg, Germany) according to the submitted sequence of SEQ ID No 28.

Nucleotides 204 to 776 of sequence S60706.1 (obtained from the NCBI GenBank database) coding for the nat1 gene were used as template and subjected to codon optimization for use in P. ohmeri ATCC 20209 according to Table 7 (above), using the Optimizer program.

At the 5' and 3' ends of the resulting sequence, nucleotides encoding for the recognition sites of the restriction enzymes AscI (GGCGCGCC) and SphI (GCATGC) respectively, were manually added in the text file, in order to facilitate further cloning. Additionally, an adenosine triplet was included in front of the start ATG to account for an adenosine at the −3 position in the Kozak-like sequence of yeasts.

The final sequence (SEQ ID No 28) was then submitted for synthesis to GeneArt (Regensburg, Germany). The synthesized DNA fragment encoding the nat1 gene was delivered as 5 µg lyophilized plasmid DNA in a pMA-T derived vector (12ABTV4P, FIG. 24).

For the cloning of the net gene a vector containing a ribulose reductase (poRR) promoter and terminator was used. The terminator was exchanged by an orotidine-5'-phosphate decarboxylase (poURA3) terminator and the nat1 gene was introduced between the promoter and terminator sequences.

For this purpose, the orotidine-5'-phosphate decarboxylase (poURA3) terminator was generated by PCR with:

```
primer EV3393
                                        (SEQ ID No 29)
(CAAGCATGCGGGAATGATAAGAGACTTTG)
containing a SphI site (underlined)
and primer EV3394
                                        (SEQ ID No 30)
(GGACCGCGGAAAGGTGAGGAAGTATATGAAC)

containing a SacII site (underlined)
and pEVE2523 (FIG. 7) as template.
```

Amplification was performed in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was accomplished with an initial denaturation step of 30 sec at 98° C. followed by 30 cycles with 10 sec at 98° C./10 sec at 59° C./10 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.). The 239 bp poURA3 terminator was restriction digested with SphI and SacII enzymes (New England Biolabs, Ipswich, Mass.) and ligated for 2 h at room temperature to the 11 kb vector backbone of pEVE2681 linearized with SphI and SacII restriction enzymes (New England Biolabs, Ipswich, Mass.) and gel-purified with Zymoclean™ Gel DNA Recovery Kit (Zymo Research Corporation, Irvine, Calif.) using T4 DNA ligase (New England Biolabs, Ipswich, Mass.). After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

In a second cloning step, the nat1 gene was released from 12ABTV4P (FIG. 24) by restriction cutting with SphI and AscI enzymes (New England Biolabs, Ipswich, Mass.). Additionally, a blunting of the SphI site with the Blunting Enzyme Mix kit (New England Biolabs, Ipswich, Mass.) for 15 min at room temperature, followed by heat inactivation of the enzymes for 10 min at 70° C. was performed in between the SphI and AscI digestion. The 587 bp gel-purified fragment (Zymoclean™ Gel DNA Recovery Kit—Zymo Research Corporation, Irvine, Calif.) was than ligated to the gel-purified 10.5 kb vector backbone of the vector described above cut with SphI and AscI restriction enzymes (New England Biolabs, Ipswich, Mass.).

Also the SphI site of the vector was blunted for 15 min at room temperature with the Blunting Enzyme Mix kit (New England Biolabs, Ipswich, Mass.), followed by a heat inactivation step of 10 min at 70° C. before the digestion with AscI was performed. Additionally, the vector was dephosphorylated for 1 h at 37° C. using Antarctic phosphatase (New England Biolabs, Ipswich, Mass.). The ligation was performed for 2 h at room temperature using T4 DNA ligase (New England Biolabs, Ipswich, Mass.).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2798 (FIG. 25) contains the nat1 drug resistance marker flanked by a *P. ohmeri* ribulose reductase (poRR) promoter and an orotidine-5'-phosphate decarboxylase (poURA3) terminator.

The nat1 expression cassette was used to replace the *P. ohmeri* LEU2 selection marker in the integrative vector. In order to facilitate further cloning the nat1 cassette had to be flanked with XbaI (underlined in primer EV3643) and MluI (underlined in primer EV3644) sites by PCR with:

```
primer EV3643
                                        (SEQ ID No 31)
(CACTTCTAGACACTATCGATGGATCCGTAGAAATCTTG)

and primer EV3644
                                        (SEQ ID No 32)
(CACTACGCGTAAAGGTGAGGAAGTATATG).
```

Primer EV3643 contains an additional ClaI site (dotted line) following the XbaI site. pEVE2798 served as template (FIG. 25).

Amplification was performed in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was accomplished with an initial denaturation step of 30 sec at 98° C. followed by 30 cycles with 10 sec at 98° C./10 sec at 54° C./25 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.). The 1.3 kb nat1 expression cassette was restriction digested with MluI and XbaI enzymes (New England Biolabs, Ipswich, Mass.) and ligated for 2 h at room temperature to the 2.6 kb vector backbone of pEVE2787 (FIG. 23) linearized with MlI and XbaI enzymes (New England Biolabs, Ipswich, Mass.) and gel-purified with the Zymoclean™ Gel DNA Recovery Kit (Zymo Research Corporation, Irvine, Calif.) using T4 DNA ligase (New England Biolabs, Ipswich, Mass.) (FIG. 26).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2852 (FIG. 27) contains the nat1 selection marker under the control of the ribulose reductase (poRR) promoter and orotidine-5'-phosphate decarboxylase (poURA3) terminator and flanked by two loxP sites.

The integration plasmid does not contain any *P. ohmeri* homologous fragments needed for site specific integration into the genome, so far. This sites were attached in the next steps.

The 5' homologous region upstream of be LEU2 open reading frame was amplified from 50 ng poARS vector (FIG. 6) with:

```
primer EV3548
                                      (SEQ ID No 33)
(CACTCTGCAGGATCCAAGCTATCAACGAGA)

containing a PstI site (underlined)
and primer EV3549
                                      (SEQ ID No 34)
(CACTGCATGCGTTGCGGAAAAAACAGCC)

containing a SphI site (underlined).
```

The PCR was performed in a reaction mix consisting of 200 µM of each dNTP and 0.5 µM of each primer with 0.02 U/µl of iProof™ polymerase (BIO-RAD, Hercules, Calif.) in the appropriate 1× buffer. The amplification was accomplished with an initial denaturation step of 30 sec at 98° C. followed by 30 cycles with 10 sec at 98° C./10 sec at 61° C./15 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.). The 567 bp fragment was restriction digested with PstI and SphI enzymes (New England Biolabs, Ipswich, Mass.) and ligated for 2 h at room temperature to the 3.9 kb vector backbone of pEVE2852 (FIG. 27) linearized with PstI and SphI restriction enzymes (New England Biolabs, Ipswich, Mass.) and gel-purified with Zymoclean™ Gel DNA Recovery Kit (Zymo Research Corporation, Irvine, Calif.) using T4 DNA ligase (New England Biolabs, Ipswich, Mass.) (FIG. 29).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2855 (FIG. 28) contains a fragment homologous to the 5' region upstream of the LEU2 open reading frame and a nat1 marker flanked by two loxP sites.

The 3' homologous region downstream of be LEU2 open reading frame was amplified from 50 ng poARS vector (FIG. 6) with:

```
primer EV3550
                                      (SEQ ID No 35)
(CACT CCATGG AGTAGGTATATAAAAATATAAGAG)

containing a NcoI site (underlined)
and primer EV3551
                                      (SEQ ID No 36)
(CACTGCTAGCGTCGACAACAGCAACTAG)

containing a NheI site (underlined).
```

The PCR was performed in a reaction mix consisting of 200 µM of each dNTP and 0.5 µM of each primer with 0.02 U/µl of iProof™ polymerase (BIO-RAD, Hercules, Calif.) in the appropriate 1× buffer. The amplification was accomplished with an initial denaturation step of 30 sec at 98° C. followed by 30 cycles with 10 sec at 98° C./10 sec at 51° C./25 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.). The 1.3 kb fragment was restriction digested with NcoI and NheI enzymes (New England Biolabs, Ipswich, Mass.) and ligated for 2 h at room temperature to the 4.4 kb vector backbone of pEVE2855 (FIG. 28) linearized with NcoI and NheI restriction enzymes (New England Biolabs, Ipswich, Mass.) and gel-purified with Zymaclean™ Gel DNA Recovery Kit (Zymo Research Corporation, Irvine, Calif.) using T4 DNA ligase (New England Biolabs, Ipswich, Mass.) (FIG. 29).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting final LEU2 deletion plasmid pEVE2864 (FIG. 30) contains a fragment homologous to the 5' region upstream and a fragment homologous to the 3' region downstream of the LEU2 open reading frame and a nat1 marker flanked by two loxP sites.

Example 16 Generation of a Mutant *P. ohmeri* Strain Auxotrophic for Leucine

Since the generated *P. ohmeri* CNCM I-4605 strain did not display any auxotrophy so far, a LEU2 open reading frame deletion was performed, so as to be able to use the LEU2 selection marker for gene integrations.

For this purpose plasmid pEVE2864 (FIG. 30) was restriction digested with EcoRV and PstI enzymes (New England Biolabs, Ipswich, Mass.) for 2.5 h at 37° C. and the mixture used to transform the Mut165 strain according to the procedure described in Example 12.

To the regenerated cells, 7 ml of 50° C. warm top agar (1% yeast extract, 2% peptone, 2% glucose, 1 M sorbitol, pH 5.8 and 2.5% Noble agar) with 25 µg/ml natamycin was added and the mixture was poured evenly onto pre-warmed, sorbitol containing selection plates (1% yeast extract, 2% peptone, 2% glucose, 1 M sorbitol. pH 5.8 and 2% agar) with 25 µg/ml natamycin. Plates were incubated for 4 days at 30° C. Deletion of the LEU2 open reading frame was verified by no growth on selective plates without leucine and confirmed by colony PCR using:

```
primer EV3393
                                      (SEQ ID No 29)
(CAAGCATGCGGGAATGATAAGAGACTTTG)
and primer EV3795
                                      (SEQ ID No 37)
(CAAGTCGTGGAGATTCTGC)
```

The 1.6 kb fragment was amplified with an initial denaturation step of 30 sec at 98° C. followed by 30 cycles with 10 sec at 98° C./10 sec at 51° C./25 sec at 72° C., and a final extension step of 5 minutes at 72° C.

The resulting strain contains the full open reading frame deletion of the LEU2 gene in a CNCM I-4605 background and was deposited in France on Feb. 5, 2015, with the Collection Nationale de Cultures de Microorganismes [National Collection of Microorganism Cultures] of the Institut Pasteur (CNCM), 25 rue du Docteur Roux, 75724 PARIS codex 15, under number I-4955.

Example 17. Construction of a Double Expression Plasmids Comprising the NADPH-Specific Xylitol Dehydroctenase of *P. stipitis* and the NAD+-Specific D-Arabitol 4-Oxidoreductase of *E. coli*

In order to be able to express the NADPH-specific xylitol dehydrogenase of *P. stipitis* and the NAD specific D-arabitol 4-oxidoreductase of *E. coli* in the mutant *P. ohmeri* strain only auxotrophic for leucine, construction of a double expression plasmid was required.

The expression cassette containing the NADPH-specific xylitol dehydrogenase of *P. stipitis* was released from pEVE2562 (FIG. 12) by restriction cutting with SpeI and SacII enzymes (New England Biolabs, Ipswich, Mass.). The 1.9 kb fragment was gel-purified using Zymoclean™ Gel DNA Recovery Kit (Zymo Research Corporation, Irvine, Calif.) and blunted with the Blunting Enzyme Mix kit (New England Biolabs, Ipswich, Mass.) for 15 min at room temperature, followed by heat inactivation of the enzymes for 10 min at 70° C. The insert was then ligated for 2 h at room temperature to the 12.1 kb SpeI-linearized, blunted, dephosphorylated (1 h at 37° C. using Antarctic phosphatase—New England Biolabs, Ipswich, Mass.) and gel-purified pEVE3157 backbone (FIG. 21) containing the NAD+-specific D-arabitol 4-oxidoreductase of *E. coli* using T4 DNA ligase (New England Biolabs, Ipswich, Mass.) (FIG. 31).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3318 (FIG. 32) contains the double expression construct of the NADPH-specific xylitol dehydrogenase of *P. stipitis* flanked by a *P. ohmeri* ribulose reductase promoter and terminator (poRR) and the NAD$^+$-specific D-arabitol 4-oxidoreductase of *E. coli* under the control of the *P. ohmeri* phosphoglycerate kinase (poPGK1) promoter and ribulose reductase (poRR) terminator and the poLEU2 selection marker.

Example 18. Construction of Integrative Vectors for the Emission of the *E. coli* NAD$^+$-Specific D-arabitol 4-Oxidoreductase Gene and the *P. stipitis* NADPH-Specific Xylitol Dehydrogenase Gene in *P. ohmeri*

The NAD$^+$-specific D-arabitol 4-oxidoreductase gene of *E. coli* and the NADPH-specific xylitol dehydrogenase gene of *P. stipitis* should ultimately become an integral part of the *P. ohmeri* genome. Therefore, an integrative vector with a LEU2 selection marker had to be constructed, by replacing the nat1 selection marker of pEVE2852 and incorporating the double expression construct of arabitol oxidoreductase and xylitol dehydrogenase.

For this purpose, the *P. ohmeri* LEU2 open reading frame, flanked by an AscI and SphI sites, was generated by PCR with:

```
primer EV3645
                                      (SEQ ID No 38)
(CAAGGCGCGCCAAAATGTCTACCAAAACCATTAC)
and primer EV3646
                                      (SEQ ID No 39)
(GGAGCATGCCTACTTTCCCTCAGCCAAG).
```

Amplification was performed with 50 ng of poARS (FIG. 6) template in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was accomplished with an initial denaturation step of 30 sec at 98° C. followed by 30 cycles with 10 sec at 98° C./10 sec at 57° C./20 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.). The amplified LEU2 open reading frame was subsequently restriction digested with AscI and SphI enzymes (New England Biolabs, Ipswich, Mass.).

Additionally, a blunting of the SphI site with the Blunting Enzyme Mix kit (New England Biolabs, Ipswich, Mass.) for 15 min at room temperature, followed by heat inactivation of the enzymes for 10 min at 70° C. was performed in between the SphI and AscI digestion. The 1.1 kb gel-purified fragment was than ligated to the gel-purified 11 kb vector backbone of pEVE2811 cut with SphI and AscI restriction enzymes (New England Biolabs, Ipswich, Mass.). Also the SphI site of the vector was blunted for 15 min at room temperature with the Blunting Enzyme Mix kit (New England Biolabs, Ipswich, Mass.), followed by a heat inactivation step of 10 min at 70° C. before the digestion with AscI was performed. Additionally, the vector was dephosphorylated for 1 h at 37° C. using Antarctic phosphatase (New England Biolabs, Ipswich, Mass.). The ligation of the LEU2 open reading frame and the vector backbone was performed for 2 h at room temperature using T4 DNA ligase (New England Biolabs, Ipswich, Mass.).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2862 (FIG. 33) contains the *P. ohmeri* LEU2 marker flanked by a *P. ohmeri* ribulose reductase (poRR) promoter and an orotidine-5'-phosphate decarboxylase (poURA3) terminator.

Subsequently, the LEU2 marker was amplified by PCR using:

```
primer EV3643
                                      (SEQ ID No 31)
(CACTATCGATGGATCCGTAGAAATCTTG)

containing a ClaI site
```

-continued and primer EV3644

(SEQ ID No 32)
(CACTACGCGTAAAGGTGAGGAAGTATATG)

containing a MluI site (underline)
and pEVE2862 (FIG. 33) as template.

Amplification was performed in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was accomplished with an initial denaturation step of 30 sec at 98° C. followed by 30 cycles with 10 sec at 98° C./10 sec at 54° C./30 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.). The amplified 1.8 kb long LEU2 fragment was restriction digested with ClaI and MluI enzymes (New England Biolabs, Ipswich, Mass.) and ligated for 2 h at room temperature to the 2.6 kb ClaI and MluI (New England Biolabs, Ipswich, Mass.) restriction digested and gel-purified vector backbone of pEVE2852 (FIG. 27) using T4 DNA ligase (New England Biolabs, Ipswich, Mass.) (FIG. 34).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE2865 (FIG. 35) contains the P. ohmeri LEU2 marker flanked by two loxP sites.

For cloning of the integration vector, pEVE2865 was restriction digested with SalI enzyme (New England Biolabs, Ipswich, Mass.), blunted with the Blunting Enzyme Mix kit (New England Biolabs, Ipswich, Mass.) for 15 min at room temperature, followed by heat inactivation of the enzymes for 10 min at 70° C. and dephosphorylated dephosphorylated for 1 h at 37° C. using Antarctic phosphatase (New England Biolabs, Ipswich, Mass.).

The 4.5 kb gel-purified fragment of the vector backbone was used for ligation. As insert served a double expression construct of the NADPH-specific xylitol dehydrogenase genes of P. stipitis and the NAD⁺-specific D-arabitol 4-oxidoreductase of E. coli released from pEVE3318 (FIG. 32) by restriction cutting with NdeI and SacII enzymes (New England Biolabs, Ipswich, Mass.).

The 4.4 kb fragment was gel-purified using Zymoclean™ Gel DNA Recovery Kit (Zymo Research Corporation, Irvine, Calif.) and blunted with the Blunting Enzyme Mix kit (New England Biolabs, Ipswich, Mass.) for 15 min at room temperature, followed by heat inactivation of the enzymes for 10 min at 70° C., followed by an additional gel purification. The vector backbone of pEVE2865 and the insert of pEVE3318 were ligated for 2 h at room temperature using T4 DNA ligase (New England Biolabs, Ipswich, Mass.) (FIG. 34).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3387 (FIG. 36) contains the double expression construct of the NADPH-specific xylitol dehydrogenase gene of P. stipitis flanked by a P. ohmeri ribulose reductase promoter and terminator (poRR) and the NAD⁺-specific D-arabitol 4-oxidoreductase of E. coli under the control of the P. ohmeri phosphoglycerate kinase (poPGK1) promoter and transketolase (poTKL) terminator. As selection marker serves a P. ohmeri LEU2 gene flanked by two loxP sites.

Example 19. Construction of a First Generation Integrative P. ohmeri Strain Secreting Xylitol into the Media The previously described vector was used to randomly integrate the NAD⁺-specific D-arabitol 4-oxidoreductase gene of E. coli and the NADPH-specific xylitol dehydrogenase gene of P. stipitis into the genome of P. ohmeri.

For this purpose strain CNCM I-4955 (Example 16) auxotrophic for leucine was transformed with pEVE3387 (FIG. 36) restriction digested with NotI (New England Biolabs, Ipswich, Mass.) for 3 h at 37° C. according to the procedure described in Example 12. Transformants were selected on sorbitol plates without any leucine.

The resulting strain contains the NAD⁺-specific D-arabitol 4-oxidoreductase gene of E. coli and the NADPH-specific xylitol dehydrogenase gene of P. stipitis randomly integrated into the P. ohmeri genome and was deposited in France on May 20, 2015, with the Collection Nationale de Cultures de Microorganismes [National Collection of Microorganism Cultures] of the Institut Pasteur (CNCM), 25 rue du Docteur Roux, 75724 Cedex 15, under number I-4982.

Example 20. Construction of a Double/Triple Expression Plasmid Comprising the NADPH-Specific Xylitol Dehydrogenase of G. oxydans and the NAD⁺-Specific D-Arabitol 4-Oxidoreductase of E. coli In order to be able to express the NADPH-specific xylitol dehydrogenase of G. oxydans and the NAD⁺-specific D-arabitol 4-oxidoreductase of E. coli in the mutant P. ohmeri strain only auxotrophic for leucine, construction of a double expression plasmid was required.

The expression cassette containing the NADPH-specific xylitol dehydrogenase of G. oxydans was released from pEVE3284 (FIG. 10) by restriction cutting with SpeI and SacII enzymes (New England Biolabs, Ipswich, Mass.). The 1.6 kb fragment was gel-purified using Zymoclean™ Gel DNA Recovery Kit (Zymo Research Corporation, Irvine, Calif.) and blunted with the Blunting Enzyme Mix kit (New England Biolabs, Ipswich, Mass.) for 15 min at room temperature, followed by heat inactivation of the enzymes for 10 min at 70° C. The vector backbone used consisted of the 12.1 kb SpeI-linearized (New England Biolabs, Ipswich, Mass.) and gel-purified (Zymoclean™ Gel DNA Recovery Kit—Zymo Research Corporation, Irvine, Calif.) pEVE3157 backbone (FIG. 21) containing the NAD⁺-specific D-arabitol 4-oxidoreductase of E. coli.

The backbone has additionally been blunted for 15 min at room temperature with the Blunting Enzyme Mix kit (New England Biolabs, Ipswich, Mass.), followed by heat inactivation of the enzymes for 10 min at 70° C. and dephosphorylated for 1 h at 37° C. using Antarctic phosphatase (New England Biolabs, Ipswich, Mass.). Ligation was performed for 2 h at room temperature using T4 DNA ligase (New England Biolabs, Ipswich, Mass.) (FIG. 37).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmids pEVE3322 and pEVE3324 (FIG. 38) contain either the double expression construct of the NADPH-specific xylitol dehydrogenase of *G. oxydans* flanked by a *P. ohmeri* ribulose reductase promoter and terminator (poRR) and the NAD$^+$-specific D-arabitol 4-oxidoreductase of *E. coli* under the control of the *P. ohmeri* phosphoglycerate kinase (poPGK1) promoter and transketolase (poTKL) terminator or the triple expression construct of two NADPH-specific xylitol dehydrogenase genes of *G. oxydans* flanked by a *P. ohmeri* ribulose reductase promoter and terminator (poRR) and the NAD$^+$-specific D-arabitol 4-oxidoreductase of *E. coli* under the control of the *P. ohmeri* phosphoglycerate kinase (poPGK1) promoter and transketolase (poTKL) terminator and the poLEU2 selection marker.

Example 21. Construction of Integrative Vectors for, the Expression of the *E. coli* NAD$^+$-Specific D-Arabitol 4-Oxidoreductase Gene and the *G. oxydans* NADPH-Specific Xylitol Gene in *P. ohmeri*

Besides the integrative vector containing the NADPH-specific xylitol dehydrogenase of *P. stipitis* and the NAD$^+$-specific D-arabitol 4-oxidoreductase gene of *E. coli* also plasmids containing the NADPH-specific xylitol dehydrogenase of *G. oxydans* were generated.

For this purpose, the double and triple expression cassettes containing either one or two NADPH-specific xylitol dehydrogenase of *G. oxydans* and the NAD$^+$-specific D-arabitol 4-oxidoreductase of *E. coli* were released from pEVE3322 and pEVE3324 (FIG. 38) respectively, by restriction cutting with NdeI and SacII enzymes (New England Biolabs, Ipswich, Mass.).

The 4.1 kb and 5.7 kb fragments were gel-purified using Zymoclean™ Gel DNA Recovery Kit (Zymo Research Corporation, Irvine, Calif.) and blunted with the Blunting Enzyme Mix kit (New England Biolabs, Ipswich, Mass.) for 15 min at room temperature, followed by heat inactivation of the enzymes for 10 min at 70° C. As vector served the gel-purified (Zymoclean™ Gel DNA Recovery Kit—Zymo Research Corporation, Irvine, Calif.), 5.7 kb SalI-linearized pEVE2865 (FIG. 35).

The vector backbone has additionally been blunted for 15 min at room temperature with the Blunting Enzyme Mix kit (New England Biolabs, Ipswich, Mass.), followed by heat inactivation of the enzymes for 10 min at 70° C. and dephosphorylation for 1 h at 37° C. using Antarctic phosphatase (New England Biolabs, Ipswich, Mass.). Ligation of vector and insert was performed for 2 h at room temperature to using T4 DNA ligase (New England Biolabs, Ipswich, Mass.) (FIG. 39).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmids pEVE3390 and pEVE3392 (FIG. 40) contain the double or triple expression constructs of either one or two NADPH-specific xylitol dehydrogenase genes of *G. oxydans* flanked by a *P. ohmeri* ribulose reductase promoter and terminator (poRR) and the NAD$^+$-specific D-arabitol 4-oxidoreductase of *E. coli* under the control of the *P. ohmeri* phosphoglycerate kinase (poPGK1) promoter and transketolase (poTKL) terminator. As selection marker serves a *P. ohmeri* LEU2 gene flanked by two loxP sites.

Example 22. Construction of Second Generation Integrative Strains Capable of Secreting More than 100 g/L Xylitol First generation strain CNCM I-4982 containing a randomly integrated copy of the NAD$^+$-specific D-arabitol 4-oxidoreductase gene of *E. coli* and the NADPH-specific xylitol dehydrogenase gene of *P. stipitis* was used to further integrate additional copies of the two heterologous enzymes.

However, in order to be able to integrate above constructs the LEU2 selection marker had to be removed. For this purpose first generation strain CNCM I-4982 was transformed with vector pEVE3163 according to the procedure described in Example 12. The vector pEVE3163 contains the CRE recombinase of bacteriophage P1 (codon optimized according to Table 7) flanked by a *P. ohmeri* ribulose reductase promoter and terminator (poRR). Removal of the LEU2 selection marker was confirmed by no-growth of clones on plates without leucine.

The resulting strain EYS3842 was transformed with pEVE3390 or pEVE3392 (FIG. 40) restriction digested with NotI (New England Biolabs, Ipswich, Mass.) for 3 h at 37° C. according to the procedure described in Example 12. Transformants were selected on sorbitol plates without any leucine.

Resulting second generation strain EYS3929 contains two NAD$^+$-specific D-arabitol 4-oxidoreductase genes of *E. coli* and two NADPH-specific xylitol dehydrogenase genes, one from *G. oxydans* and a second one from *P. stipitis* randomly integrated into the genome. Strain EYS3930, on the other hand, contains an additional NADPH-specific xylitol dehydrogenase gene of *G. oxydans*.

Example 23. Construction of a Further Vector Used for the Integration of Additional Gene Copies of the NAD$^+$-Specific D-Arabitol 4-Oxidoreductase of *E. coli* and the NADPH-Specific Xylitol Dehydrogenase of *G. oxydans*

In order to construct a further integration vector, a double expression cassette of the NAD$^+$-specific D-arabitol 4-oxidoreductase of *E. coli* and the NADPH-specific xylitol dehydrogenase of *G. oxydans* was amplified by PCR using:

```
primer EV4904
                                (SEQ ID No 40)
(ATATCCCGGGCACCGTCATCACCGAAACGC)

containing a SmaI site
``` and primer EV4905

(SEQ ID No 41)
(ATAT<u>CCCGGG</u>CACGACCACGCTGATGAGC)

containing a SmaI site (underline)
and pEVE3321 as template

Amplification was performed in a reaction mix consisting of 200 µM of each dNTP and 0.5 µM of each primer with 0.02 U/µl of iProof™ polymerase (BIO-RAD, Hercules, Calif.) in the appropriate 1× buffer. The PCR was accomplished with an initial denaturation step of 30 sec at 98° C. followed by 30 cycles with 10 sec at 98° C./10 sec at 68° C. 175 sec at 72° C., and a final extension step of 5 minutes at 72° C. The PCR product was separated on a 1% agarose gel, extracted and purified using the Zymoclean™ Gel DNA Recovery Kit (Zymo Research Corporation, Irvine, Calif.).

The amplified 3.9 kb long fragment was restriction digested with SmaI (New England Biolabs, Ipswich, Mass.) and ligated for 2 h at room temperature to the 4.4 kb PvuII (New England Biolabs, Ipswich, Mass.) linearized, Antarctic phosphatase (New England Biolabs, Ipswich, Mass.) dephosphorylated and gel-purified vector backbone of pEVE2865 (FIG. 35) using T4 DNA ligase (New England Biolabs, Ipswich, Mass.) (FIG. 41).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmids pEVE4390 (FIG. 42) contains the double expression construct of the NAD$^+$-specific D-arabitol 4-oxidoreductase of E. coli under the control of the P. ohmeri phosphoglycerate kinase (poPGK1) promoter and transketolase (poTKL) terminator and the NADPH-specific xylitol dehydrogenase gene of G. oxydans flanked by a P. ohmeri ribulose reductase promoter and terminator (poRR). As selection marker serves a P. ohmeri LEU2 gene flanked by two loxP sites.

Example 24. Construction of a Vector Used for the Integration of the NADPH-Specific Xylitol Dehydrogenase of G. oxydans and the NAD$^+$-Specific D-Arabitol 4-Oxidoreductase of R. solanacearum An additional integrative vector for the expression of the NADPH-specific xylitol dehydrogenase of G. oxydans and of the NAD+-specific D-arabitol 4-oxidoreductase of R. solanacearum was constructed as follows: In a first step a double expression vector containing the two above genes was generated, This double expression cassette was the cloned into an integrative loxP vector.

A DNA fragment encoding the NAD+-specific D-arabitol 4-oxidoreductase gene of Ralstonia solanacearum was chemically synthesized by GeneArt® Gene Synthesis (Life Technologies, Regensburg, Germany) according to the submitted sequence of sequence SEQ ID No 42.

Nucleotides 2310548 to 2309151 of sequence AL646052.1 (obtained from the NCBI GenBank database) coding for the dalD gene were used as template and subjected to codon optimization for use in P. ohmeri ATCC 20209 according to Table 7 (above), using the Optimizer program. At the 5' and 3' ends of the resulting sequence, nucleotides encoding for the recognition sites of the restriction enzymes AscI (GGCGCGCC) and SphI (GCATGC) respectively, were manually added in the text file, in order to facilitate further cloning. Additionally, an adenosine triplet was included in front of the start ATG to account for an adenosine at the −3 position in the Kozak-like sequence of yeasts.

The final sequence (SEQ ID No 42) was then submitted for synthesis to GeneArt (Regensburg, Germany). The synthesized DNA fragment encoding the dalD gene was delivered as 5 µg lyophilized plasmid DNA in a pMA-RQ derived vector (13AB2EGP, FIG. 43).

The 1.4 kb fragment of the D-arabitol 4-oxidoreductase from R. solanacearum was released from vector 13AB2EGP (FIG. 43) by restriction digested with AscI and SphI (New England Biolabs, Ipswich, Mass.) and gel-purified with the Zymoclean™ Gel DNA Recovery Kit (Zymo Research Corporation, Irvine, Calif.). The insert was then ligated with the 11.8 kb backbone of pEVE2560 (FIG. 8) linearized with AscI and SphI (New England Biolabs, Ipswich, Mass.) and gel purified using T4 DNA ligase (New England Biolabs, Ipswich, Mass.) (FIG. 44).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE3898 (FIG. 45) contains the codon-optimised R. solanacearum NAD+-specific D-arabitol 4-oxidoreductase flanked by a ribulose reductase promoter and terminator of P. ohmeri and the poLEU2 selection marker.

In a next step the expression cassette containing the NADPH-specific xylitol dehydrogenase of G. oxydans flanked by a phosphoglycerate kinase promoter (poPGK) and ribulose reductase terminator (poRR) was released from pEVE3960 by restricon digest with SpeI and SacII (New England Biolabs, Ipswich, Mass.). The 1.8 kb fragment was gel-purified using Zymoclean™ Gel DNA Recovery Kit (Zymo Research Corporation, Irvine, Calif.) and blunted with the Blunting Enzyme Mix kit (New England Biolabs, Ipswich, Mass.) for 15 min at room temperature, followed by heat inactivation of the enzymes for 10 min at 70° C. As vector served the gel-purified (Zymoclean™ Gel DNA Recovery Kit—Zymo Research Corporation, Irvine, Calif.), 13.2 kb SalI-linearized pEVE3898. The vector backbone has additionally been blunted for 15 min at room temperature with the Blunting Enzyme Mix kit (New England Biolabs, Ipswich, Mass.), followed by heat inactivation of the enzymes for 10 min at 70° C. and dephosphorylation for 1 h at 37° C. using Antarctic phosphatase (New England Biolabs, Ipswich, Mass.). Ligation of vector and insert was performed for 2 h at room temperature to using T4 DNA ligase (New England Biolabs, Ipswich, Mass.) (FIG. 44).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE4077 (FIG. 46) contains the double expression construct of the NADPH-specific xylitol dehydrogenase of G. oxydans flanked by a P. ohmeri phosphoglycerate kinase promoter (poPGK) and a ribulose reductase terminator (poRR) and the NAD-specific D-arabitol 4-oxidoreductase of *R. solanacearum* under the control of the *P. ohmeri* ribulose reductase promoter and (poRR) terminator and the poLEU2 selection marker.

Finally, the double expression cassette of the NADPH-specific xylitol dehydrogenase of *G. oxydans* and the $NAD^+$-specific D-arabitol 4-oxidoreductase of *R. solanacearum* was released from pEVE4077 (FIG. 46) by restriction cutting with SapI (New England Biolabs, Ipswich, Mass.). The 5.9 kb fragment was gel-purified using Zymoclean™ Gel DNA Recovery Kit (Zymo Research Corporation, Irvine, Calif.) and blunted with the Blunting Enzyme Mix kit (New England Biolabs, Ipswich, Mass.) for 15 min at room temperature, followed by heat inactivation of the enzymes for 10 min at 70° C. As vector served the gel-purified (Zymoclean™ Gel DNA Recovery Kit—Zymo Research Corporation, Irvine, Calif.), 4.4 kb EcoRV-linearized pEVE2865 (FIG. 35), dephosphorylated for 1 h at 37° C. with Antarctic phosphatase (New England Biolabs, Ipswich, Mass.). Ligation of vector and insert was performed for 2 h at room temperature to using T4 DNA ligase (New England Biolabs, Ipswich, Mass.) (FIG. 44).

After transformation of XL10 Gold ultracompetent cells (Agilent Technologies, Santa Clara, Calif.) with the ligation mixture, plasmid DNA was isolated using the Zyppy™ Plasmid Miniprep Kit (Zymo Research Corporation, Irvine, Calif.) and further characterized by restriction digestion and sequencing (Microsynth, Balgach, Switzerland).

The resulting plasmid pEVE4377 (FIG. 47) contains the double expression construct of the NADPH-specific xylitol dehydrogenase of *G. oxydans* and the $NAD^+$-specific D-arabitol 4-oxidoreductase of *R. solanacearum* and the poLEU2 selection marker flanked by two loxP sites.

Example 25. Construction of Third Generation Integrative Strains with Increased Productivity of Xylitol The LEU2 marker of second generation strains EYS3929 and EYS3930 (Example 22) was loxed out as described in Example 18 using vector pEVE3163. The resulting strains EYS4118 and EYS4119 were transformed with pEVE4377 (FIG. 47) and pEVE4390 (FIG. 42), respectively, The vectors were restriction digested with NotI (New England Biolabs, Ipswich, Mass.) for 3 h at 37° C. according to the procedure described in Example 12. Transformants were selected on sorbitol plates without any leucine.

Resulting third generation strain EYS4353 contains three $NAD^+$-specific D-arabitol 4-oxidoreductase genes, two from *E. coli* and one from *R. solanacearum* and three NADPH-specific xylitol dehydrogenase genes, two from *G. oxydans* and one from *P. stipitis* randomly integrated into the genome.

The second third generation strain, on the other hand, contains three copies of the $NAD^+$-specific D-arabitol 4-oxidoreductase of *E. coli*, three copies of the NADPH-specific xylitol dehydrogenase of *G. oxydans* and one copy from *P. stipitis*, background and was deposited in France on Mar. 5, 2015, with the Collection Nationale de Cultures de Microorganismes [National Collection of Microorganism Cultures] of the Institut Pasteur (CNCM), 25 rue du Docteur Roux, 75724 PARIS Cedex 15, under number I-4960.

Example 26. Construction of Fourth Generation Integrative Strains

The LEU2 marker of third generation strains CNCM I-4960 (Example 25) was loxed out as described in Example 18 using vector pEVE3163. The resulting strain EYS4955 was transformed with pEVE4377 (FIG. 47) restriction digested with NotI (New England Biolabs, Ipswich, Mass.) for 3 h at 37° C. according to the procedure described in Example 12. Transformants were selected on sorbitol plates without any leucine.

Resulting fourth generation strain contains four $NAD^+$-specific D-arabitol 4-oxidoreductase genes, three from *E. coli* and one from *R. solanacearum* and four NADPH-specific xylitol dehydrogenase genes, three from *G. oxydans* and one from *P. stipitis* randomly integrated into the genomeand was deposited in France on May 20, 2015, with the Collection Nationale de Cultures de Microorganismes [National Collection of Microorganism Cultures] of the Institut Pasteur (CNCM), 25 rue du Docteur Roux, 75724 PARIS Cedex 15, under number I-4981.

Example 27. Polyol Production with *Pichia ohmeri* Strains (Synthetic Medium)

The yeast strains CNCM I-4605, CNCM I-4982. CNCM I-4960 & CNCM I-4981 constructed as described above, were fermented according to the following protocol.

The fermentation process is run under Nitrogen-limitation and can be separated into a growth phase and a production phase. During the growth phase the ammonia in the medium is completely consumed to produce biomass, once the biomass formation stops the production phase starts and Polyol levels increase. The platform used for the described fermentation process was a Multifors 2 from INFORS HT, using vessels with a working volume of 1 L. The fermenters were equipped with two Rushton six-blade disc turbines. Air was used for sparging the fermenters.

Temperature, pH, agitation, and aeration rate were controlled throughout the cultivation. The temperature was maintained at 36° C. The pH was kept at 3 by automatic addition of 5M KOH.

The aeration rate was kept at 1.0 vvm and the initial stirrer speed was set to 300 rpm. In order to prevent the Dissolved Oxygen (DO) to drop below 20% an automatic stirring cascade was employed. The operating conditions used in the fermentation process are summarized in Table 10.

TABLE 10

Operating conditions for the Polyol production fermentations

| Parameter | Set-point |
|---|---|
| Volume of liquid [L] | 1 |
| Temperature [° C.] | 36 |
| pH | 3 |
| Agitation speed [rpm] | Initially 300, then DO setpoint (20%) controlled stirrer cascade |
| Air flow rate [vvm] | 1 |

For inoculation of the fermenters a 1-stage propagation culture was used. The composition of the used propagation culture medium is described in table 11, Propagation cultures were prepared by inoculating 100 ml of medium in a 500-ml shake flask with 4 baffles (indent), The shake flasks were incubated on a shaking table at 30° C. and 150 rpm. The cells were grown for ~24 hrs into mid-exponential phase.

TABLE 11

Propagation culture medium composition.

| Raw material | | Concentration [g/L] |
|---|---|---|
| Glucose monohydrate | $C_6H_{12}O_6 * H_2O$ | 46 |
| Antifoam Erol 18 | | 1 drop |
| Potassium dihydrogenphosphate | $KH_2PO_4$ | 6 |
| Magnesium sulfate heptahydrate | $MgSO_4 * 7H_2O$ | 2.4 |
| Ammonium sulfate | $(NH_4)_2SO_4$ | 0.16 |
| Iron(II) ammonium sulfate hexahydrate | $Fe(SO_4)_2(NH_4)_2 * 6H_2O$ | 0.012 |
| Manganese (II) sulfate monohydrate | $MnSO_4 * H_2O$ | 0.0007 |
| Zinc sulfate heptahydrate | $ZnSO_4 * 7H_2O$ | 0.00007 |
| Biotine | $C_{10}H_{16}N_2O_3S$ | 0.0004 |
| Sodium phosphate | $Na_2HPO_4$ | 0.292 |
| Citric acid monohydrate | $C_6H_8O_7 * H_2O$ | 0.835 |

Prior to inoculation, an amount of the medium in the fermenter equivalent to the amount of inoculum was removed and an aliquot of the propagation culture was used for inoculation of the fermenter to a final volume of 1 L and an $OD_{600}$-at-start of ca. 0.2 (CDW ca. 0.03 g/L). The composition of the medium used in the fermenter is described in table 12.

TABLE 12

Fermentation medium composition.

| Raw material | | Concentration [g/L] |
|---|---|---|
| Glucose monohydrate | $C_6H_{12}O_6 * H_2O$ | 250 |
| Antifoam Erol 18 | | 0.67 |
| Potassium dihydrogenphosphate | $KH_2PO_4$ | 6 |
| Magnesium sulfate heptahydrate | $MgSO_4 * 7H_2O$ | 2.4 |
| Ammonium sulfate | $(NH_4)_2SO_4$ | 4 |
| Iron(II) ammonium sulfate hexahydrate | $Fe(SO_4)_2(NH_4)_2 * 6H_2O$ | 0.012 |
| Manganese (II) sulfate monohydrate | $MnSO_4 * H_2O$ | 0.0007 |
| Zinc sulfate heptahydrate | $ZnSO_4 * 7H_2O$ | 0.00007 |
| Biotine | $C_{10}H_{16}N_2O_3S$ | 0.0004 |

Samples were withdrawn in regular intervals and the total fermentation broth was analyzed for Glucose consumption and extracellular Polyol (Xylitol, Arabitol and Ribitol) formation. Furthermore common fermentation metabolites (Glycerol, Acetate, Ethanol, Pyruvate, Malate, Fumarate & Succinate) were determined. The increase in biomass was on one hand followed by $OD_{600}$ and on the other hand by cell dry weight (CDW) determination. The above mentioned measurements were used to determine Polyol production, Arabitol or Xylitol yield and productivity; the results are shown in table 13.

TABLE 13

Polyol production with *Pichia ohmeri* strains (synthetic medium).

| | CNC I-4605 | CNCM I-4982 | CNCM I-4960 | CNCM I-4981 |
|---|---|---|---|---|
| Elapsed Fermentation Time (EFT) [h] | 67 | 79 | 146 | 64 | 66 |
| Glucose [g/L] | 0 | 0 | 0 | 0 | 0 |
| Arabitol [g/L] | 118 | 74 | 0 | 0 | 0 |
| Ribitol [g/L] | 0 | 6 | 2 | 7 | 5 |
| Xylitol [g/L] | 0 | 28 | 60 | 110 | 120 |
| Yield Arabitol [%] | 52 | — | — | — | — |
| Yield Xylitol [%] | — | 12 | 26 | 44 | 48 |
| Productivity [g/L/h] | 1.76 | 0.35 | 0.41 | 1.71 | 1.81 |

*Pichia ohmeri* CNCM I-4605 produces arabitol only.

*Pichia ohmeri* CNCM I-4982 produces arabitol, xylitol and ribitol. In this strain one copy of NAD$^+$-D-arabitol 4-oxidoreductase gene and one copy of NADPH-specific xylitol dehydrogenase gene have been integrated. The modified strain is now able to consume arabitol. Consequently, after total consumption of glucose, arabitol and ribitol are re-consumed by CNCM I-4982 to produce more xylitol.

*Pichia ohmeri* CNCM I-4960 (third generation) and CNCM I-4981 (fourth generation) produce xylitol and ribitol but no more arabitol, The intracellular conversion of arabitol in xylulose and xylitol is efficient enough to avoid the excretion of arabitol into the broth. The more copies of the genes encoding for the NAD-specific D-arabitol oxidoreductase and the NADPH-specific xylitol dehydrogenase have been introduced into *P. ohmeri*, the higher are the titer, yield and productivity of xylitol.

The invention claimed is:

1. A method for producing xylitol, the method comprising:
   culturing in a culture medium a recombinant *Pichia ohmeri* capable of producing a xylitol titer of at least 15 g/L, in a supernatant within 48 h of culture, the recombinant *Pichia ohmeri* comprising:
   a heterologous nucleic acid sequence encoding a NAD+-specific D-arabitol 4-oxidoreductase (EC 1.1.1.11) from *Escherichia coli* and/or *Ralstonia solanacearum* comprising the amino acid sequence of SEQ ID NO: 2 and/or 43 using D-arabitol as a substrate and producing D-xylulose as a product; and
   a heterologous nucleic acid sequence encoding a NADPH-specific xylitol dehydrogenase from *Pichia stipitis* and/or *Gluconobacter oxydans* comprising the amino acid sequence of SEQ ID NO: 5 and/or 8 using D-xylulose as a substrate and producing xylitol as a product; and
   recovering the produced xylitol.

2. The method according to claim 1, wherein the culture medium provides the recombinant *Pichia ohmeri* with a carbon source.

3. The method according to claim 2, wherein the carbon source includes D-glucose.

4. The method according to claim 1, wherein the host cell recombinant *Pichia ohmeri* produces D-arabitol from D-glucose.

5. The method according to claim 1, wherein the recombinant *Pichia ohmeri* produces D-arabitol from D-glucose under a high osmotic pressure medium.

6. The method according to claim 1, wherein the recombinant *Pichia ohmeri* does not consume D-arabitol as a sole carbon source.

7. The method according to claim 1, wherein the sequence encoding the NAD+-specific D-arabitol 4-oxidoreductase (EC 1.1.1.11) comprises SEQ ID NO:3 or SEQ ID NO:42.

8. The method according to claim 1, wherein the sequence encoding the NADPH-specific xylitol dehydrogenase comprises SEQ ID NO:6 or SEQ ID NO:9.

9. The method according to claim 1, wherein the host cell recombinant *Pichia ohmeri* is a strain selected from strains 1-4982, 1-4960, and 1-4981 deposited at the National Collection of Microorganism Cultures.

10. The method according to claim 1, wherein the recombinant *Pichia ohmeri* comprises two, three, or four sequences encoding a NAD+-specific D-arabitol 4-oxidoreductase and/or two, three, or four sequences encoding the NADPH-specific xylitol dehydrogenase.

11. The method according to claim 1, further comprising purifying the recovered xylitol.

12. The method according to claim 11, wherein the xylitol is purified using chromatography.

* * * * *

SEQUENCE LISTING

```
<160> NUMBER OF SEQ ID NOS: 43

<210> SEQ ID NO 1
<211> LENGTH: 1385
<212> TYPE: DNA
<213> ORGANISM: Artificial sequence
<220> FEATURE:
<223> OTHER INFORMATION: Sequence encoding NAD-specific D-arabitol
      4-oxidoreductase flanked by restriction site
<220> FEATURE:
<221> NAME/KEY: misc_feature
<222> LOCATION: (1)..(8)
<223> OTHER INFORMATION: AscI recognition site
<220> FEATURE:
<221> NAME/KEY: CDS
<222> LOCATION: (12)..(1379)
<220> FEATURE:
<221> NAME/KEY: misc_feature
<222> LOCATION: (1380)..(1385)
<223> OTHER INFORMATION: SphI recognition site

<400> SEQUENCE: 1
ggcgcgccaa a atg aac gag cag ttc acc tgg ttg cac atc ggt ttg ggt       50
            Met Asn Glu Gln Phe Thr Trp Leu His Ile Gly Leu Gly
            1               5                   10 tct ttc cac aga gct cac cag gct tgg tac ttg cac aga ttg cag gtt        98
Ser Phe His Arg Ala His Gln Ala Trp Tyr Leu His Arg Leu Gln Val
    15                  20                  25 atg ggt gac aag aga tgg tct atc gct gct ggt aac atc aga aac gac       146
Met Gly Asp Lys Arg Trp Ser Ile Ala Ala Gly Asn Ile Arg Asn Asp
30                  35                  40                  45 gct gag cac gtt gtt cag gct ttg tct gct cag aag ggt aga tac gtt       194
Ala Glu His Val Val Gln Ala Leu Ser Ala Gln Lys Gly Arg Tyr Val
                50                  55                  60 ttg gag acc gtt tct cca gag ggt gtt tct gag tac gag gag atc acc       242
Leu Glu Thr Val Ser Pro Glu Gly Val Ser Glu Tyr Glu Glu Ile Thr
            65                  70                  75 tct atc cag aag ttg atc cca tgg cag gct gac ttg cag cca ttg atc       290
Ser Ile Gln Lys Leu Ile Pro Trp Gln Ala Asp Leu Gln Pro Leu Ile
        80                  85                  90 gct gag ggt gct gac cca aag acc aag gtt atc gct ttc acc gtt acc       338
Ala Glu Gly Ala Asp Pro Lys Thr Lys Val Ile Ala Phe Thr Val Thr
    95                  100                 105 gag ggt ggt tac tac ttg aac acc tct cac aag ttg gag gtt aac aac       386
Glu Gly Gly Tyr Tyr Leu Asn Thr Ser His Lys Leu Glu Val Asn Asn
110                 115                 120                 125 cca gac ttg gct gct gac ttg aag ggt ggt tgt aag acc atc tac ggt       434
Pro Asp Leu Ala Ala Asp Leu Lys Gly Gly Cys Lys Thr Ile Tyr Gly
                130                 135                 140 gtt atc acc aga atc ttg gag gct aga atg gct aac aac gct ggt cca       482
Val Ile Thr Arg Ile Leu Glu Ala Arg Met Ala Asn Asn Ala Gly Pro
            145                 150                 155 ttg acc ttg ttg aac tgt gac aac gtt aga cac aac ggt gag aga ttc       530
Leu Thr Leu Leu Asn Cys Asp Asn Val Arg His Asn Gly Glu Arg Phe
```

```
cac gac ggt ttg gtt gag ttc ttg cag ttg acc ggt aag cag gac gtt      578
His Asp Gly Leu Val Glu Phe Leu Gln Leu Thr Gly Lys Gln Asp Val
    175                 180                 185 atc gac tgg ttg tct acc aac acc acc tgt cca aac acc atg gtt gac      626
Ile Asp Trp Leu Ser Thr Asn Thr Thr Cys Pro Asn Thr Met Val Asp
190                 195                 200                 205 aga atc acc cca aga cca gct gct gag ttg cca gct aga atc aag gct      674
Arg Ile Thr Pro Arg Pro Ala Ala Glu Leu Pro Ala Arg Ile Lys Ala
                210                 215                 220 cag acc ggt atc gct gac aag gct cca gtt atg ggt gag acc ttc atc      722
Gln Thr Gly Ile Ala Asp Lys Ala Pro Val Met Gly Glu Thr Phe Ile
            225                 230                 235 cag tgg gtt gtt gag gac aac ttc aga gac gtt aga cca gct ttg gag      770
Gln Trp Val Val Glu Asp Asn Phe Arg Asp Val Arg Pro Ala Leu Glu
        240                 245                 250 aag gtt ggt gtt gag ttg gtt gct tct gtt atc cca tac gag gag gct      818
Lys Val Gly Val Glu Leu Val Ala Ser Val Ile Pro Tyr Glu Glu Ala
    255                 260                 265 aag atc aga atc ttg aac tct tct cac tct tgt atc gct tgg gct ggt      866
Lys Ile Arg Ile Leu Asn Ser Ser His Ser Cys Ile Ala Trp Ala Gly
270                 275                 280                 285 acc ttg atc ggt cag aag tac atc cac gag tct acc atg acc gac ttc      914
Thr Leu Ile Gly Gln Lys Tyr Ile His Glu Ser Thr Met Thr Asp Phe
                290                 295                 300 atc tac cag atc gct gac aga tac gtt acc gag gac gtt atc cca tgt      962
Ile Tyr Gln Ile Ala Asp Arg Tyr Val Thr Glu Asp Val Ile Pro Cys
            305                 310                 315 ttg ggt gac aac ggt atc gac ttg cca acc tac aga gac gtt gtt ttg     1010
Leu Gly Asp Asn Gly Ile Asp Leu Pro Thr Tyr Arg Asp Val Val Leu
        320                 325                 330 aag aga ttc acc aac cca cac atc cag gac acc aac cag aga gtt gct     1058
Lys Arg Phe Thr Asn Pro His Ile Gln Asp Thr Asn Gln Arg Val Ala
    335                 340                 345 gct gac ggt ttc tct aag atc cca gct atg atc gct cca acc ttg aga     1106
Ala Asp Gly Phe Ser Lys Ile Pro Ala Met Ile Ala Pro Thr Leu Arg
350                 355                 360                 365 gag tgt tac cag aga ggt gtt aga cca aac gct acc gct atg ttg cca     1154
Glu Cys Tyr Gln Arg Gly Val Arg Pro Asn Ala Thr Ala Met Leu Pro
                370                 375                 380 gct ttg ttc tac gtt ttc atg gag cag tgg cac cac ggt aag ttg cca     1202
Ala Leu Phe Tyr Val Phe Met Glu Gln Trp His His Gly Lys Leu Pro
            385                 390                 395 tac gag tac cag gac ggt atc ttg gac gct cca gct gtt cac gct atg     1250
Tyr Glu Tyr Gln Asp Gly Ile Leu Asp Ala Pro Ala Val His Ala Met
        400                 405                 410 ttg cag tct gct gac cca gtt gct gtt tac gct tct gac aag gct ttg     1298
Leu Gln Ser Ala Asp Pro Val Ala Val Tyr Ala Ser Asp Lys Ala Leu
    415                 420                 425 ttc ggt gac ttg acc gag aga gag gac ttc gct gct ttg ttg aga gag     1346
Phe Gly Asp Leu Thr Glu Arg Glu Asp Phe Ala Ala Leu Leu Arg Glu
430                 435                 440                 445 aag atc gct gac gtt tac gct ttg atc aac taa gcatgc                   1385
Lys Ile Ala Asp Val Tyr Ala Leu Ile Asn
                450                 455

<210> SEQ ID NO 2
<211> LENGTH: 455
<212> TYPE: PRT
<213> ORGANISM: Artificial sequence
```

<220> FEATURE:
<223> OTHER INFORMATION: Synthetic Construct

<400> SEQUENCE: 2

```
Met Asn Glu Gln Phe Thr Trp Leu His Ile Gly Leu Gly Ser Phe His
1               5                   10                  15

Arg Ala His Gln Ala Trp Tyr Leu His Arg Leu Gln Val Met Gly Asp
            20                  25                  30

Lys Arg Trp Ser Ile Ala Ala Gly Asn Ile Arg Asn Asp Ala Glu His
        35                  40                  45

Val Val Gln Ala Leu Ser Ala Gln Lys Gly Arg Tyr Val Leu Glu Thr
    50                  55                  60

Val Ser Pro Glu Gly Val Ser Glu Tyr Glu Ile Thr Ser Ile Gln
65                  70                  75                  80

Lys Leu Ile Pro Trp Gln Ala Asp Leu Gln Pro Leu Ile Ala Glu Gly
                85                  90                  95

Ala Asp Pro Lys Thr Lys Val Ile Ala Phe Thr Val Thr Glu Gly Gly
            100                 105                 110

Tyr Tyr Leu Asn Thr Ser His Lys Leu Glu Val Asn Asn Pro Asp Leu
        115                 120                 125

Ala Ala Asp Leu Lys Gly Gly Cys Lys Thr Ile Tyr Gly Val Ile Thr
    130                 135                 140

Arg Ile Leu Glu Ala Arg Met Ala Asn Asn Ala Gly Pro Leu Thr Leu
145                 150                 155                 160

Leu Asn Cys Asp Asn Val Arg His Asn Gly Glu Arg Phe His Asp Gly
                165                 170                 175

Leu Val Glu Phe Leu Gln Leu Thr Gly Lys Gln Asp Val Ile Asp Trp
            180                 185                 190

Leu Ser Thr Asn Thr Thr Cys Pro Asn Thr Met Val Asp Arg Ile Thr
        195                 200                 205

Pro Arg Pro Ala Ala Glu Leu Pro Ala Arg Ile Lys Ala Gln Thr Gly
    210                 215                 220

Ile Ala Asp Lys Ala Pro Val Met Gly Glu Thr Phe Ile Gln Trp Val
225                 230                 235                 240

Val Glu Asp Asn Phe Arg Asp Val Arg Pro Ala Leu Glu Lys Val Gly
                245                 250                 255

Val Glu Leu Val Ala Ser Val Ile Pro Tyr Glu Glu Ala Lys Ile Arg
            260                 265                 270

Ile Leu Asn Ser Ser His Ser Cys Ile Ala Trp Ala Gly Thr Leu Ile
        275                 280                 285

Gly Gln Lys Tyr Ile His Glu Ser Thr Met Thr Asp Phe Ile Tyr Gln
    290                 295                 300

Ile Ala Asp Arg Tyr Val Thr Glu Asp Val Ile Pro Cys Leu Gly Asp
305                 310                 315                 320

Asn Gly Ile Asp Leu Pro Thr Tyr Arg Asp Val Val Leu Lys Arg Phe
                325                 330                 335

Thr Asn Pro His Ile Gln Asp Thr Asn Gln Arg Val Ala Ala Asp Gly
            340                 345                 350

Phe Ser Lys Ile Pro Ala Met Ile Ala Pro Thr Leu Arg Glu Cys Tyr
        355                 360                 365

Gln Arg Gly Val Arg Pro Asn Ala Thr Ala Met Leu Pro Ala Leu Phe
    370                 375                 380

Tyr Val Phe Met Glu Gln Trp His His Gly Lys Leu Pro Tyr Glu Tyr
385                 390                 395                 400
```

Gln Asp Gly Ile Leu Asp Ala Pro Ala Val His Ala Met Leu Gln Ser
            405                 410                 415

Ala Asp Pro Val Ala Val Tyr Ala Ser Asp Lys Ala Leu Phe Gly Asp
            420                 425                 430

Leu Thr Glu Arg Glu Asp Phe Ala Ala Leu Leu Arg Glu Lys Ile Ala
            435                 440                 445

Asp Val Tyr Ala Leu Ile Asn
    450                 455

<210> SEQ ID NO 3
<211> LENGTH: 1368
<212> TYPE: DNA
<213> ORGANISM: artificial sequence
<220> FEATURE:
<223> OTHER INFORMATION: NAD+ specific D-arabitol 4-oxidoreductase
      encoding sequence

<400> SEQUENCE: 3
atgaacgagc agttcacctg gttgcacatc ggtttgggtt ctttccacag agctcaccag      60
gcttggtact tgcacagatt gcaggttatg ggtgacaaga gatggtctat cgctgctggt     120
aacatcagaa cgacgctga gcacgttgtt caggcttttgt ctgctcagaa gggtagatac     180
gttttggaga ccgtttctcc agagggtgtt tctgagtacg aggagatcac ctctatccag     240
aagttgatcc catggcaggc tgacttgcag ccattgatcg ctgagggtgc tgacccaaag     300
accaaggtta tcgctttcac cgttaccgag ggtggttact acttgaacac ctctcacaag     360
ttggaggtta caacccaga cttggctgct gacttgaagg gtggttgtaa gaccatctac     420
ggtgttatca ccagaatctt ggaggctaga atggctaaca acgctggtcc attgaccttg     480
ttgaactgtg acaacgttag acacaacggt gagagattcc acgacggttt ggttgagttc     540
ttgcagttga ccggtaagca ggacgttatc gactggttgt ctaccaacac cacctgtcca     600
aacaccatgt tgacagaat cacccccaaga ccagctgctg agttgccagc tagaatcaag     660
gctcagaccg gtatcgctga caaggctcca gttatgggtg agaccttcat ccagtgggtt     720
gttgaggaca cttcagaga cgttagacca gcttttggaga aggttggtgt tgagttggtt     780
gcttctgtta tcccatacga ggaggctaag atcagaatct tgaactcttc tcactcttgt     840
atcgcttggg ctggtacctt gatcggtcag aagtacatcc acgagtctac catgaccgac     900
ttcatctacc agatcgctga cagatacgtt accgaggacg ttatcccatg tttgggtgac     960
aacggtatcg acttgccaac ctacagagac gttgttttga agagattcac caacccacac    1020
atccaggaca ccaaccagag agttgctgct gacggtttct ctaagatccc agctatgatc    1080
gctccaacct tgagagagtg ttaccagaga ggtgttagac aaacgctac cgctatgttg    1140 ccagctttgt tctacgtttt catggagcag tggcaccacg taagttgcc atacgagtac    1200 caggacggta tcttggacgc tccagctgtt cacgctatgt tgcagtctgc tgacccagtt    1260
gctgtttacg cttctgacaa ggctttgttc ggtgacttga ccgagagaga ggacttcgct    1320
gctttgttga gagagaagat cgctgacgtt tacgctttga tcaactaa                  1368

<210> SEQ ID NO 4
<211> LENGTH: 1107
<212> TYPE: DNA
<213> ORGANISM: artificial sequence
<220> FEATURE:
<223> OTHER INFORMATION: Sequence encoding NADPH-specific xylitol
      dehydrogenase flanked by restriction sites
<220> FEATURE:

```
<221> NAME/KEY: misc_feature
<222> LOCATION: (1)..(6)
<223> OTHER INFORMATION: HindIII recognition site
<220> FEATURE:
<221> NAME/KEY: CDS
<222> LOCATION: (10)..(1101)
<220> FEATURE:
<221> NAME/KEY: misc_feature
<222> LOCATION: (1102)..(1107)
<223> OTHER INFORMATION: SacII recognition site

<400> SEQUENCE: 4 aagcttaaa atg act gct aac cct tcc ttg gtg ttg aac aag atc gac gac        51
          Met Thr Ala Asn Pro Ser Leu Val Leu Asn Lys Ile Asp Asp
          1               5                   10 att tcg ttc gaa act tac gat gcc cca gaa atc tct gaa cct acc gat         99
Ile Ser Phe Glu Thr Tyr Asp Ala Pro Glu Ile Ser Glu Pro Thr Asp
15          20                  25                  30 gtc ctc gtc cag gtc aag aaa acc ggt atc tgt ggt tcc gac atc cac        147
Val Leu Val Gln Val Lys Lys Thr Gly Ile Cys Gly Ser Asp Ile His
            35                  40                  45 ttc tac gcc cat ggt aga atc ggt aac ttc gtt ttg acc aag cca atg        195
Phe Tyr Ala His Gly Arg Ile Gly Asn Phe Val Leu Thr Lys Pro Met
        50                  55                  60 gtc ttg ggt cac gaa tcc gcc ggt act gtt gtc cag gtt ggt aag ggt        243
Val Leu Gly His Glu Ser Ala Gly Thr Val Val Gln Val Gly Lys Gly
    65                  70                  75 gtc acc tct ctt aag gtt ggt gac aac gtc gct atc gaa cca ggt att        291
Val Thr Ser Leu Lys Val Gly Asp Asn Val Ala Ile Glu Pro Gly Ile
80                  85                  90 cca tcc aga ttc tcc gac gaa tac aag agc ggt cac tac aac ttg tgt        339
Pro Ser Arg Phe Ser Asp Glu Tyr Lys Ser Gly His Tyr Asn Leu Cys
95                  100                 105                 110 cct cac atg gcc ttc gcc gct act cct aac tcc aag gaa ggc gaa cca        387
Pro His Met Ala Phe Ala Ala Thr Pro Asn Ser Lys Glu Gly Glu Pro
            115                 120                 125 aac cca cca ggt acc tta tgt aag tac ttc aag tcg cca gaa gac ttc        435
Asn Pro Pro Gly Thr Leu Cys Lys Tyr Phe Lys Ser Pro Glu Asp Phe
        130                 135                 140 ttg gtc aag ttg cca gac cac gtc agc ttg gaa ctc ggt gct ctt gtt        483
Leu Val Lys Leu Pro Asp His Val Ser Leu Glu Leu Gly Ala Leu Val
    145                 150                 155 gag cca ttg tct gtt ggt gtc cac gcc tcc aag ttg ggt tcc gtt gct        531
Glu Pro Leu Ser Val Gly Val His Ala Ser Lys Leu Gly Ser Val Ala
160                 165                 170 ttc ggc gac tac gtt gcc gtc ttt ggt gct ggt cct gtt ggt ctt ttg        579
Phe Gly Asp Tyr Val Ala Val Phe Gly Ala Gly Pro Val Gly Leu Leu
175                 180                 185                 190 gct gct gct gtc gcc aag acc ttc ggt gct aag ggt gtc atc gtc gtt        627
Ala Ala Ala Val Ala Lys Thr Phe Gly Ala Lys Gly Val Ile Val Val
            195                 200                 205 gct aga tca gac aga aag ttg aag atg gcc aag gac att ggt gct gct        675
Ala Arg Ser Asp Arg Lys Leu Lys Met Ala Lys Asp Ile Gly Ala Ala
        210                 215                 220 act cac acc ttc aac tcc aag acc ggt ggt tct gaa gaa ttg atc aag        723
Thr His Thr Phe Asn Ser Lys Thr Gly Gly Ser Glu Glu Leu Ile Lys
    225                 230                 235 gct ttc ggt ggt aac gtg cca aac gtc gtt ttg gaa tgt act ggt gct        771
Ala Phe Gly Gly Asn Val Pro Asn Val Val Leu Glu Cys Thr Gly Ala
240                 245                 250 gaa cct tgt atc aag ttg ggt gtt gac gcc att gcc cca ggt ggt cgt        819
Glu Pro Cys Ile Lys Leu Gly Val Asp Ala Ile Ala Pro Gly Gly Arg
```

```
                255                 260                 265                 270
ttc gtt caa gtt ggt aac gct gct ggt cca gtc agc ttc cca atc acc        867
Phe Val Gln Val Gly Asn Ala Ala Gly Pro Val Ser Phe Pro Ile Thr
                    275                 280                 285 gtt ttc gcc atg aag gaa ttg act ttg ttc ggt tct ttc aga tac gga        915
Val Phe Ala Met Lys Glu Leu Thr Leu Phe Gly Ser Phe Arg Tyr Gly
                    290                 295                 300 ttc aac gac tac aag act gct gtt gga atc ttt gac act aac tac caa        963
Phe Asn Asp Tyr Lys Thr Ala Val Gly Ile Phe Asp Thr Asn Tyr Gln
                    305                 310                 315 aac ggt aga gaa aat gct cca att gac ttt gaa caa ttg atc acc cac       1011
Asn Gly Arg Glu Asn Ala Pro Ile Asp Phe Glu Gln Leu Ile Thr His
                    320                 325                 330 aga tac aag ttc aag gac gct att gaa gcc tac gac ttg gtc aga gcc      1059
Arg Tyr Lys Phe Lys Asp Ala Ile Glu Ala Tyr Asp Leu Val Arg Ala
335                 340                 345                 350 ggt aag ggt gct gtc aag tgt ctc att gac ggc cct gag taa ccgcgg        1107
Gly Lys Gly Ala Val Lys Cys Leu Ile Asp Gly Pro Glu
                    355                 360
```

<210> SEQ ID NO 5
<211> LENGTH: 363
<212> TYPE: PRT
<213> ORGANISM: artificial sequence
<220> FEATURE:
<223> OTHER INFORMATION: Synthetic Construct

<400> SEQUENCE: 5

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
                20                  25                  30

Val Gln Val Lys Lys Thr Gly Ile Cys Gly Ser Asp Ile His Phe Tyr
            35                  40                  45

Ala His Gly Arg Ile Gly Asn Phe Val Leu Thr Lys Pro Met Val Leu
        50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
                100                 105                 110

Met Ala Phe Ala Ala Thr Pro Asn Ser Lys Glu Gly Glu Pro Asn Pro
            115                 120                 125

Pro Gly Thr Leu Cys Lys Tyr Phe Lys Ser Pro Glu Asp Phe Leu Val
        130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
                180                 185                 190

Ala Val Ala Lys Thr Phe Gly Ala Lys Gly Val Ile Val Ala Arg
            195                 200                 205

Ser Asp Arg Lys Leu Lys Met Ala Lys Asp Ile Gly Ala Ala Thr His
210                 215                 220

Thr Phe Asn Ser Lys Thr Gly Gly Ser Glu Glu Leu Ile Lys Ala Phe
```

```
                225                 230                 235                 240
Gly Gly Asn Val Pro Asn Val Val Leu Glu Cys Thr Gly Ala Glu Pro
                    245                 250                 255

Cys Ile Lys Leu Gly Val Asp Ala Ile Ala Pro Gly Gly Arg Phe Val
                260                 265                 270

Gln Val Gly Asn Ala Ala Gly Pro Val Ser Phe Pro Ile Thr Val Phe
            275                 280                 285

Ala Met Lys Glu Leu Thr Leu Phe Gly Ser Phe Arg Tyr Gly Phe Asn
        290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360

<210> SEQ ID NO 6
<211> LENGTH: 1092
<212> TYPE: DNA
<213> ORGANISM: artificial sequence
<220> FEATURE:
<223> OTHER INFORMATION: sequence encoding NADPH specific xylitol
      dehydrogenase

<400> SEQUENCE: 6
atgactgcta acccttcctt ggtgttgaac aagatcgacg acatttcgtt cgaaacttac      60
gatgccccag aaatctctga acctaccgat gtcctcgtcc aggtcaagaa aaccggtatc     120
tgtggttccg acatccactt ctacgcccat ggtagaatcg gtaacttcgt tttgaccaag     180
ccaatggtct tgggtcacga atccgccggt actgttgtcc aggttggtaa gggtgtcacc     240
tctcttaagg ttggtgacaa cgtcgctatc gaaccaggta ttccatccag attctccgac     300
gaatacaaga gcggtcacta caacttgtgt cctcacatgg ccttcgccgc tactcctaac     360
tccaaggaag gcgaaccaaa cccaccaggt accttatgta agtacttcaa gtcgccagaa     420
gacttcttgg tcaagttgcc agaccacgtc agcttggaac tcggtgctct tgttgagcca     480
ttgtctgttg gtgtccacgc ctccaagttg ggttccgttg ctttcggcga ctacgttgcc     540
gtctttggtg ctggtcctgt tggtctttttg ctgctgctg tcgccaagac cttcggtgct     600
aagggtgtca tcgtcgttgc tagatcagac agaaagttga gatggccaa ggacattggt     660 gctgctactc acaccttcaa ctccaagacc ggtggttctg aagaattgat caaggctttc     720
ggtggtaacg tgccaaacgt cgttttggaa tgtactggtg ctgaaccttg tatcaagttg     780
ggtgttgacg ccattgcccc aggtggtcgt ttcgttcaag ttggtaacgc tgctggtcca     840
gtcagcttcc caatcaccgt tttcgccatg aaggaattga ctttgttcgg ttctttcaga     900
tacggattca acgactacaa gactgctgtt ggaatctttg acactaacta ccaaaacggt     960
agagaaaatg ctccaattga ctttgaacaa ttgatcaccc acagatacaa gttcaaggac    1020
gctattgaag cctacgactt ggtcagagcc ggtaagggtg ctgtcaagtg tctcattgac    1080
ggccctgagt aa                                                        1092

<210> SEQ ID NO 7
<211> LENGTH: 806
<212> TYPE: DNA
```

```
<213> ORGANISM: artificial sequence
<220> FEATURE:
<223> OTHER INFORMATION: sequence encoding NADPH-specific xylitol
      dehydrogenase flanked by restriction sites
<220> FEATURE:
<221> NAME/KEY: misc_feature
<222> LOCATION: (1)..(8)
<223> OTHER INFORMATION: AscI recognition site
<220> FEATURE:
<221> NAME/KEY: CDS
<222> LOCATION: (12)..(800)
<220> FEATURE:
<221> NAME/KEY: misc_feature
<222> LOCATION: (801)..(806)
<223> OTHER INFORMATION: SphI recognition site

<400> SEQUENCE: 7
```

| | | |
|---|---|---|
| ggcgcgccaa a atg tct aag aag ttc aac ggt aag gtt tgt ttg gtt acc<br>            Met Ser Lys Lys Phe Asn Gly Lys Val Cys Leu Val Thr<br>             1              5                    10 | 50 |
| ggt gct ggt ggt aac atc ggt ttg gct acc gct ttg aga ttg gct gag<br>Gly Ala Gly Gly Asn Ile Gly Leu Ala Thr Ala Leu Arg Leu Ala Glu<br>    15                  20                  25 | 98 |
| gag ggt acc gct atc gct ttg ttg tct aga aac aga gag gct ttg gag<br>Glu Gly Thr Ala Ile Ala Leu Leu Ser Arg Asn Arg Glu Ala Leu Glu<br>30                  35                  40                  45 | 146 |
| aag gct gag gct tct gtt aga gag aag ggt gtt gag gct aga tct tac<br>Lys Ala Glu Ala Ser Val Arg Glu Lys Gly Val Glu Ala Arg Ser Tyr<br>                  50                  55                  60 | 194 |
| gtt tgt gac gtt acc tct gag gag gct gtt atc ggt acc gtt gac tct<br>Val Cys Asp Val Thr Ser Glu Glu Ala Val Ile Gly Thr Val Asp Ser<br>            65                  70                  75 | 242 |
| gtt gtt aga gac ttc ggt aag atc gac ttc ttg ttc aac aac gct ggt<br>Val Val Arg Asp Phe Gly Lys Ile Asp Phe Leu Phe Asn Asn Ala Gly<br>    80                  85                  90 | 290 |
| tac cag ggt gct ttc gct cca gtt cag gac tac cca tct gac gac ttc<br>Tyr Gln Gly Ala Phe Ala Pro Val Gln Asp Tyr Pro Ser Asp Asp Phe<br>        95                  100                 105 | 338 |
| gct aga gtt ttg acc atc aac gtt acc ggt gct ttc cac gtt ttg aag<br>Ala Arg Val Leu Thr Ile Asn Val Thr Gly Ala Phe His Val Leu Lys<br>110                  115                 120               125 | 386 |
| gct gtt tct aga cag atg atc acc cag aac tac ggt aga atc gtt aac<br>Ala Val Ser Arg Gln Met Ile Thr Gln Asn Tyr Gly Arg Ile Val Asn<br>               130                 135               140 | 434 |
| acc gct tct atg gct ggt gtt aag ggt cca cca aac atg gct gct tac<br>Thr Ala Ser Met Ala Gly Val Lys Gly Pro Pro Asn Met Ala Ala Tyr<br>                  145                 150               155 | 482 |
| ggt acc tct aag ggt gct atc atc gct ttg acc gag acc gct gct ttg<br>Gly Thr Ser Lys Gly Ala Ile Ile Ala Leu Thr Glu Thr Ala Ala Leu<br>              160                 165               170 | 530 |
| gac ttg gct cca tac aac atc aga gtt aac gct atc tct cca ggt tac<br>Asp Leu Ala Pro Tyr Asn Ile Arg Val Asn Ala Ile Ser Pro Gly Tyr<br>175                  180                 185 | 578 |
| atg ggt cca ggt ttc atg tgg gag aga cag gtt gag ttg cag gct aag<br>Met Gly Pro Gly Phe Met Trp Glu Arg Gln Val Glu Leu Gln Ala Lys<br>190                  195                 200               205 | 626 |
| gtt ggt tct cag tac ttc tct acc gac cca aag gtt gtt gct cag cag<br>Val Gly Ser Gln Tyr Phe Ser Thr Asp Pro Lys Val Val Ala Gln Gln<br>                  210                 215               220 | 674 |
| atg atc ggt tct gtt cca atg aga aga tac ggt gac atc aac gag atc<br>Met Ile Gly Ser Val Pro Met Arg Arg Tyr Gly Asp Ile Asn Glu Ile<br>              225                 230               235 | 722 |
| cca ggt gtt gtt gct ttc ttg ttg ggt gac gac tct tct ttc atg acc | 770 |

```
                Pro Gly Val Val Ala Phe Leu Leu Gly Asp Asp Ser Ser Phe Met Thr
                            240                 245                 250 ggt gtt aac ttg cca atc gct ggt ggt tga gcatgc                              806
Gly Val Asn Leu Pro Ile Ala Gly Gly
        255                 260
```

<210> SEQ ID NO 8
<211> LENGTH: 262
<212> TYPE: PRT
<213> ORGANISM: artificial sequence
<220> FEATURE:
<223> OTHER INFORMATION: Synthetic Construct

<400> SEQUENCE: 8

```
Met Ser Lys Lys Phe Asn Gly Lys Val Cys Leu Val Thr Gly Ala Gly
1               5                   10                  15

Gly Asn Ile Gly Leu Ala Thr Ala Leu Arg Leu Ala Glu Glu Gly Thr
            20                  25                  30

Ala Ile Ala Leu Leu Ser Arg Asn Arg Glu Ala Leu Glu Lys Ala Glu
        35                  40                  45

Ala Ser Val Arg Glu Lys Gly Val Glu Ala Arg Ser Tyr Val Cys Asp
    50                  55                  60

Val Thr Ser Glu Glu Ala Val Ile Gly Thr Val Asp Ser Val Val Arg
65                  70                  75                  80

Asp Phe Gly Lys Ile Asp Phe Leu Phe Asn Asn Ala Gly Tyr Gln Gly
                85                  90                  95

Ala Phe Ala Pro Val Gln Asp Tyr Pro Ser Asp Phe Ala Arg Val
            100                 105                 110

Leu Thr Ile Asn Val Thr Gly Ala Phe His Val Leu Lys Ala Val Ser
        115                 120                 125

Arg Gln Met Ile Thr Gln Asn Tyr Gly Arg Ile Val Asn Thr Ala Ser
    130                 135                 140

Met Ala Gly Val Lys Gly Pro Pro Asn Met Ala Ala Tyr Gly Thr Ser
145                 150                 155                 160

Lys Gly Ala Ile Ile Ala Leu Thr Glu Thr Ala Ala Leu Asp Leu Ala
                165                 170                 175

Pro Tyr Asn Ile Arg Val Asn Ala Ile Ser Pro Gly Tyr Met Gly Pro
            180                 185                 190

Gly Phe Met Trp Glu Arg Gln Val Glu Leu Gln Ala Lys Val Gly Ser
        195                 200                 205

Gln Tyr Phe Ser Thr Asp Pro Lys Val Val Ala Gln Gln Met Ile Gly
    210                 215                 220

Ser Val Pro Met Arg Arg Tyr Gly Asp Ile Asn Glu Ile Pro Gly Val
225                 230                 235                 240

Val Ala Phe Leu Leu Gly Asp Asp Ser Ser Phe Met Thr Gly Val Asn
                245                 250                 255

Leu Pro Ile Ala Gly Gly
            260
```

<210> SEQ ID NO 9
<211> LENGTH: 789
<212> TYPE: DNA
<213> ORGANISM: artificial sequence
<220> FEATURE:
<223> OTHER INFORMATION: sequence encoding NADPH specific xylitol
      dehydrogenase

<400> SEQUENCE: 9

-continued

| | |
|---|---|
| atgtctaaga agttcaacgg taaggtttgt ttggttaccg gtgctggtgg taacatcggt | 60 |
| ttggctaccg ctttgagatt ggctgaggag ggtaccgcta tcgctttgtt gtctagaaac | 120 |
| agagaggctt tggagaaggc tgaggcttct gttagagaga agggtgttga ggctagatct | 180 |
| tacgtttgtg acgttacctc tgaggaggct gttatcggta ccgttgactc tgttgttaga | 240 |
| gacttcggta agatcgactt cttgttcaac aacgctggtt accagggtgc tttcgctcca | 300 |
| gttcaggact acccatctga cgacttcgct agagttttga ccatcaacgt taccggtgct | 360 |
| ttccacgttt tgaaggctgt ttctagacag atgatcaccc agaactacgg tagaatcgtt | 420 |
| aacaccgctt ctatggctgg tgttaagggt ccaccaaaca tggctgctta cggtacctct | 480 |
| aagggtgcta tcatcgcttt gaccgagacc gctgctttgg acttggctcc atacaacatc | 540 |
| agagttaacg ctatctctcc aggttacatg ggtccaggtt tcatgtggga gagacaggtt | 600 |
| gagttgcagg ctaaggttgg ttctcagtac ttctctaccg acccaaaggt tgttgctcag | 660 |
| cagatgatcg ttctgttcc aatgagaaga tacggtgaca tcaacgagat cccaggtgtt | 720 |
| gttgctttct gttgggtga cgactcttct ttcatgaccg tgttaactt gccaatcgct | 780 |
| ggtggttga | 789 |

```
<210> SEQ ID NO 10
<211> LENGTH: 873
<212> TYPE: DNA
<213> ORGANISM: artificial sequence
<220> FEATURE:
<223> OTHER INFORMATION: sequence encoding tagatose-3-epimerase
<220> FEATURE:
<221> NAME/KEY: CDS
<222> LOCATION: (1)..(873)

<400> SEQUENCE: 10
```

| | | |
|---|---|---|
| atg aac aaa gtt ggc atg ttc tac acc tac tgg tcg act gag tgg atg<br>Met Asn Lys Val Gly Met Phe Tyr Thr Tyr Trp Ser Thr Glu Trp Met<br>1                     5                    10                 15 | | 48 |
| gtc gac ttt ccg gcg act gcg aag cgc att gcc ggg ctc ggc ttc gac<br>Val Asp Phe Pro Ala Thr Ala Lys Arg Ile Ala Gly Leu Gly Phe Asp<br>                  20                    25                    30 | | 96 |
| tta atg gaa atc tcg ctc ggc gag ttt cac aat ctt tcc gac gcg aag<br>Leu Met Glu Ile Ser Leu Gly Glu Phe His Asn Leu Ser Asp Ala Lys<br>35                     40                    45 | | 144 |
| aag cgt gag cta aaa gcc gtg gct gat gat ctg ggg ctc acg gtg atg<br>Lys Arg Glu Leu Lys Ala Val Ala Asp Asp Leu Gly Leu Thr Val Met<br>50                     55                    60 | | 192 |
| tgc tgt atc gga ctg aag tct gag tac gac ttt gcc tcg ccg gac aag<br>Cys Cys Ile Gly Leu Lys Ser Glu Tyr Asp Phe Ala Ser Pro Asp Lys<br>65                     70                    75                    80 | | 240 |
| agc gtt cgt gat gcc ggc acg gaa tat gtg aag cgc ttg ctc gac gac<br>Ser Val Arg Asp Ala Gly Thr Glu Tyr Val Lys Arg Leu Leu Asp Asp<br>                  85                    90                    95 | | 288 |
| tgt cac ctc ctc ggt gcg ccg gtc ttt gct ggc ctt acg ttc tgc gcg<br>Cys His Leu Leu Gly Ala Pro Val Phe Ala Gly Leu Thr Phe Cys Ala<br>                      100                   105                 110 | | 336 |
| tgg ccc caa tct ccg ccg ctg gac atg aag gat aag cgc cct tac gtc<br>Trp Pro Gln Ser Pro Pro Leu Asp Met Lys Asp Lys Arg Pro Tyr Val<br>                   115                   120                125 | | 384 |
| gac cgt gca atc gaa agc gtt cgt cgt gtt atc aag gta gct gaa gac<br>Asp Arg Ala Ile Glu Ser Val Arg Arg Val Ile Lys Val Ala Glu Asp<br>130                   135                 140 | | 432 |
| tac ggc att att tat gca ctg gaa gtg gtg aac cga ttc gag cag tgg<br>Tyr Gly Ile Ile Tyr Ala Leu Glu Val Val Asn Arg Phe Glu Gln Trp | | 480 |

```
                        145                 150                 155                 160 ctt tgc aat gac gcc aag gaa gca att gcg ttt gcc gac gcg gtt gac         528
Leu Cys Asn Asp Ala Lys Glu Ala Ile Ala Phe Ala Asp Ala Val Asp
                165                 170                 175 agt ccg gcg tgc aag gtc cag ctc gac aca ttc cac atg aat atc gaa         576
Ser Pro Ala Cys Lys Val Gln Leu Asp Thr Phe His Met Asn Ile Glu
            180                 185                 190 gag act tcc ttc cgc gat gca atc ctt gcc tgc aag ggc aag atg ggc         624
Glu Thr Ser Phe Arg Asp Ala Ile Leu Ala Cys Lys Gly Lys Met Gly
        195                 200                 205 cat ttc cat ttg ggc gaa gcg aac cgt ctg ccg ccg ggc gag ggt cgc         672
His Phe His Leu Gly Glu Ala Asn Arg Leu Pro Pro Gly Glu Gly Arg
    210                 215                 220 ctg ccg tgg gat gaa ata ttc ggg gcg ctg aag gaa atc gga tat gac         720
Leu Pro Trp Asp Glu Ile Phe Gly Ala Leu Lys Glu Ile Gly Tyr Asp
225                 230                 235                 240 ggc acc atc gtt atg gaa ccg ttc atg cgc aag ggc ggc tcg gtc agc         768
Gly Thr Ile Val Met Glu Pro Phe Met Arg Lys Gly Gly Ser Val Ser
                245                 250                 255 cgc gcg gtg ggc gta tgg cgg gat atg tcg aac ggt gcg acg gac gaa         816
Arg Ala Val Gly Val Trp Arg Asp Met Ser Asn Gly Ala Thr Asp Glu
            260                 265                 270 gag atg gac gag cgc gct cgc cgc tcg ttg cag ttt gtt cgt gac aag         864
Glu Met Asp Glu Arg Ala Arg Arg Ser Leu Gln Phe Val Arg Asp Lys
        275                 280                 285 ctg gcc tga                                                             873
Leu Ala
    290

<210> SEQ ID NO 11
<211> LENGTH: 290
<212> TYPE: PRT
<213> ORGANISM: artificial sequence
<220> FEATURE:
<223> OTHER INFORMATION: Synthetic Construct

<400> SEQUENCE: 11

Met Asn Lys Val Gly Met Phe Tyr Thr Tyr Trp Ser Thr Glu Trp Met
1               5                   10                  15

Val Asp Phe Pro Ala Thr Ala Lys Arg Ile Ala Gly Leu Gly Phe Asp
            20                  25                  30

Leu Met Glu Ile Ser Leu Gly Glu Phe His Asn Leu Ser Asp Ala Lys
        35                  40                  45

Lys Arg Glu Leu Lys Ala Val Ala Asp Asp Leu Gly Leu Thr Val Met
    50                  55                  60

Cys Cys Ile Gly Leu Lys Ser Glu Tyr Asp Phe Ala Ser Pro Asp Lys
65                  70                  75                  80

Ser Val Arg Asp Ala Gly Thr Glu Tyr Val Lys Arg Leu Leu Asp Asp
                85                  90                  95

Cys His Leu Leu Gly Ala Pro Val Phe Ala Gly Leu Thr Phe Cys Ala
            100                 105                 110

Trp Pro Gln Ser Pro Leu Asp Met Lys Asp Lys Arg Pro Tyr Val
        115                 120                 125

Asp Arg Ala Ile Glu Ser Val Arg Val Ile Lys Val Ala Glu Asp
    130                 135                 140

Tyr Gly Ile Ile Tyr Ala Leu Glu Val Val Asn Arg Phe Glu Gln Trp
145                 150                 155                 160

Leu Cys Asn Asp Ala Lys Glu Ala Ile Ala Phe Ala Asp Ala Val Asp
```

```
                165                 170                 175
Ser Pro Ala Cys Lys Val Gln Leu Asp Thr Phe His Met Asn Ile Glu
        180                 185                 190

Glu Thr Ser Phe Arg Asp Ala Ile Leu Ala Cys Lys Gly Lys Met Gly
        195                 200                 205

His Phe His Leu Gly Glu Ala Asn Arg Leu Pro Pro Gly Glu Gly Arg
    210                 215                 220

Leu Pro Trp Asp Glu Ile Phe Gly Ala Leu Lys Glu Ile Gly Tyr Asp
225                 230                 235                 240

Gly Thr Ile Val Met Glu Pro Phe Met Arg Lys Gly Gly Ser Val Ser
                245                 250                 255

Arg Ala Val Gly Val Trp Arg Asp Met Ser Asn Gly Ala Thr Asp Glu
            260                 265                 270

Glu Met Asp Glu Arg Ala Arg Arg Ser Leu Gln Phe Val Arg Asp Lys
        275                 280                 285

Leu Ala
    290
```

<210> SEQ ID NO 12
<211> LENGTH: 26
<212> TYPE: DNA
<213> ORGANISM: artificial sequence
<220> FEATURE:
<223> OTHER INFORMATION: primer

<400> SEQUENCE: 12
gaactagtgg atccgtagaa atcttg                                          26

<210> SEQ ID NO 13
<211> LENGTH: 44
<212> TYPE: DNA
<213> ORGANISM: artificial sequence
<220> FEATURE:
<223> OTHER INFORMATION: primer

<400> SEQUENCE: 13
ctttgttcat tttggcgcgc cttttagttt aataagggtc cgtg                      44

<210> SEQ ID NO 14
<211> LENGTH: 38
<212> TYPE: DNA
<213> ORGANISM: artificial sequence
<220> FEATURE:
<223> OTHER INFORMATION: primer

<400> SEQUENCE: 14
aaactaaaag gcgcgccaaa atgaacaaag ttggcatg                             38

<210> SEQ ID NO 15
<211> LENGTH: 36
<212> TYPE: DNA
<213> ORGANISM: artificial sequence
<220> FEATURE:
<223> OTHER INFORMATION: primer

<400> SEQUENCE: 15
ttctcttcga gagcatgctc aggccagctt gtcacg                               36

<210> SEQ ID NO 16
<211> LENGTH: 35
<212> TYPE: DNA
<213> ORGANISM: artificial sequence
<220> FEATURE:
<223> OTHER INFORMATION: primer

<400> SEQUENCE: 16
aagctggcct gagcatgctc tcgaagagaa tctag          35

<210> SEQ ID NO 17
<211> LENGTH: 26
<212> TYPE: DNA
<213> ORGANISM: artificial sequence
<220> FEATURE:
<223> OTHER INFORMATION: primer

<400> SEQUENCE: 17
gttccgcgga gaatgacacg gccgac          26

<210> SEQ ID NO 18
<211> LENGTH: 31
<212> TYPE: DNA
<213> ORGANISM: artificial sequence
<220> FEATURE:
<223> OTHER INFORMATION: primer

<400> SEQUENCE: 18
aaggcgcgcc aaaatgactg ctaacccttc c          31

<210> SEQ ID NO 19
<211> LENGTH: 27
<212> TYPE: DNA
<213> ORGANISM: artificial sequence
<220> FEATURE:
<223> OTHER INFORMATION: primer

<400> SEQUENCE: 19
gagcatgctt actcagggcc gtcaatg          27

<210> SEQ ID NO 20
<211> LENGTH: 22
<212> TYPE: DNA
<213> ORGANISM: artificial sequence
<220> FEATURE:
<223> OTHER INFORMATION: primer

<400> SEQUENCE: 20
gaagactagt tcacgtgatc tc          22

<210> SEQ ID NO 21
<211> LENGTH: 30
<212> TYPE: DNA
<213> ORGANISM: artificial sequence
<220> FEATURE:
<223> OTHER INFORMATION: primer

<400> SEQUENCE: 21
cactggcgcg cctttttgtgt ggtggtgtcc          30

<210> SEQ ID NO 22
<211> LENGTH: 33
<212> TYPE: DNA
<213> ORGANISM: artificial sequence
<220> FEATURE:
<223> OTHER INFORMATION: primer

<400> SEQUENCE: 22
tagcagcatg cataggttag tgaatgaggt atg          33

<210> SEQ ID NO 23
<211> LENGTH: 28
<212> TYPE: DNA
<213> ORGANISM: artificial sequence
<220> FEATURE:
<223> OTHER INFORMATION: primer

<400> SEQUENCE: 23
taggtccgcg ggagcttcgt taaagggc                                28

<210> SEQ ID NO 24
<211> LENGTH: 116
<212> TYPE: DNA
<213> ORGANISM: artificial sequence
<220> FEATURE:
<223> OTHER INFORMATION: primer

<400> SEQUENCE: 24
cactggcgcg cccactgcat gcgtcgacaa cccttaatat aacttcgtat aatgtatgct    60
atacgaagtt attaggtcta gacacatcgt ggatccaagc tatcaacgag agagtc       116

<210> SEQ ID NO 25
<211> LENGTH: 105
<212> TYPE: DNA
<213> ORGANISM: artificial sequence
<220> FEATURE:
<223> OTHER INFORMATION: primer

<400> SEQUENCE: 25
agtggctagc agtgccatgg cctaataact tcgtatagca tacattatac gaagttatat    60
taagggttct cgagacgcgt catctagcat ctcatctacc aactc                   105

<210> SEQ ID NO 26
<211> LENGTH: 30
<212> TYPE: DNA
<213> ORGANISM: artificial sequence
<220> FEATURE:
<223> OTHER INFORMATION: primer

<400> SEQUENCE: 26
cactctgcag cactggcgcg cccactgcat                              30

<210> SEQ ID NO 27
<211> LENGTH: 30
<212> TYPE: DNA
<213> ORGANISM: artificial sequence
<220> FEATURE:
<223> OTHER INFORMATION: primer

<400> SEQUENCE: 27
cactgatatc agtggctagc agtgccatgg                              30

<210> SEQ ID NO 28
<211> LENGTH: 590
<212> TYPE: DNA
<213> ORGANISM: artificial sequence
<220> FEATURE:
<223> OTHER INFORMATION: sequence encoding the nat1 gene of Streptomyces
      noursei

<400> SEQUENCE: 28
ggcgcgccaa aatgggtacc actttggacg acactgctta cagatacaga acctctgtcc    60
caggtgacgc cgaggccatc gaggctttgg atggttcctt caccaccgac accgtcttca    120

```
gagtcaccgc caccggtgac ggtttcacct tgagagaggt tccagttgac ccacctttga    180
ccaaggtttt cccagacgac gaatctgacg acgaatctga cgacggtgag gacggtgacc    240
cagactccag aactttcgtc gcctacggtg acgacggtga cttggctggt ttcgttgtcg    300
tctcttactc cggttggaac agaagattga ccgtcgagga catcgaggtc gccccagagc    360
acagaggtca cggtgtcggt agagctttga tgggtttggc tactgagttc gccagagaga    420
gaggtgccgg tcacttgtgg ttggaggtca ccaacgtcaa cgctccagct atccacgctt    480
acagaagaat gggtttcacc ttgtgtggtt tggacaccgc cttgtacgac ggtaccgcct    540
ccgacggtga gcaggctttg tacatgtcca tgccatgtcc ataagcatgc                590
```

```
<210> SEQ ID NO 29
<211> LENGTH: 29
<212> TYPE: DNA
<213> ORGANISM: artificial sequence
<220> FEATURE:
<223> OTHER INFORMATION: primer

<400> SEQUENCE: 29
caagcatgcg ggaatgataa gagactttg                                       29

<210> SEQ ID NO 30
<211> LENGTH: 31
<212> TYPE: DNA
<213> ORGANISM: artificial sequence
<220> FEATURE:
<223> OTHER INFORMATION: primer

<400> SEQUENCE: 30
ggaccgcgga aggtgagga agtatatgaa c                                     31

<210> SEQ ID NO 31
<211> LENGTH: 38
<212> TYPE: DNA
<213> ORGANISM: artificial sequence
<220> FEATURE:
<223> OTHER INFORMATION: primer

<400> SEQUENCE: 31
cacttctaga cactatcgat ggatccgtag aaatcttg                             38

<210> SEQ ID NO 32
<211> LENGTH: 29
<212> TYPE: DNA
<213> ORGANISM: artificial sequence
<220> FEATURE:
<223> OTHER INFORMATION: primer

<400> SEQUENCE: 32
cactacgcgt aaaggtgagg aagtatatg                                       29

<210> SEQ ID NO 33
<211> LENGTH: 30
<212> TYPE: DNA
<213> ORGANISM: artificial sequence
<220> FEATURE:
<223> OTHER INFORMATION: primer

<400> SEQUENCE: 33
cactctgcag gatccaagct atcaacgaga                                      30

<210> SEQ ID NO 34
<211> LENGTH: 28
```

```
<212> TYPE: DNA
<213> ORGANISM: artificial sequence
<220> FEATURE:
<223> OTHER INFORMATION: primer

<400> SEQUENCE: 34
cactgcatgc gttgcggaaa aaacagcc                                          28

<210> SEQ ID NO 35
<211> LENGTH: 34
<212> TYPE: DNA
<213> ORGANISM: artificial sequence
<220> FEATURE:
<223> OTHER INFORMATION: primer

<400> SEQUENCE: 35
cactccatgg agtaggtata taaaaatata agag                                   34

<210> SEQ ID NO 36
<211> LENGTH: 28
<212> TYPE: DNA
<213> ORGANISM: artificial sequence
<220> FEATURE:
<223> OTHER INFORMATION: primer

<400> SEQUENCE: 36
cactgctagc gtcgacaaca gcaactag                                          28

<210> SEQ ID NO 37
<211> LENGTH: 19
<212> TYPE: DNA
<213> ORGANISM: artificial sequence
<220> FEATURE:
<223> OTHER INFORMATION: primer

<400> SEQUENCE: 37
caagtcgtgg agattctgc                                                    19

<210> SEQ ID NO 38
<211> LENGTH: 34
<212> TYPE: DNA
<213> ORGANISM: artificial sequence
<220> FEATURE:
<223> OTHER INFORMATION: primer

<400> SEQUENCE: 38
caaggcgcgc caaaatgtct accaaaacca ttac                                   34

<210> SEQ ID NO 39
<211> LENGTH: 28
<212> TYPE: DNA
<213> ORGANISM: artificial sequence
<220> FEATURE:
<223> OTHER INFORMATION: primer

<400> SEQUENCE: 39
ggagcatgcc tactttccct cagccaag                                          28

<210> SEQ ID NO 40
<211> LENGTH: 30
<212> TYPE: DNA
<213> ORGANISM: artificial sequence
<220> FEATURE:
<223> OTHER INFORMATION: primer

<400> SEQUENCE: 40
```

```
atatcccggg caccgtcatc accgaaacgc                                           30
```

<210> SEQ ID NO 41
<211> LENGTH: 29
<212> TYPE: DNA
<213> ORGANISM: artificial sequence
<220> FEATURE:
<223> OTHER INFORMATION: primer

<400> SEQUENCE: 41

```
atatcccggg cacgaccacg ctgatgagc                                            29
```

<210> SEQ ID NO 42
<211> LENGTH: 1415
<212> TYPE: DNA
<213> ORGANISM: artificial sequence
<220> FEATURE:
<223> OTHER INFORMATION: Sequence encoding the NAD+-specific D-arabitol
      4-oxidoreductase from R. solanacearum
<220> FEATURE:
<221> NAME/KEY: CDS
<222> LOCATION: (12)..(1409)

<400> SEQUENCE: 42

```
ggcgcgccaa a atg acc aga tct tct ttg gct aga gct cca gtt ttg ttg     50
            Met Thr Arg Ser Ser Leu Ala Arg Ala Pro Val Leu Leu
            1               5                   10 cac atc ggt gct ggt tct ttc cac aga gct cac cag gct tgg tac ttg      98
His Ile Gly Ala Gly Ser Phe His Arg Ala His Gln Ala Trp Tyr Leu
        15                  20                  25 cac aga gtt aac gct gct gtt cca cca ggt gag aga tgg acc ttg acc     146
His Arg Val Asn Ala Ala Val Pro Pro Gly Glu Arg Trp Thr Leu Thr
30                  35                  40                  45 gtt ggt aac atc aga gac gac atg cac gct acc ttg gct gct ttg gct     194
Val Gly Asn Ile Arg Asp Asp Met His Ala Thr Leu Ala Ala Leu Ala
                50                  55                  60 gct cag cag ggt gct tac acc ttg gag acc gtt acc cca cag ggt gag     242
Ala Gln Gln Gly Ala Tyr Thr Leu Glu Thr Val Thr Pro Gln Gly Glu
            65                  70                  75 aga gct tac gag acc atc aga tct atc gct aga gtt ttg cct tgg tct     290
Arg Ala Tyr Glu Thr Ile Arg Ser Ile Ala Arg Val Leu Pro Trp Ser
        80                  85                  90 gct gac ttg gct gct ttg atc aac acc ggt gct gac cca gct tgt aga     338
Ala Asp Leu Ala Ala Leu Ile Asn Thr Gly Ala Asp Pro Ala Cys Arg
    95                  100                 105 atc gtt tct ttc acc gtt acc gag ggt ggt tac tac ttg gac gag cac     386
Ile Val Ser Phe Thr Val Thr Glu Gly Gly Tyr Tyr Leu Asp Glu His
110                 115                 120                 125 gac aga ttg gac gtt acc cac cca gac ttg gct gct gac ttg aga ggt     434
Asp Arg Leu Asp Val Thr His Pro Asp Leu Ala Ala Asp Leu Arg Gly
                130                 135                 140 gct aga tct acc ttg tac ggt gct ttg gct gct ttg ttg gct gag aga     482
Ala Arg Ser Thr Leu Tyr Gly Ala Leu Ala Ala Leu Leu Ala Glu Arg
            145                 150                 155 aga cag aga ggt gct ggt cca ttg acc ttg cag tct tgt gac aac ttg     530
Arg Gln Arg Gly Ala Gly Pro Leu Thr Leu Gln Ser Cys Asp Asn Leu
        160                 165                 170 aga tct aac ggt gct aga ttc aga gct ggt atg aga gct ttc ttg gct     578
Arg Ser Asn Gly Ala Arg Phe Arg Ala Gly Met Arg Ala Phe Leu Ala
    175                 180                 185 ttg aga ggt gac gct gct ttg ttg gct tgg ttc gac gct aac gtt tct     626
Leu Arg Gly Asp Ala Ala Leu Leu Ala Trp Phe Asp Ala Asn Val Ser
190                 195                 200                 205
```

```
tgt cca tct gct atg gtt gac aga atc acc cca aga cca acc gac gac      674
Cys Pro Ser Ala Met Val Asp Arg Ile Thr Pro Arg Pro Thr Asp Asp
            210                 215                 220 gtt aga acc aga gtt cac gct gct acc ggt gtt gac gac aga tgt cca      722
Val Arg Thr Arg Val His Ala Ala Thr Gly Val Asp Asp Arg Cys Pro
                225                 230                 235 gtt atg ggt gag tct ttc atc cag tgg gtt atc gag gac aac ttc atc      770
Val Met Gly Glu Ser Phe Ile Gln Trp Val Ile Glu Asp Asn Phe Ile
            240                 245                 250 gct ggt aga cca gct tgg gag atc gct ggt gct gag atc gtt gct gac      818
Ala Gly Arg Pro Ala Trp Glu Ile Ala Gly Ala Glu Ile Val Ala Asp
                255                 260                 265 gtt cac cca tac gag gag gct aag atc aga atc ttg aac gct acc cac      866
Val His Pro Tyr Glu Glu Ala Lys Ile Arg Ile Leu Asn Ala Thr His
270                 275                 280                 285 tct tgt atc gct tgg gct ggt acc ttg gct ggt ttg acc tac atc cac      914
Ser Cys Ile Ala Trp Ala Gly Thr Leu Ala Gly Leu Thr Tyr Ile His
                    290                 295                 300 gag ggt atg aga gac gct gct atc tac aga ttc gct tac gac tac gtt      962
Glu Gly Met Arg Asp Ala Ala Ile Tyr Arg Phe Ala Tyr Asp Tyr Val
                305                 310                 315 acc gac gac gtt atc cca tgt ttg acc cca tct cca ttg gac ttg gag     1010
Thr Asp Asp Val Ile Pro Cys Leu Thr Pro Ser Pro Leu Asp Leu Glu
            320                 325                 330 aga tac aga gac gtt gtt ttg gag aga ttc ggt aac cca tac gtt ttg     1058
Arg Tyr Arg Asp Val Val Leu Glu Arg Phe Gly Asn Pro Tyr Val Leu
            335                 340                 345 gac acc aac cag aga gtt gct gct gac ggt ttc tct aag atc cca ggt     1106
Asp Thr Asn Gln Arg Val Ala Ala Asp Gly Phe Ser Lys Ile Pro Gly
350                 355                 360                 365 ttc atc gct cca acc ttg gct gag tgt ttc gct aga ggt gct gac cca     1154
Phe Ile Ala Pro Thr Leu Ala Glu Cys Phe Ala Arg Gly Ala Asp Pro
                    370                 375                 380 gtt gct acc gct gtt ttg cca gct ttg ttc ttg ggt ttc ttg gag ggt     1202
Val Ala Thr Ala Val Leu Pro Ala Leu Phe Leu Gly Phe Leu Glu Gly
                385                 390                 395 tgg gct aga ggt acc ttg cca tac gtt tac cag gac ggt gtt atg gac     1250
Trp Ala Arg Gly Thr Leu Pro Tyr Val Tyr Gln Asp Gly Val Met Asp
            400                 405                 410 ggt gct gct gct aga tct atc gtt gag gct cca gac tct gtt gct gct     1298
Gly Ala Ala Ala Arg Ser Ile Val Glu Ala Pro Asp Ser Val Ala Ala
            415                 420                 425 ttc tgt tct gac aga cag ttg tgg ggt tct ttg gct ggt aga gac gct     1346
Phe Cys Ser Asp Arg Gln Leu Trp Gly Ser Leu Ala Gly Arg Asp Ala
430                 435                 440                 445 ttg gtt cag gct gtt aga gct ggt aga gct aga gtt gag gct tgg aga     1394
Leu Val Gln Ala Val Arg Ala Gly Arg Ala Arg Val Glu Ala Trp Arg
                450                 455                 460 gct gct aga aga tga gcatgc                                           1415
Ala Ala Arg Arg
            465
```

<210> SEQ ID NO 43
<211> LENGTH: 465
<212> TYPE: PRT
<213> ORGANISM: artificial sequence
<220> FEATURE:
<223> OTHER INFORMATION: Synthetic Construct

<400> SEQUENCE: 43

```
Met Thr Arg Ser Ser Leu Ala Arg Ala Pro Val Leu Leu His Ile Gly
1               5                   10                  15

Ala Gly Ser Phe His Arg Ala His Gln Ala Trp Tyr Leu His Arg Val
            20                  25                  30

Asn Ala Ala Val Pro Pro Gly Glu Arg Trp Thr Leu Thr Val Gly Asn
                35                  40                  45

Ile Arg Asp Asp Met His Ala Thr Leu Ala Ala Leu Ala Ala Gln Gln
50                  55                  60

Gly Ala Tyr Thr Leu Glu Thr Val Thr Pro Gln Gly Glu Arg Ala Tyr
65                  70                  75                  80

Glu Thr Ile Arg Ser Ile Ala Arg Val Leu Pro Trp Ser Ala Asp Leu
                85                  90                  95

Ala Ala Leu Ile Asn Thr Gly Ala Asp Pro Ala Cys Arg Ile Val Ser
                100                 105                 110

Phe Thr Val Thr Glu Gly Gly Tyr Tyr Leu Asp Glu His Asp Arg Leu
            115                 120                 125

Asp Val Thr His Pro Asp Leu Ala Ala Asp Leu Arg Gly Ala Arg Ser
            130                 135                 140

Thr Leu Tyr Gly Ala Leu Ala Ala Leu Leu Ala Glu Arg Arg Gln Arg
145                 150                 155                 160

Gly Ala Gly Pro Leu Thr Leu Gln Ser Cys Asp Asn Leu Arg Ser Asn
                165                 170                 175

Gly Ala Arg Phe Arg Ala Gly Met Arg Ala Phe Leu Ala Leu Arg Gly
            180                 185                 190

Asp Ala Ala Leu Leu Ala Trp Phe Asp Ala Asn Val Ser Cys Pro Ser
            195                 200                 205

Ala Met Val Asp Arg Ile Thr Pro Arg Pro Thr Asp Asp Val Arg Thr
210                 215                 220

Arg Val His Ala Ala Thr Gly Val Asp Asp Arg Cys Pro Val Met Gly
225                 230                 235                 240

Glu Ser Phe Ile Gln Trp Val Ile Glu Asp Asn Phe Ile Ala Gly Arg
                245                 250                 255

Pro Ala Trp Glu Ile Ala Gly Ala Glu Ile Val Ala Asp Val His Pro
            260                 265                 270

Tyr Glu Glu Ala Lys Ile Arg Ile Leu Asn Ala Thr His Ser Cys Ile
            275                 280                 285

Ala Trp Ala Gly Thr Leu Ala Gly Leu Thr Tyr Ile His Glu Gly Met
            290                 295                 300

Arg Asp Ala Ala Ile Tyr Arg Phe Ala Tyr Asp Tyr Val Thr Asp Asp
305                 310                 315                 320

Val Ile Pro Cys Leu Thr Pro Ser Pro Leu Asp Leu Glu Arg Tyr Arg
                325                 330                 335

Asp Val Val Leu Glu Arg Phe Gly Asn Pro Tyr Val Leu Asp Thr Asn
            340                 345                 350

Gln Arg Val Ala Ala Asp Gly Phe Ser Lys Ile Pro Gly Phe Ile Ala
            355                 360                 365

Pro Thr Leu Ala Glu Cys Phe Ala Arg Gly Ala Asp Pro Val Ala Thr
370                 375                 380

Ala Val Leu Pro Ala Leu Phe Leu Gly Phe Leu Glu Gly Trp Ala Arg
385                 390                 395                 400

Gly Thr Leu Pro Tyr Val Tyr Gln Asp Gly Val Met Asp Gly Ala Ala
            405                 410                 415

Ala Arg Ser Ile Val Glu Ala Pro Asp Ser Val Ala Ala Phe Cys Ser
```

-continued

```
                420                 425                 430

Asp Arg Gln Leu Trp Gly Ser Leu Ala Gly Arg Asp Ala Leu Val Gln
        435                 440                 445

Ala Val Arg Ala Gly Arg Ala Arg Val Glu Ala Trp Arg Ala Ala Arg
    450                 455                 460

Arg
465
```